United States Patent
Hurst et al.

(10) Patent No.: US 6,703,387 B2
(45) Date of Patent: Mar. 9, 2004

(54) INHIBITORS OF HPV E1 HELICASE ENZYME

(75) Inventors: David N. Hurst, Welwyn (GB); Philip Stephen Jones, Welwyn Garden City (GB); Kevin Edward Burdon Parkes, Letchworth (GB); Martin John Parratt, Hertford (GB); Francis Xavier Wilson, Welwyn Garden City (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 279 days.

(21) Appl. No.: 09/892,148

(22) Filed: Jun. 26, 2001

(65) Prior Publication Data

US 2002/0128262 A1 Sep. 12, 2002

(30) Foreign Application Priority Data

Jun. 28, 2000 (GB) .............................................. 0015904

(51) Int. Cl.$^7$ .................... A61K 31/5513; C07D 243/14
(52) U.S. Cl. ...................... 514/218; 540/569; 540/572; 540/574
(58) Field of Search .......................... 514/218; 540/569, 540/572, 574

(56) References Cited

U.S. PATENT DOCUMENTS 3,426,014 A 2/1969 Schmitt ................... 260/239.3

FOREIGN PATENT DOCUMENTS

| EP | 350131 | * | 1/1990 |
| EP | 350 131 | | 1/1990 |
| EP | 359131 | * | 1/1990 |
| EP | 462 522 | | 12/1991 |
| WO | WO 00/12547 | | 3/2000 |
| WO | WO 00/14063 | | 3/2000 |

OTHER PUBLICATIONS

Maw et al., *International Journal of STD & AIDS,* vol. 9, pp. 571–578 (1998).
Koutsky L., *The American Journal of Medicine.*, vol. 102(5A), pp. 3–8 (1997).
Hansfield, H.H., *The American Journal of Medicine,* vol. 102(5A), pp. 16–20 (1997).
Sternbach et al., *Journal of Organic Chemistry,* vol. 28, pp. 3013–3016 (1963).
Buzas and Finet, *Tetrahedron Letters,* No. 28, pp. 2433–2436 (1976).
Kim et al., *Journal of the Chemical Societ,* Perkin Transactions I, pp. 1361–1363 (1997.
Howley, P., *Fields Virology* $2^{nd}$ Edn. Chapters 58 & 59, pp. 1625–1676 (1990) (Raven Press, NY).

* cited by examiner

Primary Examiner—Mukund J. Shah
Assistant Examiner—Sudhaker B. Patel
(74) Attorney, Agent, or Firm—George W. Johnston; Dennis P. Tramaloni

(57) ABSTRACT

The invention is concerned with novel benzodiazepine derivatives, a process for their manufacture, pharmaceutical compositions and the use of such compounds in medicine. In particular, the compounds are inhibitors of the human papillomavirus E1 helicase enzyme which is involved in viral replication. Consequently the compounds of this invention may be advantageously used as therapeutic agents for HPV mediated diseases.

6 Claims, No Drawings

INHIBITORS OF HPV E1 HELICASE ENZYME

BACKGROUND OF THE INVENTION

Human papillomaviruses (HPV) are non-enveloped DNA viruses that induce hyperproliferative lesions of cutaneous and mucosal epithelia (warts).(Ref: P Howley—In Fields Virology $2^{nd}$ Edn. Chap. 58 pp1625–1676 eds Fields et al Raven Press NY 1990) Genital HPV infection is one of the most common sexually transmitted diseases. (Ref Maw RD, Reitas M and Roy M, Int J STD+AIDS 9, 571–578, (1998)). It is estimated that visible genital warts are present in 1% of sexually active adults in the USA and that at least 15% have subclinical infection. (Koutsky L., Am. J. Med. 102, 3–8 (1997)). Over 90% of benign external warts (condyloma acuminata) are caused by HPV genotypes 6 and 11 (Handsfield H. H. Am. J. Med. 102, 16–27 (1997)).

E1 Helicase is the only known HPV enzyme and is essential for viral DNA replication. The E1 protein has been shown to possess ATPase and ATP-dependent DNA helicase catalytic activities. It is proposed to function as a hexameric helicase and sequence homology classifies it as a member of helicase superfamily III (other members: SV40 TAg, parvovirus NS1). Inhibition of the ATPase or helicase functions of this enzyme would be predicted to result in inhibition of HPV DNA replication.

The object of the present invention is to provide novel compounds which are potent inhibitors of the ATPase activity of the helicase enzyme and which accordingly show a potential to be efficacious as antiviral drugs.

SUMMARY OF THE INVENTION

The present invention comprises novel benzodiazepine derivatives of the formula

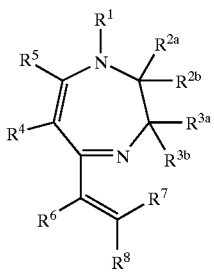

The novel compounds are inhibitors of the human papilloma virus (HPV) E1 helicase enzyme and can therefore be used as therapeutic agents for HPV mediated diseases.

DETAILED DESCRIPTION OF THE INVENTION

The present invention comprises novel compounds of the formula:

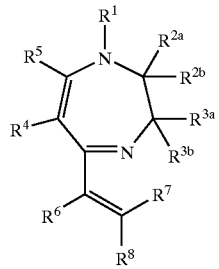

wherein
$R^1$ is H, lower alkyl, lower alkenyl, lower alkynyl, aryl lower alkyl, lower alkyl carbonyl, aryl carbonyl, lower alkyl amino carbonyl, aryl amino carbonyl, lower alkoxy carbonyl, aryloxy carbonyl,
$R^{2a}$, $R^{2b}$ independently are H or lower alkyl or
$R^{2a}$ and $R^{2b}$ together are oxo,
$R^1$ and $R^{2a}$ or $R^{2b}$ together with the nitrogen and the carbon atom to which they are attached form aheterocycle;
$R^{3a}$, $R^{3b}$ independently are H or lower alkyl
$R^4$ and $R^5$ together with the two carbon atoms to which they are attached form aryl or a heterocycle,
$R^6$ and $R^7$ is H or lower alkyl and
$R^8$ is aryl or heterocyclyl.

The term "lower" used in combination with alkyl and alkoxy defines an optionally substituted straight chained or branched alkyl chain carrying 1 to 6 carbon atoms, preferably 1 to 4 carbon atoms. The term "lower" used in combination with alkenyl and alkynyl defines an optionally substituted straight chained or branched alkenyl or alkynyl chain carrying 2 to 6 carbon atoms, preferably 2 to 4 carbon atoms.

Lower alkyl in $R^1$, $R^{2a}$, $R^{2b}$, $R^{3a}$, $R^{3b}$, $R^6$ and $R^7$ accordingly preferably stands for methyl, ethyl, n-propyl, i-propyl, n-butyl, i-butyl and tert.-butyl.

Lower alkoxy in $R^1$ preferably stands for methoxy, ethoxy, n-propoxy, i-propoxy, n-butoxy, i-butoxy and tert.-butoxy.

Lower alkenyl in $R^1$ accordingly preferably is vinyl, 1-propenyl, 2-propenyl, i-propenyl and butenyl and its isomers.

Lower alkynyl in $R^1$ accordingly preferably is ethynyl, propynyl and its isomers and butynyl and its isomers.

Preferred meaning for $R^1$ is methyl.

Preferred meaning for $R^{2a}$, $R^{2b}$, $R^{3a}$, $R^{3b}$, $R^6$ and $R^7$ is hydrogen.

Suitable substituents of an alkyl chain can be selected from one or more of aryl, heterocyclyl, carboxyl, cyano, alkoxy, cycloalkyl oxy, aryl oxy, heterocyclyl oxy, hydroxyl, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocylyl oxy carbonyl amino, alkyl amino carbonyl amino, dialkyl amino carbonyl amino, cycloalkyl amino carbonyl amino, aryl amino carbonyl amino, heterocyclyl amino carbonyl amino alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen.

In all cases above where there are NH groups, the free hydrogen may also be substituted, preferably with lower alkyl. Examples are alkyl carbonyl (lower alkyl) amino, cycloalkyl (lower alkyl) amino carbonyl or alkoxy carbonyl (lower alkyl) amino.

The term cycloalkyl has the meaning of an optionally substituted cycloalkyl group containing 3 to 8 carbon atoms, preferably 3 to 6 carbon atoms e.g. cyclopropyl, cyclobutyl, cyclopentyl, cyclohexyl, cycloheptyl and cyclooctyl or adamantyl which can also be benz-fused to an optionally substituted saturated, partially unsaturated or aromatic monocyclic, bicyclic or tricyclic heterocycle or carbocycle, e.g. to phenyl.

The term aryl denotes optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl.

The term heterocyclyl stands for an optionally substituted saturated, partially unsaturated or aromatic monocyclic, bicyclic or tricyclic heterocycle which contains one or more hetero atoms selected from nitrogen, oxygen and sulfur which can also be benz-fused to an optionally substituted saturated, partially unsaturated or aromatic monocyclic, bicyclic or tricyclic carbocycle or heterocycle.

Preferred heterocycles are oxazolyl, isoxazolyl, furyl, tetrahydrofuryl, 1,3-dioxolanyl, dihydropyranyl, thienyl, pyrazinyl, isothiazolyl isoquinolinyl, indolyl, indazolyl, quinolinyl, dihydrooxazolyl, pyrimidinyl, benzofuranyl, tetrazolyl, pyrrolidinonyl, (N-oxide)-pyridinyl, pyrrol, triazolyl e.g. 1,2,4-triazolyl, pyrazolyl, benzotriazolyl, priperidinyl, morpholinyl, thiazolyl, pyridinyl, dihydrothiazolyl, imidazolidinyl, pyrazolinyl, benzothienyl, piperazinyl, imidazolyl, thia diazolyl e.g. 1,2,3-thiadiazolyl, and benzothiazolyl.

Suitable substituents for cycloalkyl, aryl, heterocyclyl can be selected from those named for alkyl, in addition however lower alkyl, lower alkenyl and lower alkynyl are substituents to be added to the selection.

The term halogen stands for fluorine, chlorine, bromine and iodine.

$R^4$ and $R^5$ together with the two carbon atoms to which they are attached preferably form optionally substituted aryl, more preferably form optionally substituted phenyl.

$R^8$ preferably stands for optionally substituted aryl, more preferably for optionally substituted phenyl.

Any functional (i.e. reactive) group present in a side-chain may be protected, with the protecting group being a group which is known per se, for example, as described in "Protective Groups in Organic Synthesis", $2^{nd}$ Ed., T. W. Greene and P. G. M. Wuts, John Wiley & Sons, New York, N.Y., 1991. For example, an amino group can be protected by a tert.-butoxycarbonyl (BOC), formyl, trityl, benzyloxycarbonyl (Z), 9-fluorenylmethyloxcarbonyl (FMOC), trifluoroacetyl, 2-(biphenylyl)isopropoxycarbonyl or isobornyloxycarbonyl group or in the form of a phthalimido group; or a hydroxyl group can be protected by a tert.butyldimethylsilyl, tetrahydropyranyl, 4-methoxybenzyl, or benzyl; or a carboxyl group can be protected in the form of an ester, for example as a methyl or tert.butyl ester. The protecting group may be retained in the final compound or optionally be removed by techniques known in the art.

The compounds of this invention may contain one or more asymmetric carbon atoms and may therefore occur as racemates and racemic mixtures, single enantiomers, diastereomeric mixtures and individual diastereomers. Furthermore, where a compound of the invention contains an olefinic double bond, this can have the (E) or (Z) configuration. Also, each chiral center may be of the R or S configuration. All such isomeric forms of these compounds are embraced by the present invention.

Compounds of formula (I) which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula (I) which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

Preferred compounds of formula (I) are those having the formula

II

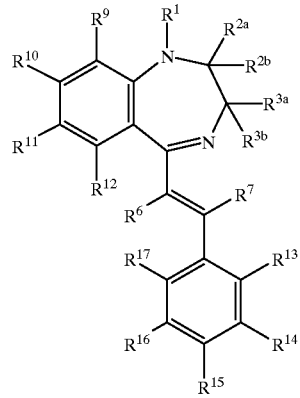

wherein
$R^1$, $R^{2a}$, $R^{2b}$, $R^{3a}$, $R^{3b}$, $R^6$ and R 7 are as above and
$R^9$, $R^{10}$, $R^{11}$, $R^{12}$, $R^{13}$, $R^{14}$, $R^{15}$, $R^{16}$ and $R^{17}$ independently are H, lower alkyl, lower alkenyl, lower alkynyl, cycloalkyl, aryl, heterocyclyl, carboxyl, cyano, alkoxy, cycloalkyl oxy, aryl oxy, heterocyclyl oxy, hydroxyl, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocylyl oxy carbonyl amino, alkyl amino carbonyl amino, dialkyl amino carbonyl amino, cycloalkyl amino carbonyl amino, aryl amino carbonyl amino, heterocyclyl amino carbonyl amino, alkyl carbonyl amino alkyl carbonyl amino, dialkyl amino carbonyl amino alkyl carbonyl amino, cycloalkyl carbonyl amino alkyl carbonyl amino, aryl carbonyl amino alkyl carbonyl amino, heterocyclyl carbonyl amino alkyl carbonyl amino, alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen or $R^{10}$ and $R^{11}$ together with the two carbon atoms to which they are attached form optionally substituted aryl or an optionally substituted heterocycle.

Preferred meaning for $R^1$ is methyl.

Preferred meaning for $R^{2a}$, $R^{2b}$, $R^{3a}$, $R^{3b}$, $R^6$ and $R^7$ is hydrogen.

More preferred compounds of formula (I) are those having the formula

III

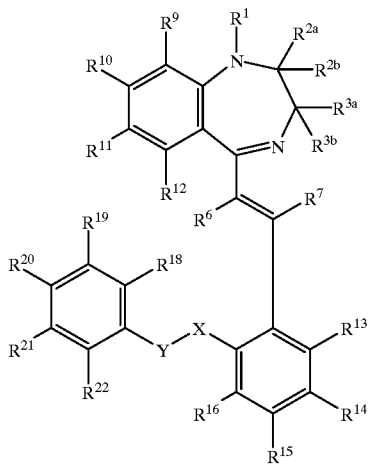

wherein
$R^1, R^{2a}, R^{2b}, R^{3a}, R^{3b}, R^6, R^7, R^9, R^{10}, R^{11}, R^{12}, R^{13}, R^{14}, R^{15}$ and $R^{16}$ are as above and wherein X is $(CH_2—)_n$ with n being an integer between 0 and 3, —S—, —O— or —$NR^{23}$, wherein $R^{23}$ is H or lower alkyl, Y is —$(CH_2—)_n$ with n being an integer between 0 and 3, and when X is $(CH_2—)_n$ with n being an integer between 0 and 3 then Y is S, O or —$NR^{23}$ wherein $R^{23}$ is as above, $R^{18}$, $R^{19}$, $R^{20}$ and $R^{22}$ independently are H, lower alkyl, lower alkenyl, lower alkynyl, cycloalkyl, aryl, heterocyclyl, carboxyl, cyano, alkoxy, cycloalkyl oxy, aryl oxy, heterocyclyl oxy, hydroxyl, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocylyl oxy carbonyl amino, alkyl amino carbonyl amino, dialkyl amino carbonyl amino, cycloalkyl amino carbonyl amino, aryl amino carbonyl amino, heterocyclyl amino carbonyl amino, alkyl carbonyl amino alkyl carbonyl amino, dialkyl amino carbonyl amino alkyl carbonyl amino, cycloalkyl carbonyl amino alkyl carbonyl amino, aryl carbonyl amino alkyl carbonyl amino, heterocyclyl carbonyl amino alkyl carbonyl amino, alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen.

Preferred meaning for $R^1$ is methyl.

Preferred meaning for $R^{2a}$, $R^{2b}$, $R^{3a}$, $R^{3b}$, $R^6$ and $R^7$ is hydrogen.

Examples of compounds of formula I are set out below in table A:

TABLE A

| Structure | Names |
|---|---|
| 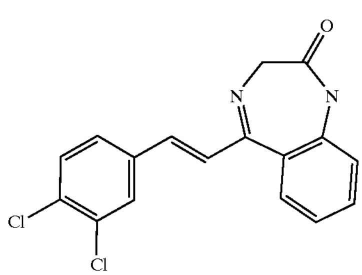 | (E)-5-(3,4-Dichlorostyryl)-1,3-dihydro-2H-benzo-1,4-diazepin-2-one |

TABLE A-continued

| Structure | Names |
|---|---|
| 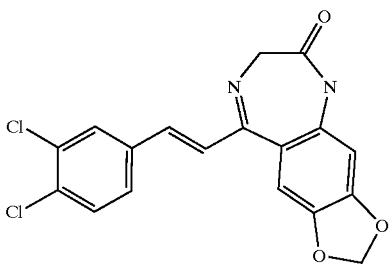 | (E)-9-(3,4-Dichlorostyryl)-5,7-dihydro-6H-1,3-dioxolo[4,5-h][1,4]benzodiazepin-6-one |
| 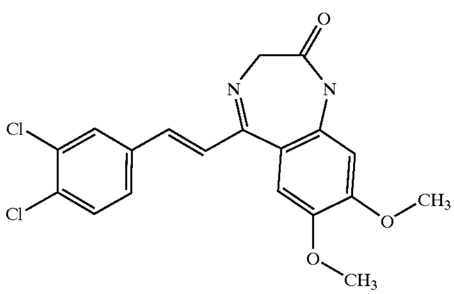 | (E)-5-(3,4-Dichlorostyryl)-1,3-dihydro-7,8-dimethoxy-2H-1,4-benzodiazepin-2-one |
| 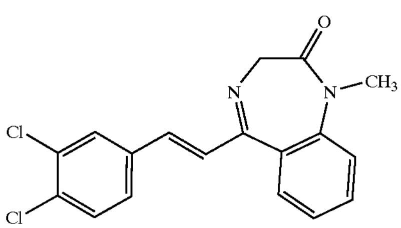 | (E)-5-(3,4-Dichlorostyryl)-1,3-dihydro-1-methyl-2H-benzo-1,4-diazepin-2-one |
| 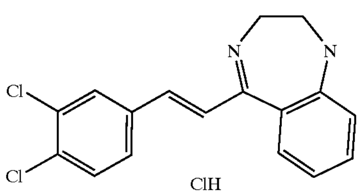 | (E)-5-(3,4-Dichlorostyryl)-2,3-dihydro-1H-benzo-1,4-diazepine dihydrochloride |
| 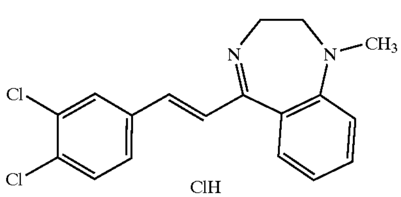 | (E)-5-(3,4-Dichlorostyryl)-2,3-dihydro-1-methyl-1H-benzo-1,4-diazepine dihydrochloride |
| 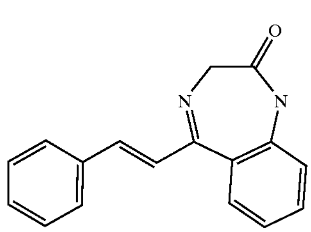 | (E)-1,3-Dihydro-5-styryl-2H-benzo-1,4-diazepin-2-one |

TABLE A-continued

| Structure | Names |
|---|---|
| 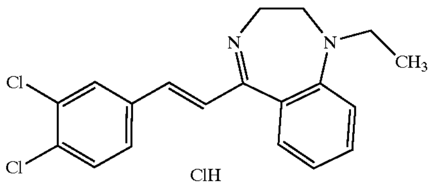 | (E)-5-(3,4-Dichlorostyryl)-1-ethyl-2,3-dihydro-1H-1,4-benzodiazepine dihydrochloride |
| 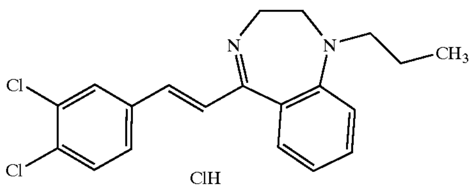 | (E)-5-(3,4-Dichlorostyryl)-2,3-dihydro-1-propyl-1H-1,4-benzodiazepine dihydrochloride |
| 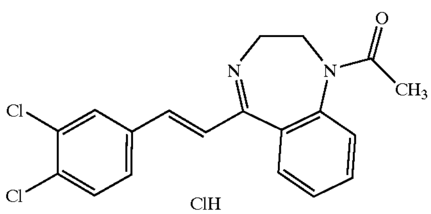 | (E)-1-Acetyl-5-(3,4-dichlorostyryl)-2,3-dihydro-1H-1,4-bezodiazepine hydrochloride |
| 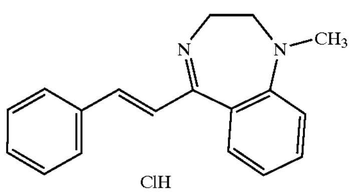 | (E)-2,3-Dihydro-1-methyl-5-styryl-1H-1,4-benzodiazepine dihydrochloride |
| 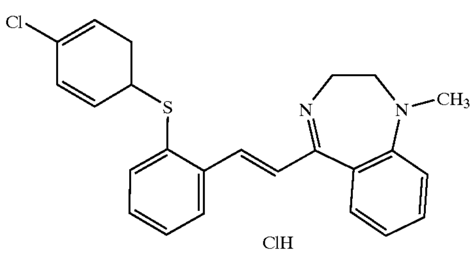 | (E)-5-[2-(4-Chlorophenylthio)styryl]-2,3-dihydro-1-methyl-1H-1,4-benzodiazepine dihydrochloride |
| 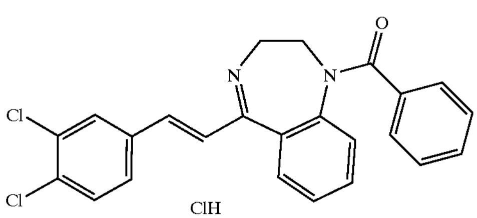 | (E)-1-Benzoyl-5-(3,4-dichlorostyryl)-2,3-dihydro-1H-1,4-benzodiazepine hydrochloride |
| 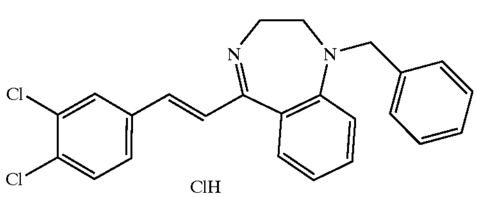 | (E)-1-Benzyl-5-(3,4-dichlorostyryl)-2,3-dihydro-1H-1,4-benzodiazepine dihydrochloride |

TABLE A-continued

| Structure | Names |
|---|---|
| 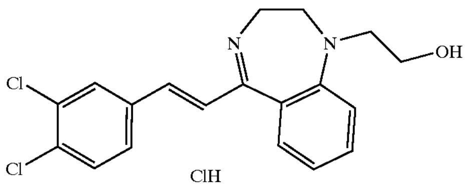 | (E)-5-(3,4-Dichlorostyryl)-2,3-dihydro-1H-1,4-benzodiazepine-1-ethanol hydrochloride |
| 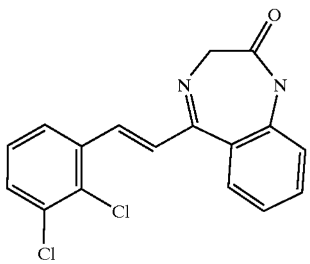 | (E)-5-(2,3-Dichlorostyryl)-1,3-dihydro-2H-1,4-benzodiazepin-2-one |
| 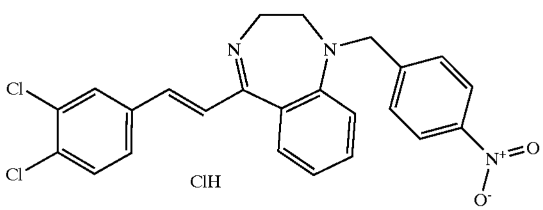 | (E)-5-(3,4-Dichlorostyryl)-2,3-dihydro-1-(4-nitrobenzyl)-1H-1,4-benzodiazepine dihydrochloride |
| 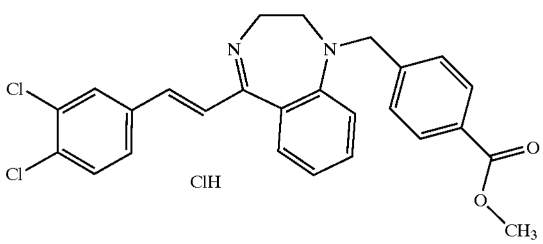 | Methyl (E)-4-[[5-(3,4-Dichlorostyryl)-2,3-dihydro-1H-1,4-benzodiazepin-1-yl]methyl]benzoate dihydrochloride |
| 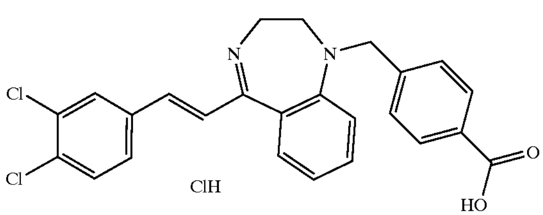 | (E)-4-[[5-(3,4-Dichlorostyryl)-2,3-dihydro-1H-1,4-benzodiazepin-1-yl[9 methyl[9 benzoic acid dihydrochloride |
| 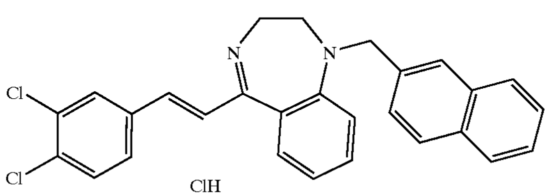 | (E)-5-(3,4-Dichlorostyryl)-2,3-dihydro-1-[(2-naphthyl)methyl]-1H-1,4-benzodiazepine dihydrochloride |
| 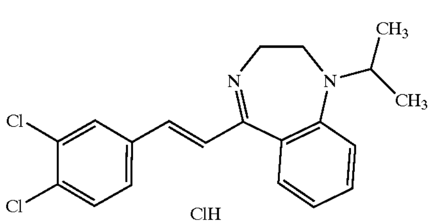 | (E)-5-(3,4-Dichlorostyryl)-2,3-dihydro-1-isopropyl-1H-1,4-benzodiazepine dihydrochloride |

TABLE A-continued

| Structure | Names |
|---|---|
| 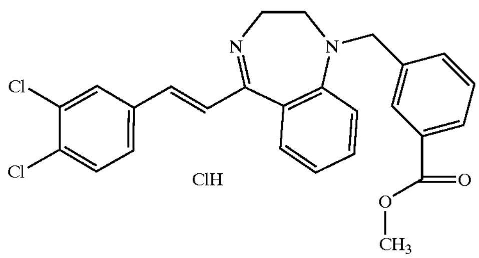 | Methyl (E)-3-[[5-(3,4-dichlorostyryl)-2,3-dihydro-1H-1,4-benzodiazepin-1-yl]methyl]benzoate hydrochloride |
| 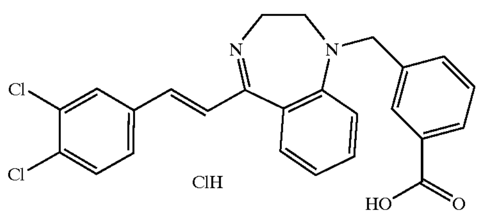 | (E)-3-[[5-(3,4-Dichlorostyryl)-2,3-dihydro-1H-1,4-benzodiazepin-1-yl]methyl]benzoic acid hydrochloride |
| 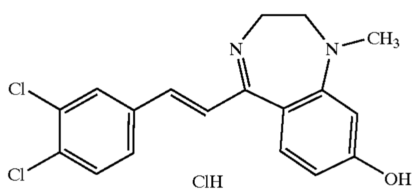 | (E)-5-(3,4-Dichlorostyryl)-2,3-dihydro-1-methyl-1H-1,4-benzodiazepin-8-ol hydrochloride |
| 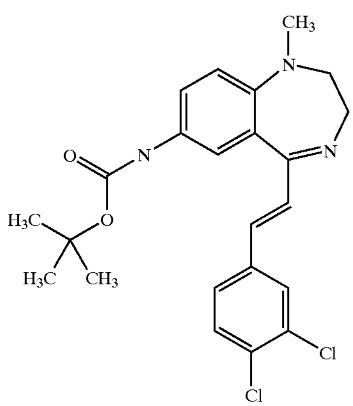 | tert-Butyl (E)-[5-(3,4-Dichlorostyryl)-2,3-dihydro-1-methyl-1H-1,4-benzodiazepin-7-yl]carbamate |
| 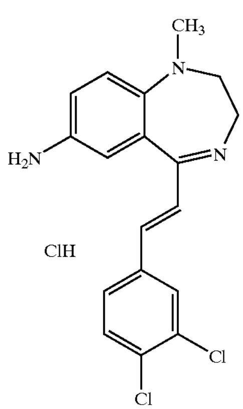 | (E)-5-(3,4-Dichlorostyryl)-2,3-dihydro-1-methyl-1H-1,4-benzodiazepin-7-amine hydrochloride |

TABLE A-continued

| Structure | Names |
|---|---|
| 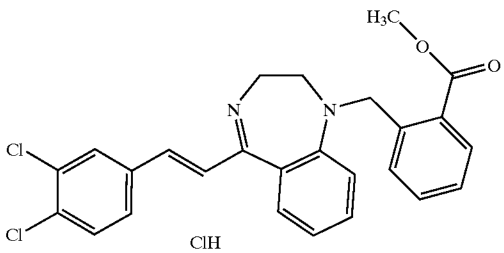 | Methyl (E)-2-[[5-(3,4-dichlorostyryl)-2,3-dihydro-1H-1,4-benzodiazepin-1-yl]methyl]benzoate hydrochloride |
| 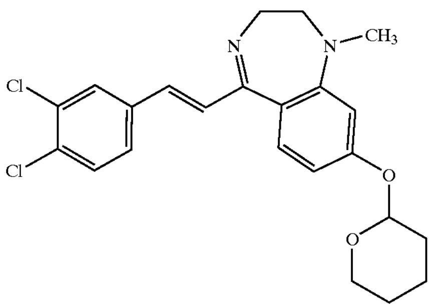 | (E)-5-(3,4-Dichlorostyryl)-2,3-dihydro-8-(tetrahydro-2(RS)-pyranyloxy)-1-methyl-1H-1,4-benzodiazepine |
| 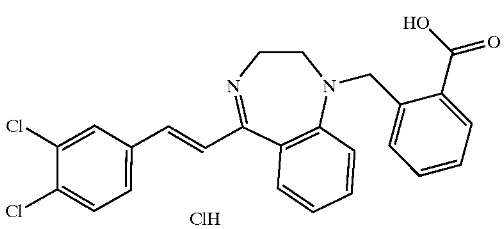 | (E)-2-[[5-(3,4-Dichlorostyryl)-2,3-dihydro-1H-1,4-benzodiazepin-1-yl]methyl]benzoic acid hydrochloride |
| 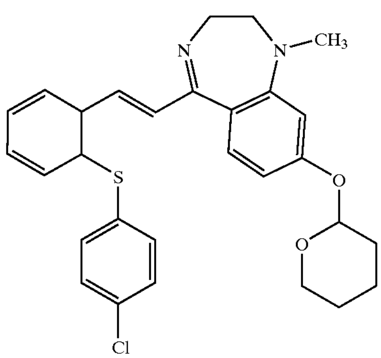 | (E)-5-[2-(4-Chlorophenylthio)styryl]-2,3-dihydro-8-(tetrahydro-2(RS)-pyranyloxy)-1-methyl-1H-1,4-benzodiazepine |
| 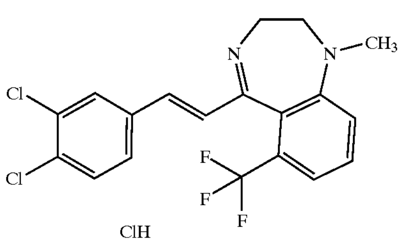 | (E)-5-(3,4-Dichlorostyryl)-6-(trifluoromethyl)-2,3-dihydro-1-methyl-1H-1,4-benzodiazepine dihydrochloride |

TABLE A-continued

| Structure | Names |
|---|---|
| 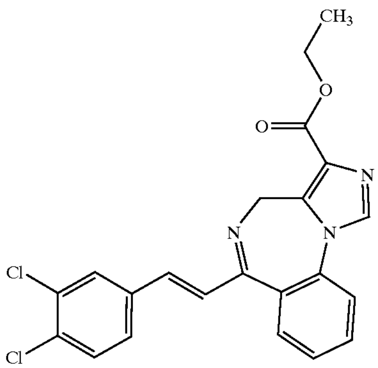 | Ethyl (E)-6-(3,4-dichlorostyryl)-4H-imidazo[1,5-a][1,4]benzo-diazepine-3-carboxylate |
| 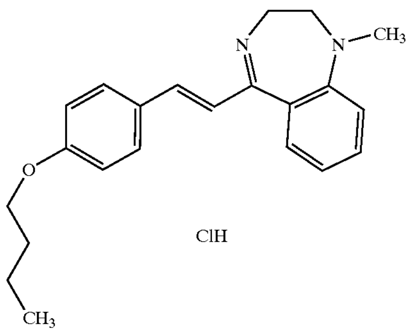 | (E)-5-(4-Butoxystyryl)-2,3-dihydro-1-methyl-1H-1,4-benzodiazepine dihydrochloride |
| 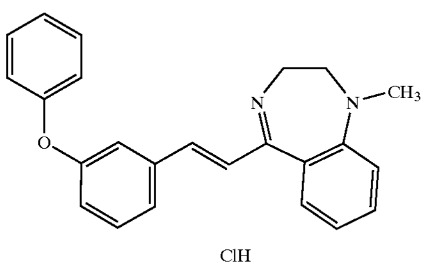 | (E)-2,3-Dihydro-1-methyl-5-(3-phenoxystyryl)-1H-1,4-benzo-diazepine dihydrochloride |
| 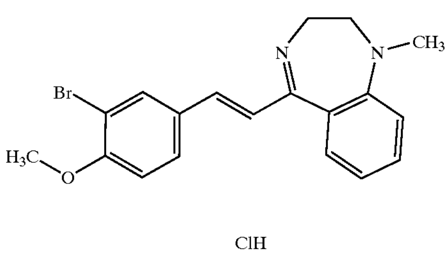 | (E)-5-(3-Bromo-4-methoxystyryl)-2,3-dihydro-1-methyl-1H-1,4-benzodiazepine dihydrochloride |
| 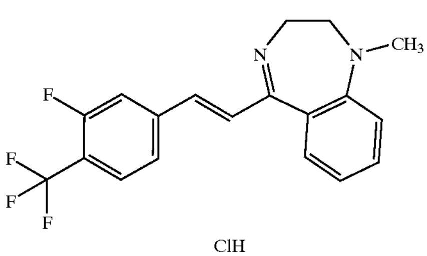 | (E)-5-[3-Fluoro-4-(trifluoromethyl)styryl]-2,3-dihydro-1-methyl-1H-benzo[e][1,4]diazepine dihydrochloride |

TABLE A-continued

| Structure | Names |
|---|---|
| 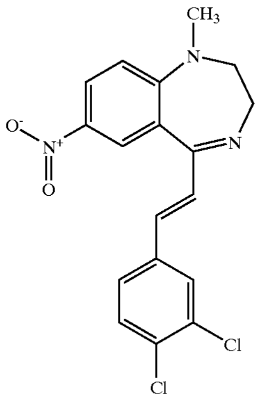 | (E)-5-(3,4-Dichlorostyryl)-2,3-dihydro-1-methyl-7-nitro-1H-1,4-benzodiazepine |
| 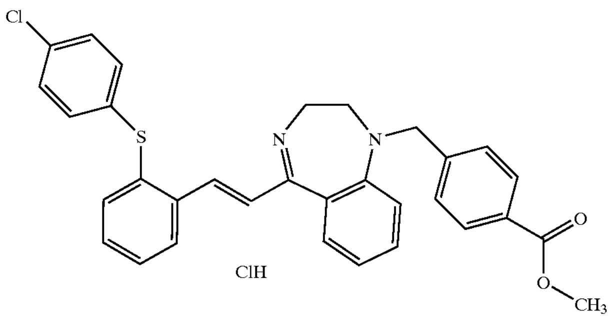 | Methyl (E)-4-[[5-[2-(4-Chlorophenylthio)styryl]-2,3-dihydro-1H-1,4-benzodiazepin-1-yl]methyl]benzoate hydrochloride |
| 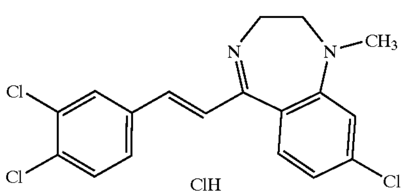 | (E)-8-Chloro-5-(3,4-dichlorostyryl)-2,3-dihydro-1-methyl-1H-1,4-benzodiazepine dihydrochloride |
| 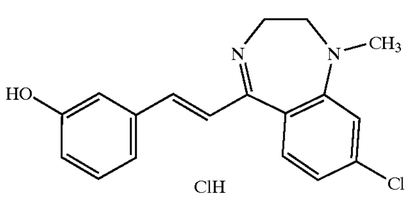 | (E)-3-[2-(8-Chloro-2,3-dihydro-1-methyl-1H-1,4-benzodiazepin-5-yl)vinyl]phenol hydrochloride |
| 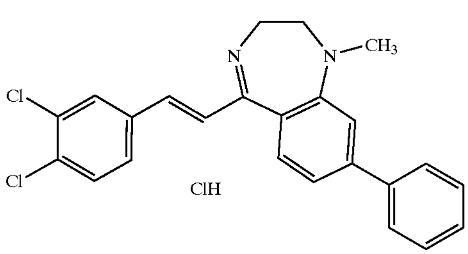 | (E)-5-(3,4-Dichlorostyryl)-2,3-dihydro-1-methyl-8-phenyl-1H-1,4-benzodiazepine dihydrochloride |
| 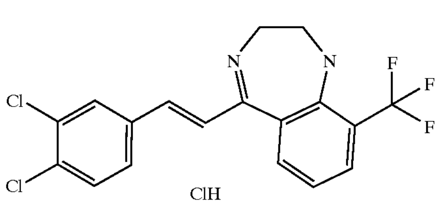 | (E)-5-(3,4-Dichlorostyryl)-9-(trifluoromethyl)-2,3-dihydro-1H-1,4-benzodiazepine dihydrochloride |

TABLE A-continued

| Structure | Names |
|---|---|
| 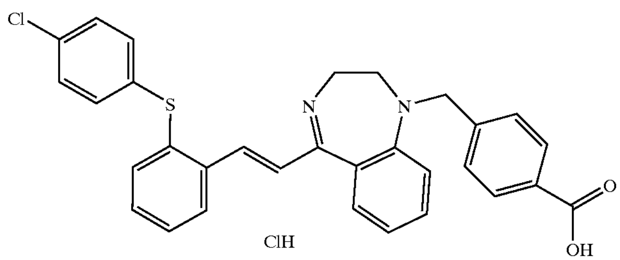 | (E)-4-[[5-[2-(4-Chlorophenylthio)styryl]-2,3-dihydro-1H-1,4-benzo-diazepin-1-yl]methyl]benzoic acid hydrochloride |
| 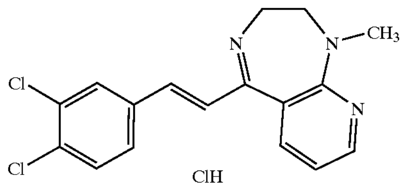 | (E)-5-(3,4-Dichlorostyryl)-2,3-dihydro-1-methyl-1H-pyridol[2,3-e][1,4]diazepine hydrochloride (1:3) |
| 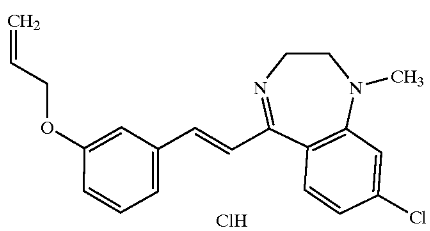 | (E)-5-(3-Allyloxystyryl)-8-chloro-2,3-dihydro-1-methyl-1H-1,4-benzo-diazepine dihydrochloride |
| 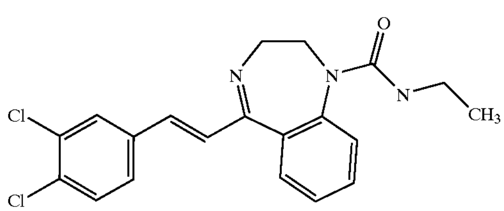 | (E)-5-(3,4-Dichlorostyryl)-N-ethyl-2,3-dihydro-1H-1,4-benzodiazepine-1-carboxamide |
| 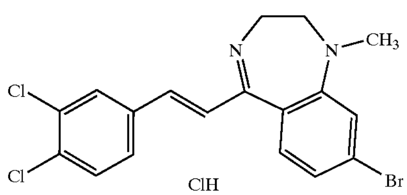 | (E)-8-Bromo-5-(3,4-dichlorostyryl)-2,3-dihydro-1-methyl-1H-1,4-benzodiazepine dihydrochloride |
| 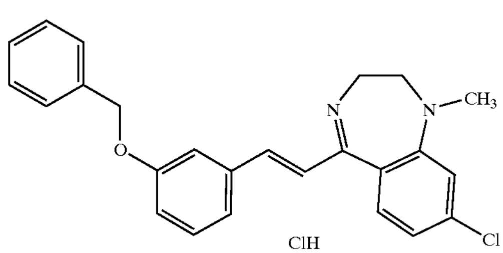 | (E)-5-(3-Benzyloxystyryl)-8-chloro-2,3-dihydro-1-methyl-1H-1,4-benzodiazepine dihydrochloride |
| 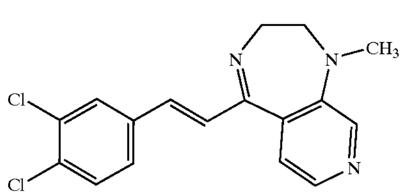 | (E)-5-(3,4-Dichlorostyryl)-2,3-dihydro-1-methyl-1H-pyrido[3,4-e][1,4]diazepine |

TABLE A-continued

| Structure | Names |
|---|---|
| 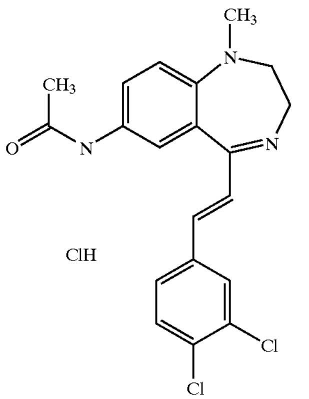 | (E)-5-(3,4-Dichlorostyryl)-2,3-dihydro-1-methyl-1H-1,4-benzodiazepin-7-acetamide hydrochloride |
| | (E)-5-(3,4-Dichlorostyryl)-2,3-dihydro-1-methyl-1H-pyrido[3,2-e][1,4]diazepine |
| 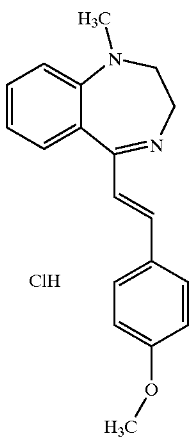 | (E)-2,3-Dihydro-5-(4-methoxystyryl)-1-methyl-1H-1,4-benzodiazepine hydrochloride |
| 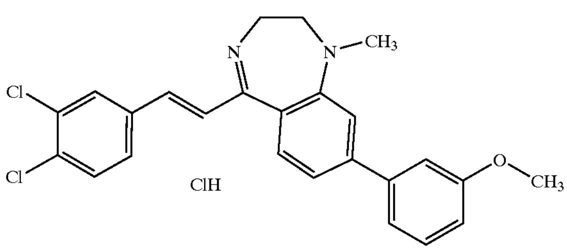 | (E)-5-(3,4-Dichlorostyryl)-2,3-dihydro-8-(3-methoxyphenyl)-1-methyl-1H-1,4-benzodiazepine dihydrochloride |
| 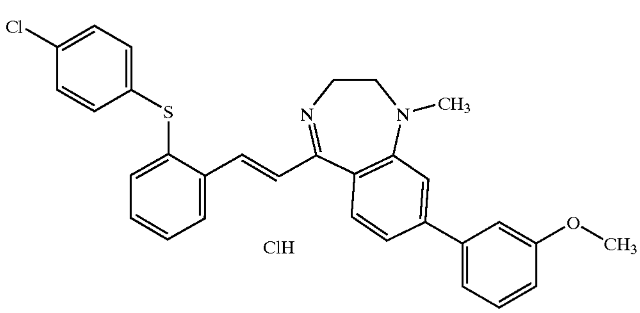 | (E)-5-[2-(4-Chlorophenylthio)styryl]-2,3-dihydro-8-(3-methoxyphenyl)-1-methyl-1H-1,4-benzodiazepine dihydrochloride |

TABLE A-continued

| Structure | Names |
|---|---|
| 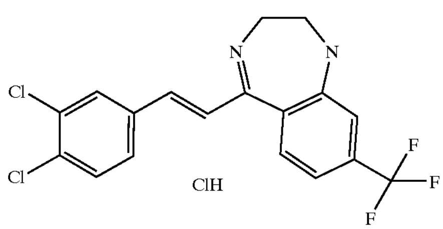 | (E)-5-(3,4-Dichlorostyryl)-8-(trifluoromethyl)-2,3-dihydro-1H-1,4-benzodiazepine hydrochloride |
| 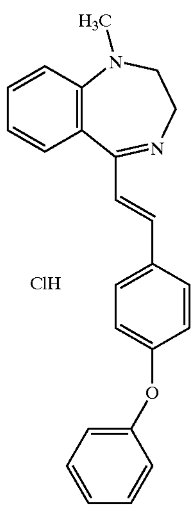 | (E)-2,3-Dihydro-1-methyl-5-(4-phenoxystyryl)-1H-1,4-benzodiazepine hydrochloride |
| 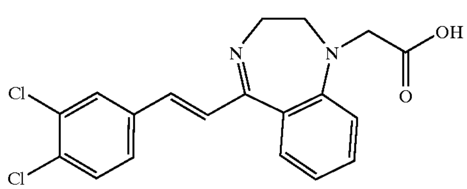 | (E)-5-(3,4-Dichlorostyryl)-2,3-dihydro-1H-1,4-benzodiazepine-1-acetic acid |
| 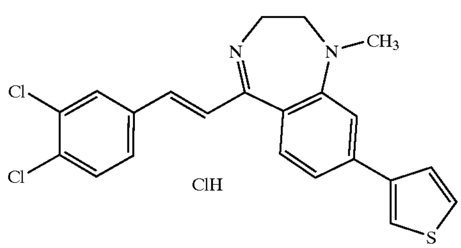 | (E)-5-(3,4-Dichlorostyryl)-2,3-dihydro-1-methyl-8-(3-thienyl)-1H-1,4-benzodiazepine dihydrochloride |
| 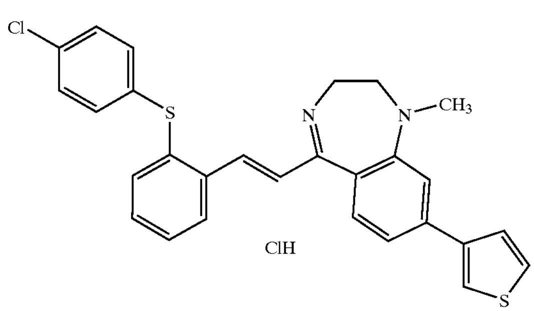 | (E)-5-[2-(4-Chlorophenylthio)styryl]-2,3-dihydro-1-methyl-8-(3-thienyl)-1H-1,4-benzodiazepine dihydrochloride |

TABLE A-continued

| Structure | Names |
|---|---|
| 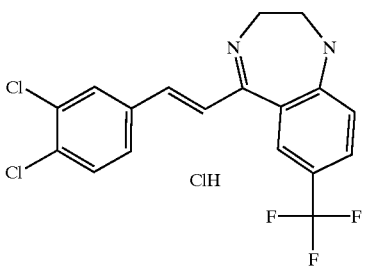 | (E)-5-(3,4-Dichlorostyryl)-7-(trifluoromethyl)-2,3-dihydro-1H-1,4-benzodiazepine hydrochloride |
| 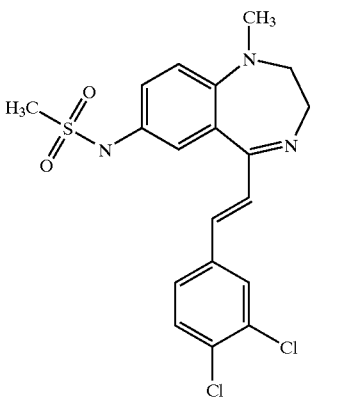 | (E)-N-[5-(3,4-Dichlorostyryl)-2,3-dihydro-1-methyl-1H-1,4-benzodiazepin-7-yl]methanesulfonamide |
| 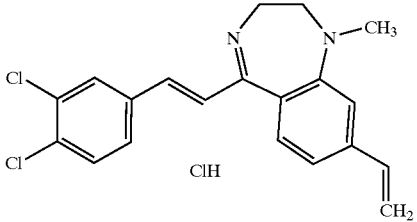 | 5-(3,4-Dichlorostyryl)-2,3-dihydro-1-methyl-8-vinyl-1H-1,4-benzodiazepine dihydrochloride |
| 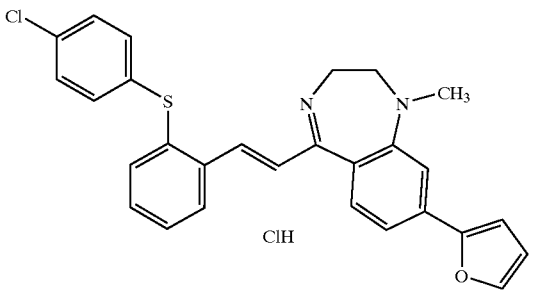 | (E)-5-[2-(4-Chlorophenylthio)styryl]-8-(2-furyl)-2,3-dihydro-1-methyl-1H-1,4-benzodiazepine dihydrochloride |
| 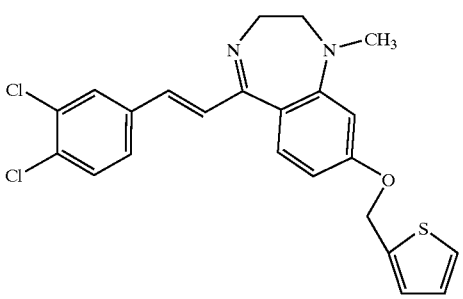 | (E)-5-(3,4-Dichlorostyryl)-2,3-dihydro-1-methyl-8-(2-thenyloxy)-1H-1,4-benzodiazepine |

TABLE A-continued

| Structure | Names |
| --- | --- |
| 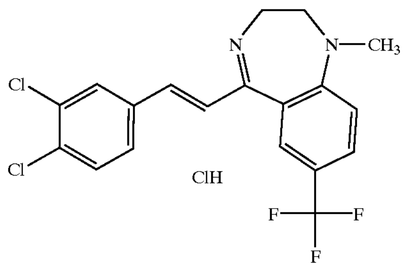 | (E)-5-(3,4-Dichlorostyryl)-7-(trifluoromethyl)-2,3-dihydro-1-methyl-1H-1,4-benzodiazepine hydrochloride |
| 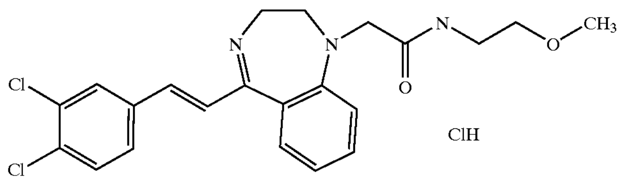 | (E)-5-(3,4-Dichlorostyryl)-2,3-dihydro-N-(2-methoxyethyl)-1H-1,4-benzodiazepin-1-acetamide dihydrochloride |
| 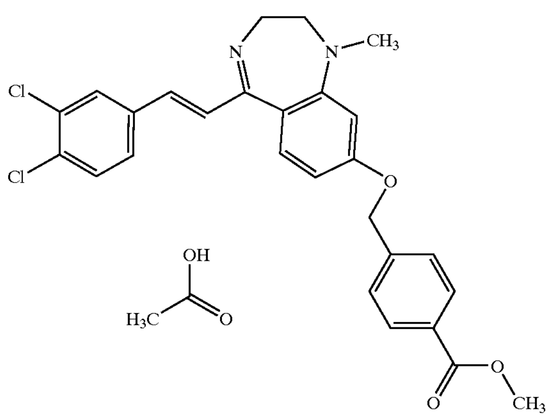 | Methyl (E)-4-[[5-(3,4-Dichlorostyryl)-2,3-dihydro-1-methyl-1H-1,4-benzodiazepin-8-yloxy]methyl]benzoate acetate (1:2) |
| 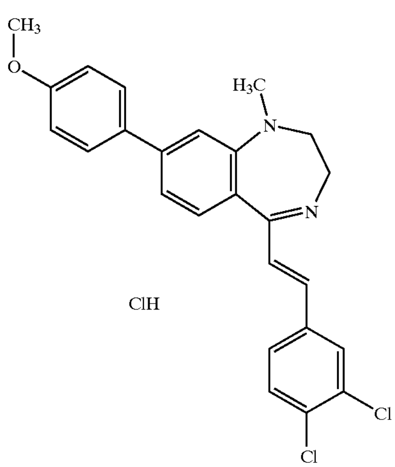 | (E)-5-(3,4-Dichlorostyryl)-2,3-dihydro-8-(4-methoxyphenyl)-1-methyl-1H-1,4-benzodiazepine |

TABLE A-continued

| Structure | Names |
|---|---|
| 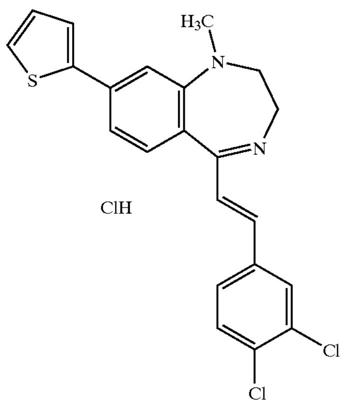 | (E)-5-(3,4-Dichlorostyryl)-2,3-dihydro-1-methyl-8-(2-thienyl)-1H-1,4-benzodiazepine hydrochloride |
| 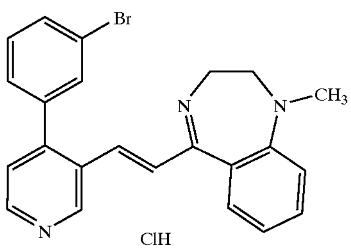 | (E)-5-[2-[4-(3-Bromophenyl)-3-pyridyl]vinyl]-2,3-dihydro-1-methyl-1H-1,4-benzodiazepine dihydrochloride |
| 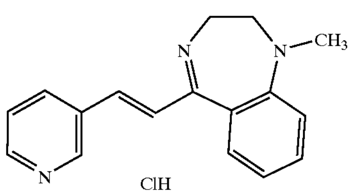 | (E)-2,3-Dihydro-1-methyl-5-1[2-(3-pyridyl)vinyl]-1H-1,4-benzodiazepine dihydrochloride |
| 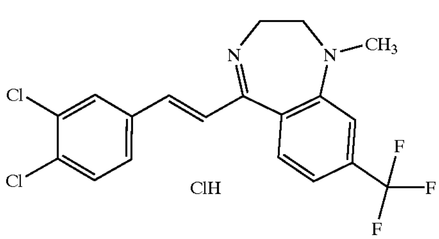 | (E)-5-(3,4-Dichlorostyryl)-8-(trifluoromethyl)-2,3-dihydro-1-methyl-1H-1,4-benzodiazepine hydrochloride |
| 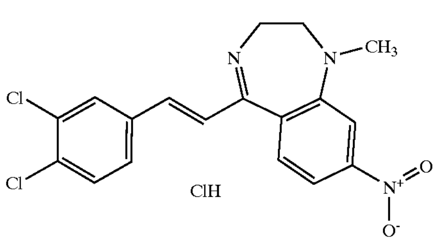 | (E)-5-(3,4-Dichlorostyryl)-2,3-dihydro-1-methyl-8-nitro-1H-1,4-benzodiazepine hydrochloride |

TABLE A-continued

| Structure | Names |
|---|---|
| 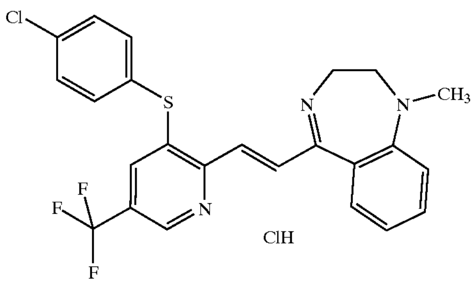 | (E)-5-[2-[3-(4-Chlorophenylthio)-5-(trifluoromethyl)-2-pyridyl]vinyl]-2,3-dihydro-1-methyl-1,4-benzodiazepine dihydrochloride |
| 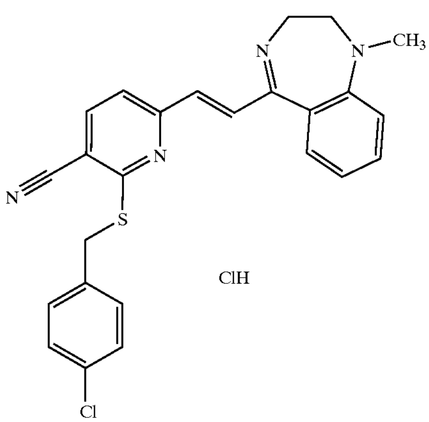 | (E)-2-(4-Chlorobenzylthio)-6-[2-(2,3-dihydro-1-methyl-1H-1,4-benzocliazepin-5-yl)vinyl]-3-pyridinecarbonitrile dihydrochloride |
| 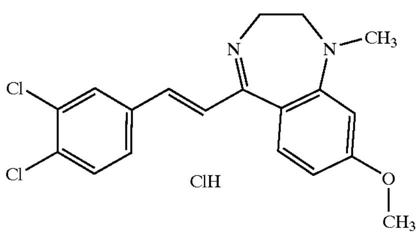 | (E)-5-(3,4-Dichlorostyryl)-2,3-dihydro-8-methoxy-1-methyl-1H-1,4-benzodiazepine hydrochloride |
| 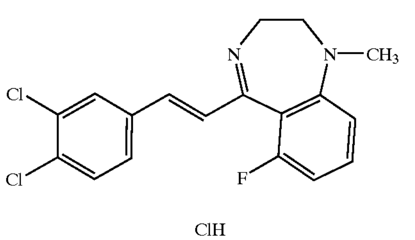 | (E)-5-(3,4-Dichlorostyryl)-6-fluoro-2,3-dihydro-1-methyl-1H-1,4-benzodiazepine hydrochloride |
| 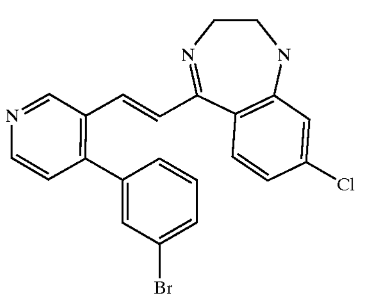 | (E)-5-[2-[4-(3-Bromophenyl)-3-pyridyl]vinyl]-8-chloro-2,3-dihydro-1H-1,4-benzodiazepine |

TABLE A-continued

| Structure | Names |
|---|---|
| 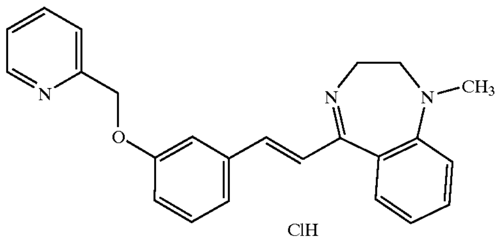 | (E)-2,3-Dihydro-1-methyl-5-[3-[(2-pyridyl)methoxy]styryl]-1H-1,4-benzodiazepine dihydrochloride |
| 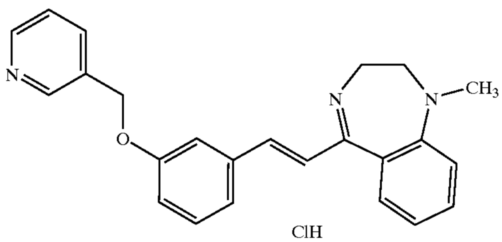 | (E)-2,3-Dihydro-1-methyl-5-[3-[(3-pyridyl)methoxy]styryl]-1H-1,4-benzodiazepine dihydrochloride |
| 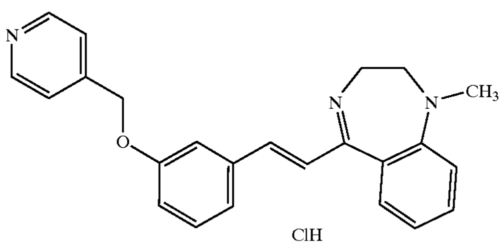 | (E)-2,3-Dihydro-1-methyl-5-[3-[(4-pyridyl)methoxy]styryl]-1H-1,4-benzodiazepine dihydrochloride |
| 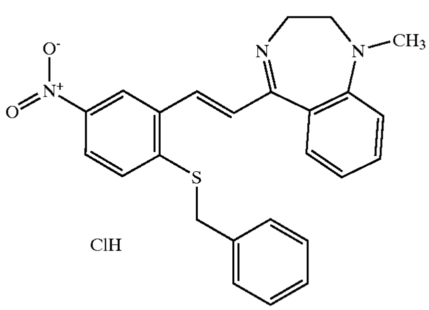 | (E)-5-(2-Benzylthio-5-nitrostyryl)-2,3-dihydro-1-methyl-1H-1,4-benzodiazepine dihydrochloride |
| 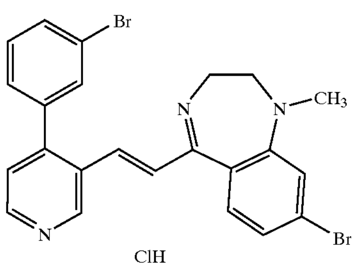 | (E)-8-Bromo-5-[2-[4-(3-bromophenyl)-3-pyridyl]vinyl]-2,3-dihydro-1-methyl-1H-1,4-benzodiazepine dihydrochloride |

TABLE A-continued

| Structure | Names |
|---|---|
| 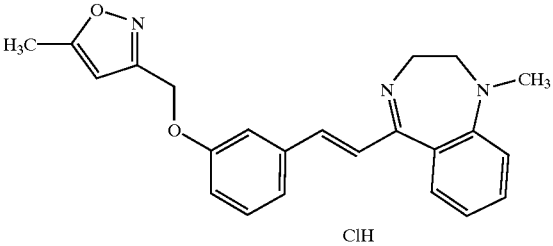 | (E)-2,3-Dihydro-1-methyl-5-[3-[(5-methyl-3-isoxazol-3-yl)methoxy]styryl]-1H-1,4-benzodiazepine dihydrochloride |
| 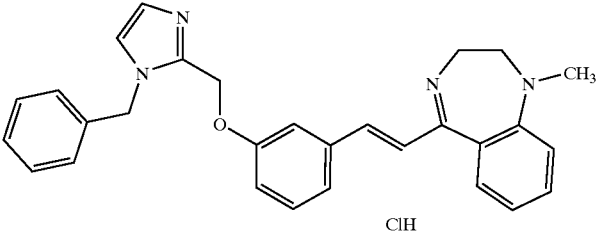 | (E)-5-[3-[(1-Benzyl-1H-imidazol-2-yl)methoxy]styryl]-2,3-dihydro-1-methyl-1H-1,4-benzodiazepine dihydrochloride |
| 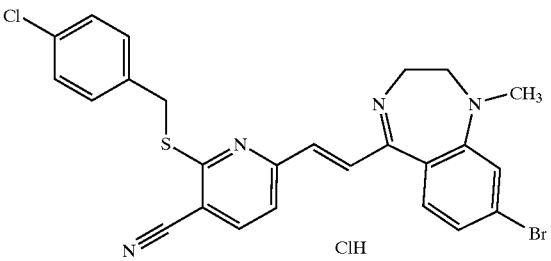 | (E)-6-[2-(8-Bromo-2,3-dihydro-1-methyl-1H-1,4-benzodiazepin-5-yl)vinyl]-2-(4-chlorobenzylthio)-3-pyridinecarbonitrile dihydrochloride |
| 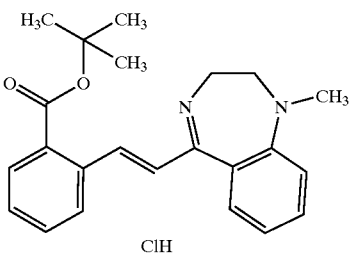 | tert-Butyl (E)-2-[2-(2,3-dihydro-1-methyl-1H-1,4-benzodiazepin-5-yl)vinyl]benzoate dihydrochloride |
| 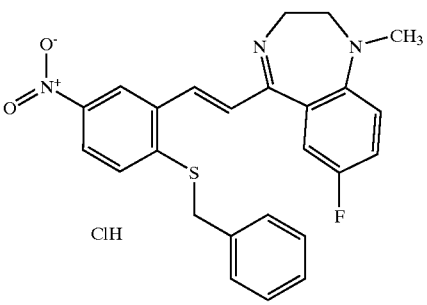 | (E)-5-(2-Benzylthio-5-nitrostyryl)-7-fluoro-2,3-dihydro-1-methyl-1H-1,4-benzodiazepine dihydrochloride |

TABLE A-continued

| Structure | Names |
|---|---|
| 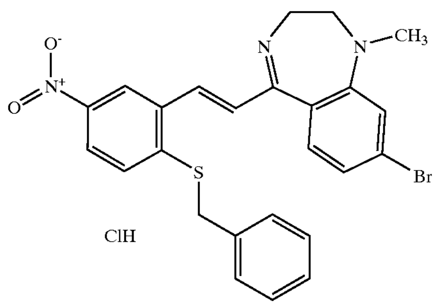 | (E)-5-(2-Benzylthio-5-nitrostyryl)-8-bromo-2,3-dihydro-1-methyl-1H-1,4-benzodiazepine dihydrochloride |
| 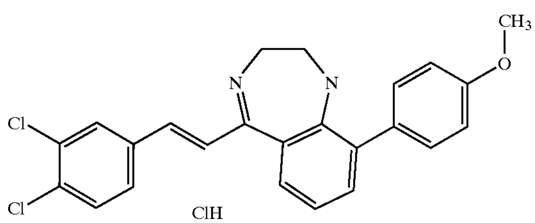 | (E)-5-(3,4-Dichlorostyryl)-2,3-dihydro-9-(4-methoxyphenyl)-1H-1,4-benzodiazepine hydrochloride |
| 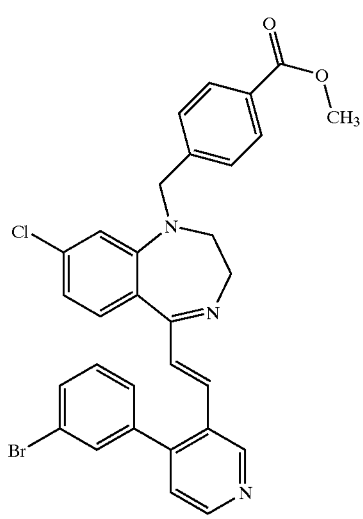 | Methyl (E)-4-[[5-[2-[4-(3-bromophenyl)-3-pyridyl]vinyl]-8-chloro-2,3-dihydro-1,4-benzodiazepin-1-yl]methyl]benzoate |
| 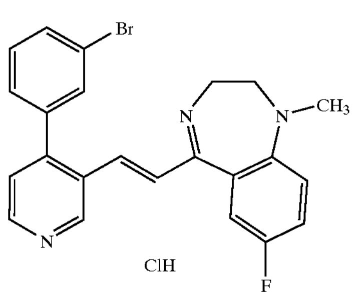 | (E)-5-[4-(3-Bromophenyl)-3-pyridyl]-7-fluoro-2,3-dihydro-1-methyl-1H-1,4-benzodiazepine dihydrochloride |

TABLE A-continued

| Structure | Names |
|---|---|
| 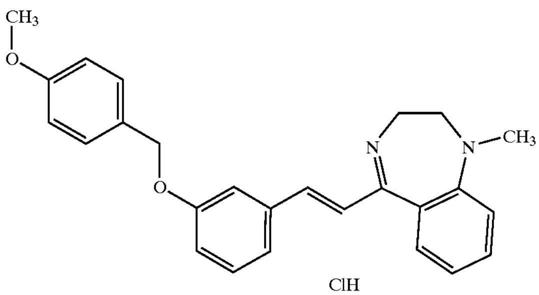 | (E)-5-[2,3-Dihydro-3-(4-methoxybenzyloxy)styryl]-1-methyl-1H-1,4-benzodiazepine dihydrochloride |
| 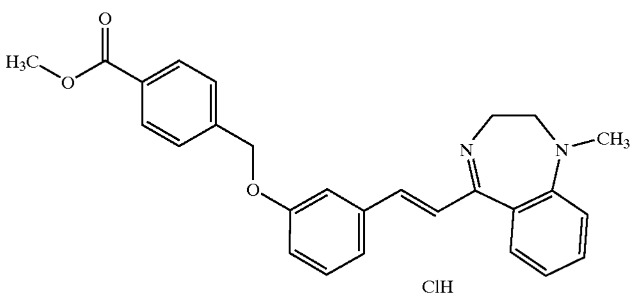 | Methyl (E)-4-[[3-[2-(2,3-dihydro-1-methyl-1H-1,4-benzodiazepin-5-yl)vinyl]phenoxy]methyl]benzoate dihydrochloride |
| 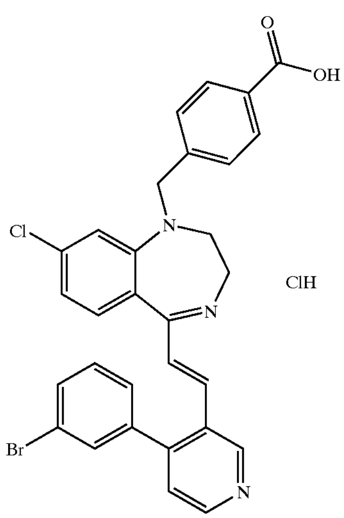 | (E)-4-[[5-[2-[4-(3-Bromophenyl)-3-pyridyl]vinyl]-8-chloro-2,3-dihydro-1,4-benzodiazepin-1-yl]methyl]benzoic acid hydrochloride |
| 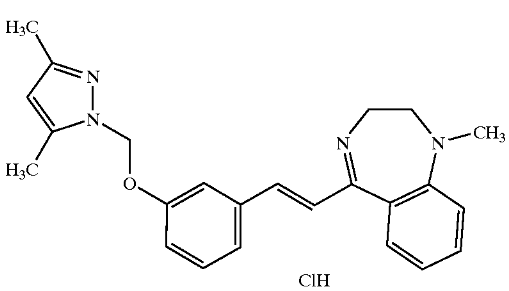 | (E)-2,3-Dihydro-1-methyl-5-[3-[(3,5-dimethyl-1-pyrazolyl)methoxy]styryl]-1H-1,4-benzodiazepine dihydrochloride |

TABLE A-continued

| Structure | Names |
|---|---|
| 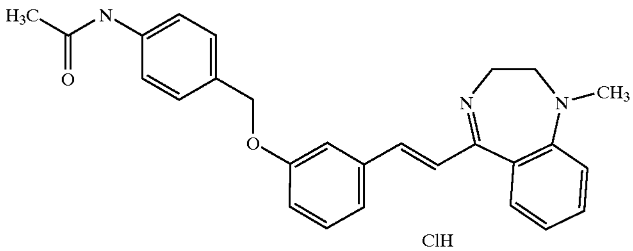 | (E)-4'-[[3-[2-(2,3-Dihydro-1-methyl-1H-1,4-benzodiazepin-5-yl)vinyl]phenoxy]methyl]acetanilide hydrochloride |
| 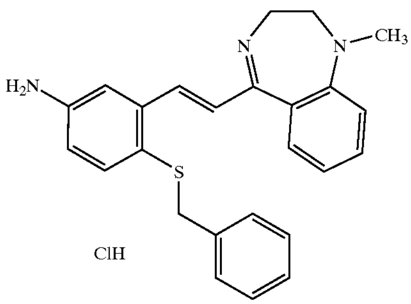 | (E)-4-Benzylthio-3-[2-(2,3-dihydro-1-methyl-1H-1,4-benzodiazepin-5-yl)vinyl]aniline hydrochloride |
| 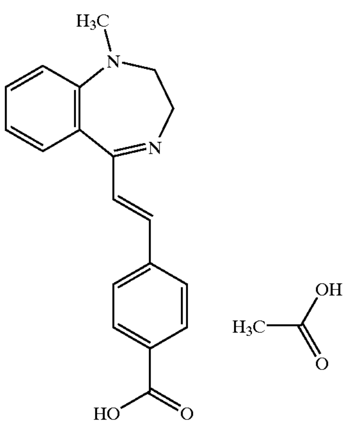 | (E)-4-[2-(2,3-Dihydro-1-methyl-1H-1,4-benzodiazepin-5-yl)vinyl]benzoic acid acetate (1:1) |
| 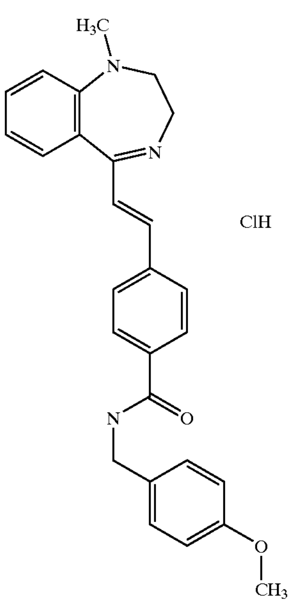 | (E)-4-[2-(2,3-Dihydro-1-methyl-1H-1,4-benzodiazepin-5-yl)vinyl]-N-(4-methoxybenzyl)benzamide hydrochloride |

TABLE A-continued
| Structure | Names |
|---|---|
| 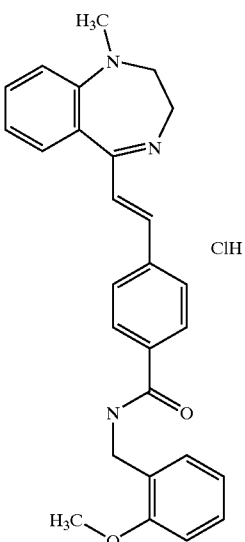 | (E)-4-[2-(2,3-Dihydro-1-methyl-1H-1,4-benzodiazepin-5-yl)vinyl]-N-(2-methoxybenzyl)benzamide hydrochloride |
| 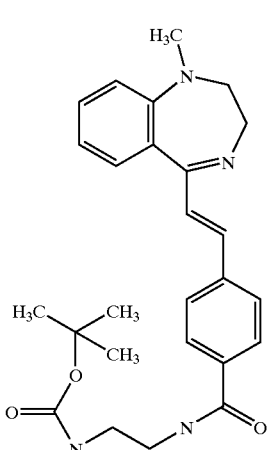 | tert-Butyl (E)-[2-[4-[2-(2,3-dihydro-1-methyl-1H-1,4-benzodiazepin-5-yl)-vinyl]-benzamido]ethyl)]carbamate |
| 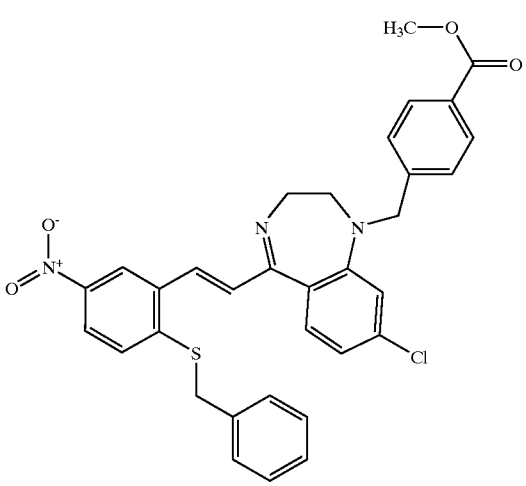 | Methyl (E)-4-[[5-(2-benzylthio-5-nitrostyryl)-8-chloro-2,3-dihydro-1,4-benzodiazepin-1-yl]methyl]benzoate |

TABLE A-continued

| Structure | Names |
|---|---|
| 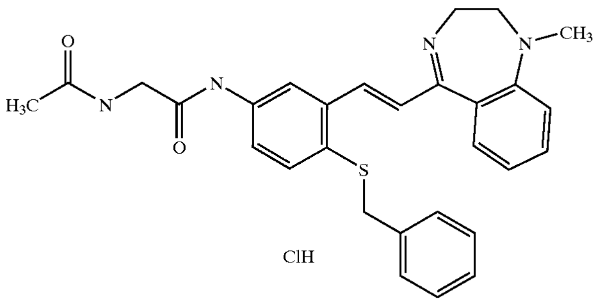 | (E)-2-Acetamido-4'-benzylthio-3'-[2-(2,3-dihydro-1-methyl-1H-1,4-benzodiazepin-5-yl)vinyl]acetanilide dihydrochloride |
| 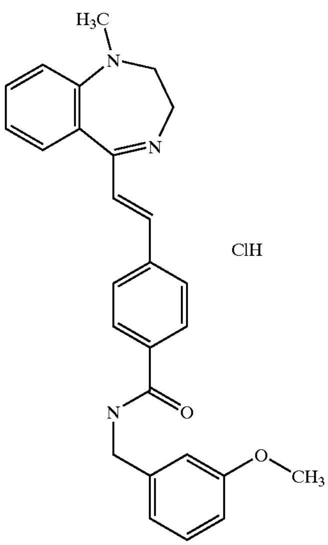 | (E)-4-[2-(2,3-Dihydro-1-methyl-1H-1,4-benzodiazepin-5-yl)vinyl]-N-(3-methoxybenzyl)benzamide hydrochloride |
| 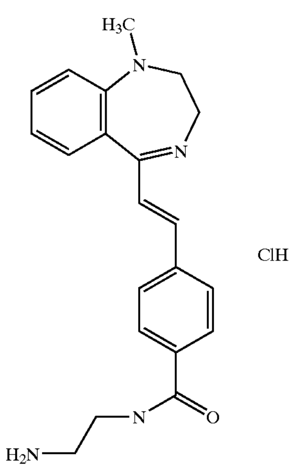 | (E)-N-(2-Aminoethyl)-4-[2-(2,3-dihydro-1-methyl-1H-1,4-benzodiazepin-5-yl)vinyl]benzamide hydrochloride |

TABLE A-continued

| Structure | Names |
|---|---|
| 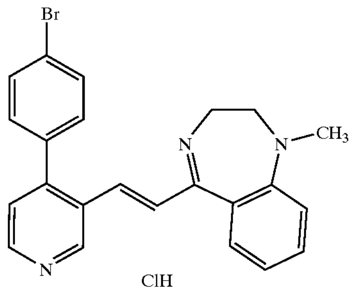 | (E)-5-[2-[4-(4-Bromophenyl)-3-pyridyl]vinyl]-2,3-dihydro-1-methyl-1H-1,4-benzodiazepine dihydrochloride |
| 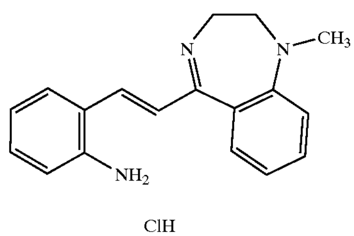 | (E)-2-[2-(2,3-Dihydro-1-methyl-1H-1,4-benzodiazepin-5-yl)vinyl]aniline hydrochloride |
| 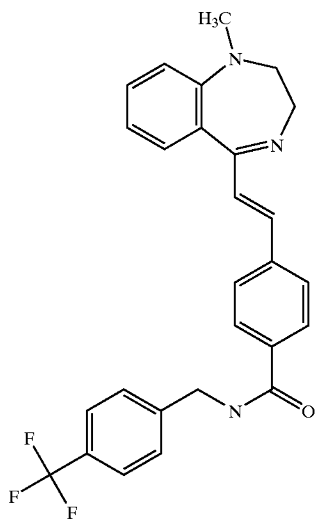 | (E)-N-[4-(Trifluoromethyl)benzyl]-4-[2-(2,3-dihydro-1-methyl-1H-1,4-benzodiazepin-5-yl)vinyl]benzamide |
| 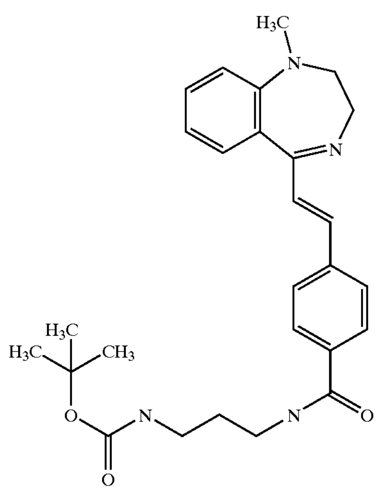 | tert-Butyl (E)-[3-[4-[2-(2,3-dihydro-1-methyl-1H-1,4-benzodiazepin-5-yl)vinyl]benzamido]propyl]carbamate |

TABLE A-continued
| Structure | Names |
|---|---|
| 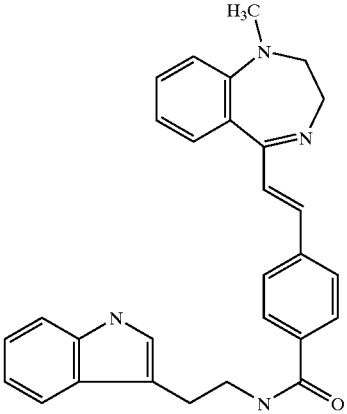 | (E)-4-[2-(2,3-Dihydro-1-methyl-1H-1,4-benzodiazepin-5-yl)vinyl]-N-[2-(1H-indol-3-yl)ethyl]benzamide |
| 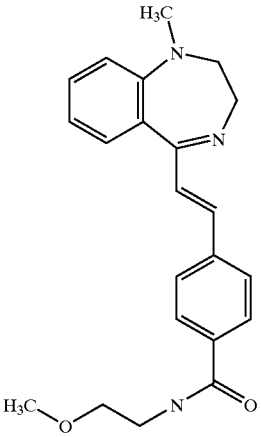 | (E)-4-[2-(2,3-Dihydro-1-methyl-1H-1,4-benzodiazepin-5-yl)vinyl]-N-(2-methoxyethyl)benzamide |
| 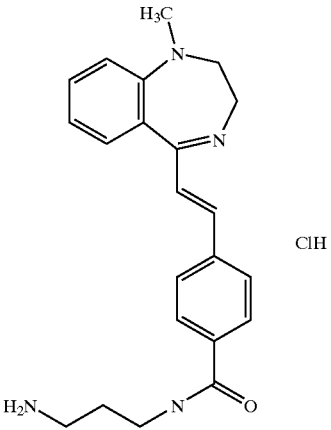 | (E)-N-(3-Aminopropyl)-4-[2-(2,3-dihydro-1-methyl-1H-1,4-benzodiazepin-5-yl)vinyl]benzamide hydrochloride |

TABLE A-continued

| Structure | Names |
|---|---|
| 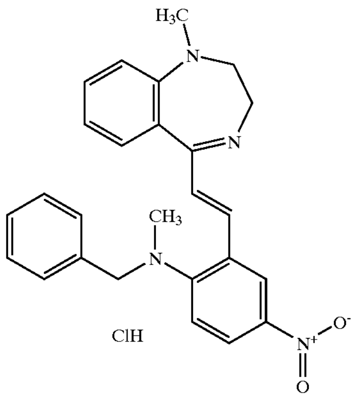 | (E)-2-[2-(2,3-Dihydro-1-methyl-1H-1,4-benzodiazepin-5-yl)vinyl]-N-methyl-4-nitroaniline dihydrochloride |
| 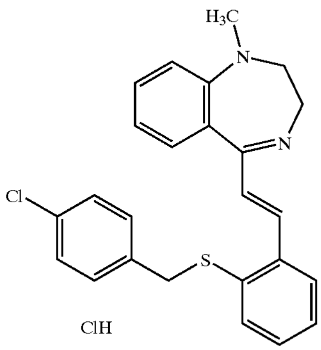 | (E)-5-[2-(4-Chlorobenzylthio)styryl]-2,3-dihydro-1-methyl-1H-1,4-benzodiazepine dihydrochloride |
| 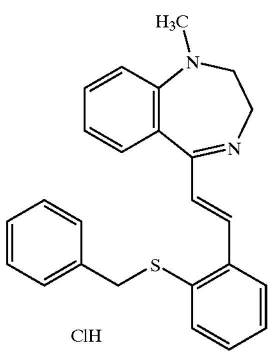 | (E)-5-(2-Benzylthiostyryl)-2,3-dihydro-1-methyl-1H-1,4-benzodiazepine dihydrochloride |
| 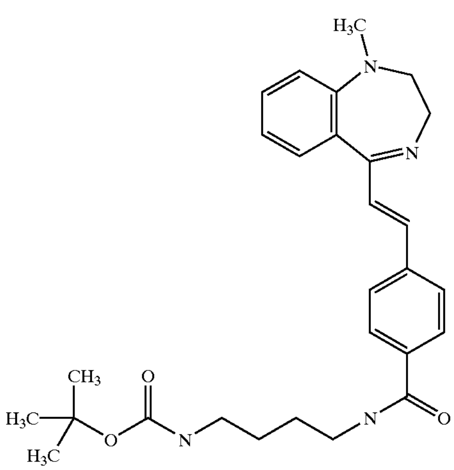 | tert-Butyl (E)-(4-[4-[2-(2,3-dihydro-1-methyl-1H-1,4-benzodiazepin-5-yl)vinyl]benzamido]butyl)carbamate |

TABLE A-continued
| Structure | Names |
|---|---|
| 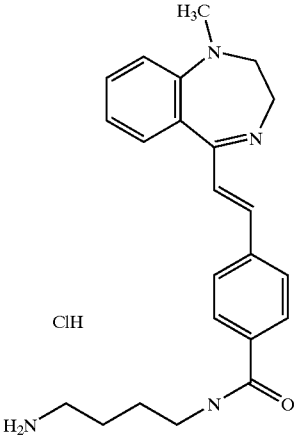 | (E)-N-(4-Aminobutyl)-4-[2-(2,3-dihydro-1-methyl-1H-1,4-benzodiazepin-5-yl)vinyl]benzamide hydrochloride |
| 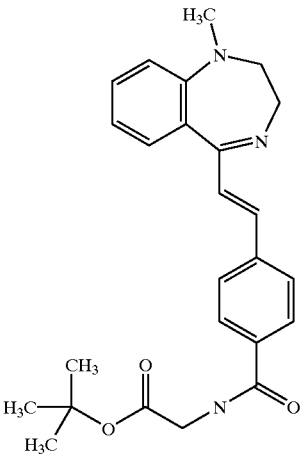 | tert-Butyl (E)-[4-[2-(2,3-dihydro-1-methyl-in-1,4-benzodiazepin-5-yl)vinyl]benzamido]acetate |
| 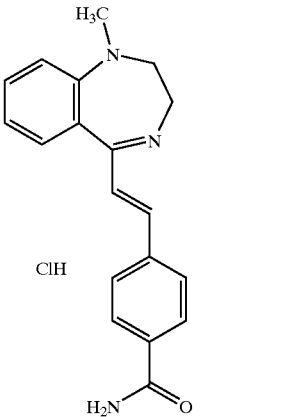 | (E)-4-[2-(2,3-Dihydro-1-methyl-1H-1,4-benzodiazepin-5-yl)vinyl]benzamide hydrochloride |

TABLE A-continued
| Structure | Names |
| --- | --- |
| 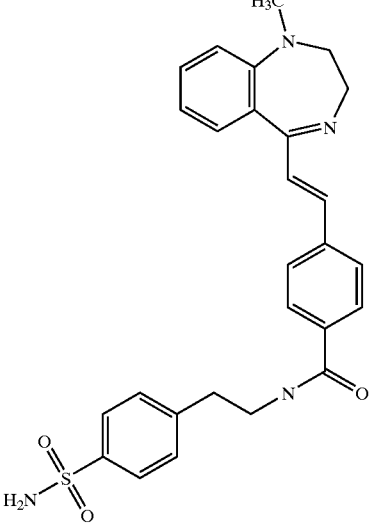 | (E)-4-[2-(2,3-Dihydro-1-methyl-1H-1,4-benzodiazepin-5-yl)vinyl]-N-[2-(4-sulfamoylphenyl)ethyl]benzamide |
| 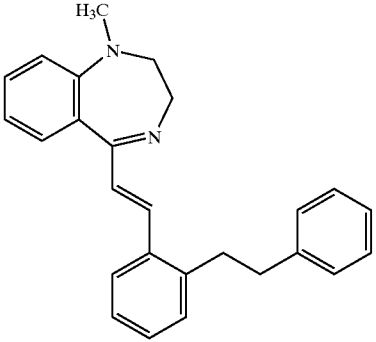 | (E)-2,3-Dihydro-1-methyl-5-[2-(2-phenylethyl)styryl]-1H-1,4-benzodiazepine |
| 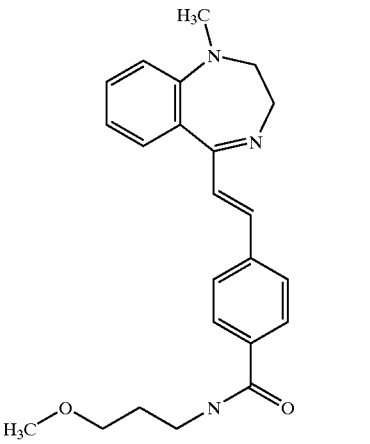 | (E)-4-[2-(2,3-Dihydro-1-methyl-1H-1,4-benzodiazepin-5-yl)vinyl]-N-(3-methoxypropyl)benzamide |

TABLE A-continued

| Structure | Names |
|---|---|
| 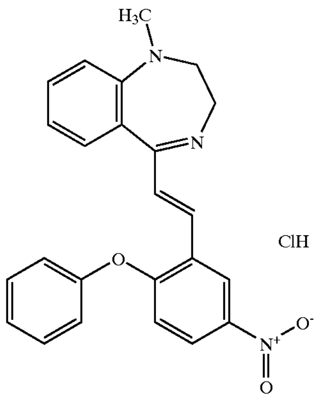 | (E)-2,3-Dihydro-1-methyl-5-(5-nitro-2-phenoxystyryl)-1H-1,4-benzodiazepine dihydrochloride |
| 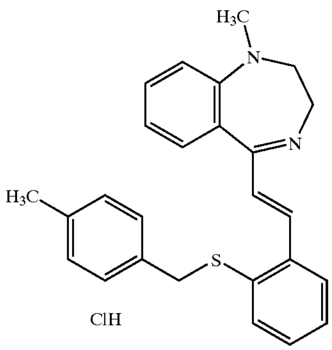 | (E)-2,3-Dihydro-1-methyl-5-[2-(4-methylbenzylthio)styryl]-1H-1,4-benzodiazepine dihydrochloride |
| 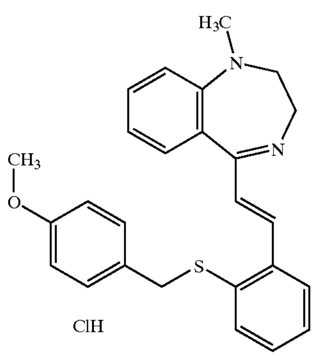 | (E)-2,3-Dihydro-5-[2-(4-methoxybenzylthio)styryl]-1-methyl-1H-1,4-benzodiazepine dihydrochloride |
| 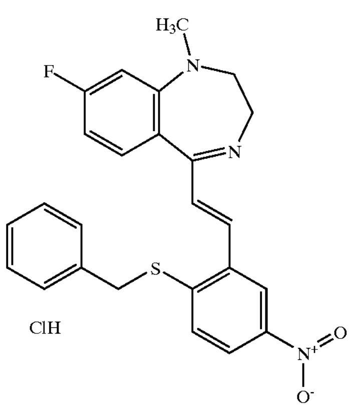 | (E)-5-(2-Benzylthio-5-nitrostyryl)-8-fluoro-2,3-dihydro-1-methyl-1H-1,4-benzodiazepine hydrochloride |

TABLE A-continued

| Structure | Names |
|---|---|
| 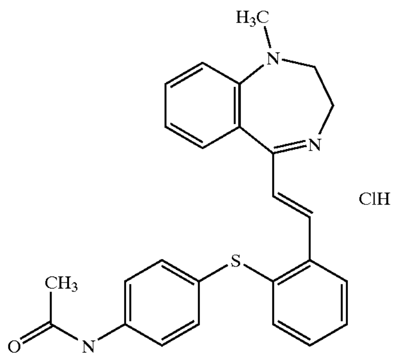 | (E)-4'-[2-[2-(2,3-Dihydro-1-methyl-1H-1,4-benzodiazepin-5-yl)vinyl]phenylthio]acetanilide hydrochloride |
| 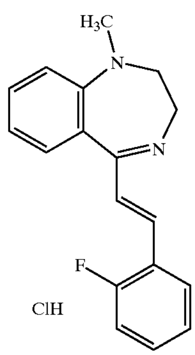 | (E)-5-(2-Fluorostyryl)-2,3-dihydro-1-methyl-1H-1,4-benzodiazepine dihydrochloride |
| 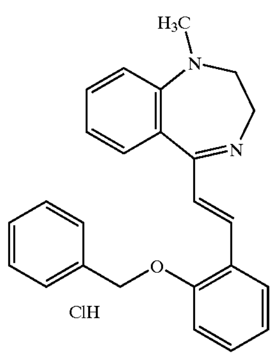 | (E)-5-(2-Benzyloxystyryl)-2,3-dihydro-1-methyl-1H-1,4-benzodiazepine dihydrochloride |
| 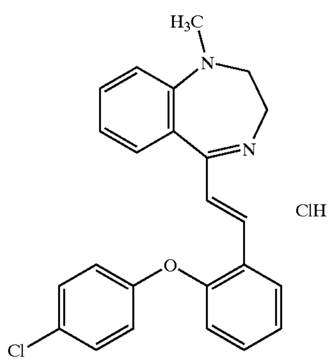 | (E)-5-[2-(4-Chlorophenoxy)styryl]-2,3-dihydro-1-methyl-1H-1,4-benzodiazepine dihydrochloride |

TABLE A-continued

| Structure | Names |
|---|---|
| 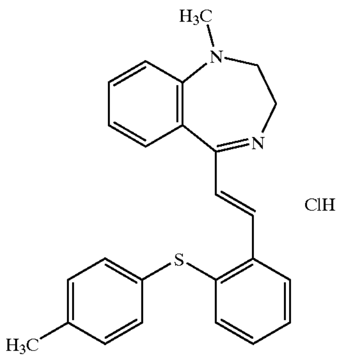 | (E)-2,3-Dihydro-1-methyl-5-(2-p-tolylthiostyryl)-1H-1,4-benzodiazepine dihydrochloride |
| 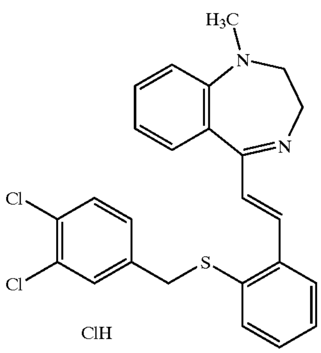 | (E)-5-[2-(3,4-Dichlorobenzylthio)styryl]-2,3-dihydro-1-methyl-1H-1,4-benzodiazepine dihydrochloride |
| 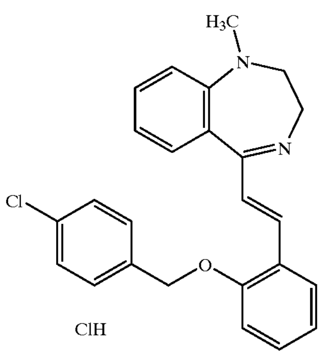 | (E)-5-[2-(4-Chlorobenzyloxy)styryl]-2,3-dihydro-1-methyl-1H-1,4-benzodiazepine dihydrochloride |
| 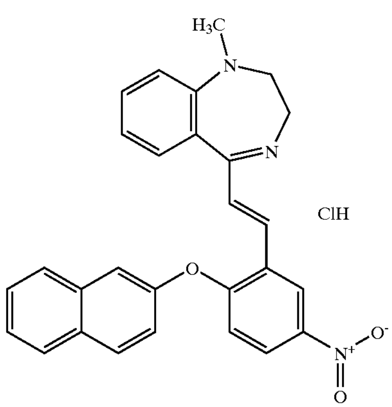 | (E)-2,3-Dihydro-1-methyl-5-[2-(2-naphthyloxy)-5-nitrostyryl]-1H-1,4-benzodiazepine dihydrochloride |

TABLE A-continued

| Structure | Names |
|---|---|
| 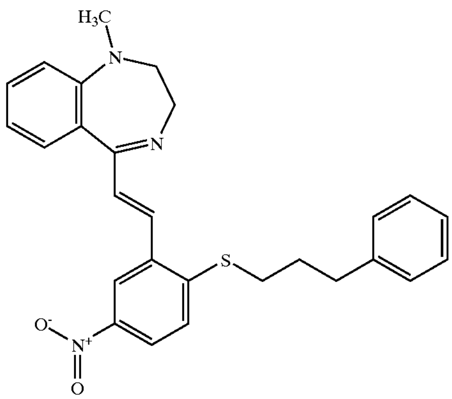 | (E)-2,3-Dihydro-1-methyl-5-[5-nitro-2-(3-phenylpropylthio)styryl]-1H-1,4-benzodiazepine |
| 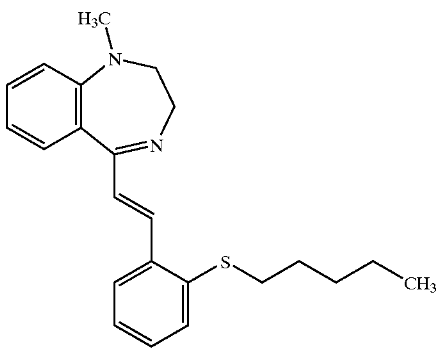 | (E)-2,3-Dihydro-1-methyl-5-(2-pentylthiostyryl)-1H-1,4-benzodiazepine |
| 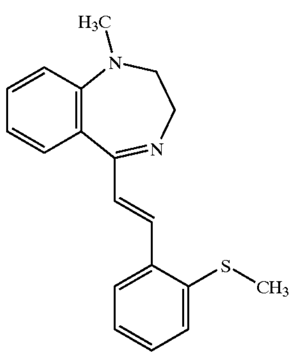 | (E)-2,3-Dihydro-1-methyl-5-(2-methylthiostyryl)-1H-1,4-benzodiazepine |
| 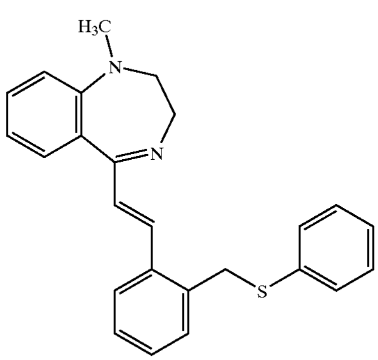 | (E)-2,3-Dihydro-1-methyl-5-[2-(phenylthiomethyl)styryl]-1H-1,4-benzodiazepine |

TABLE A-continued

| Structure | Names |
|---|---|
| | (E)-3-[2-(2,3-Dihydro-1-methyl-1H-1,4-benzodiazepin-5-yl)vinyl]-4-(3-phenylpropylthio)aniline hydrochloride |
| 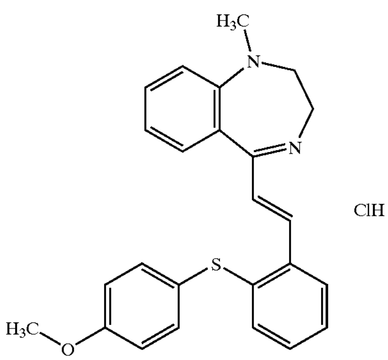 | (E)-2,3-Dihydro-5-[2-(4-methoxyphenylthio)styryl]-1-methyl-1H-1,4-benzodiazepine dihydrochloride |
| 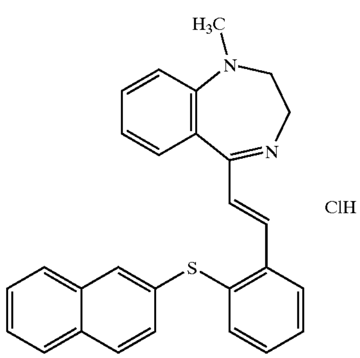 | (E)-2,3-Dihydro-1-methyl-5-[2-(2-naphthylthio)styryl]-1H-1,4-benzodiazepine dihydrochloride |
| 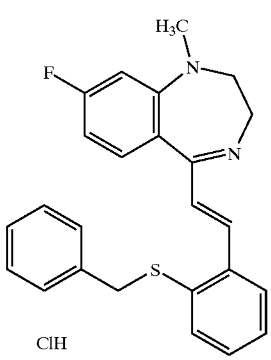 | (E)-5-(2-Benzylthiostyryl)-8-fluoro-2,3-dihydro-1-methyl-1H-1,4-benzodiazepine dihydrochloride |

TABLE A-continued

| Structure | Names |
|---|---|
| 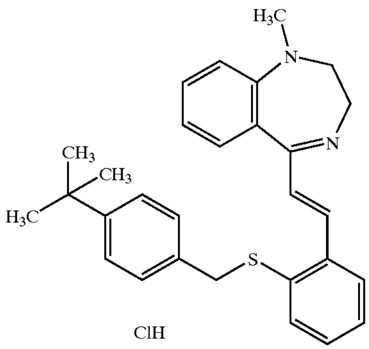 | (E)-5-[2-(4-tert-Butyl-benzylthio)styryl]-2,3-dihydro-1-methyl-1H-1,4-benzodiazepine dihydrochloride |
| 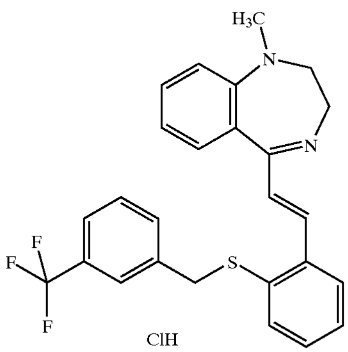 | (E)-5-[2-[3-(Trifluoromethyl)benzylthio]styryl]-2,3-dihydro-1-methyl-1H-1,4-benzodiazepine dihydrochloride |
| 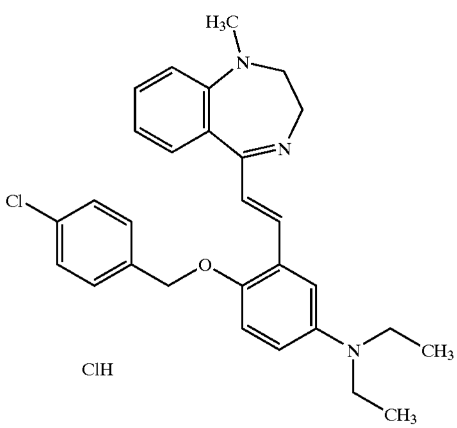 | (E)-4-(4-Chlorobenzyloxy)-3-[2-(2,3-dihydro-1-methyl-1H-1,4-benzodiazepin-5-yl)vinyl]-N,N-diethylaniline dihydrochloride |
| | (E)-2,3-Dihydro-1-methyl-5-[2-[(2-naphthyl)methoxy]styryl]-1H-1,4-benzodiazepine dihydrochloride |

TABLE A-continued

| Structure | Names |
|---|---|
| 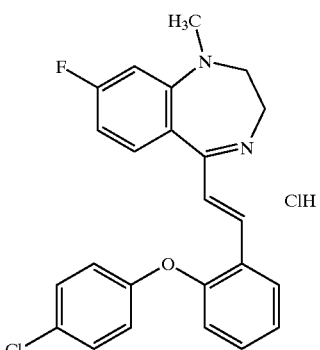 | (E)-5-[2-(4-Chlorophenoxy)styryl]-8-fluoro-2,3-dihydro-1-methyl-1H-1,4-benzodiazepine dihydrochloride |
| 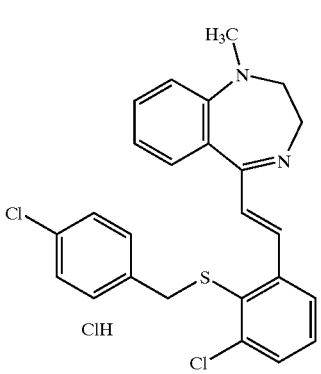 | (E)-5-[3-Chloro-2-(4-chlorobenzylthio)styryl]-2,3-dihydro-1-methyl-1H-1,4-benzodiazepine dihydrochloride |
| 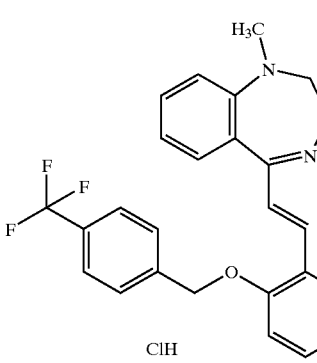 | (E)-5-[2-[4-(Trifluoromethyl)benzyloxy]styryl]-2,3-dihydro-1-methyl-1H-1,4-benzodiazepine dihydrochloride |
| 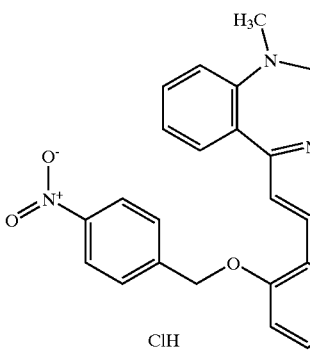 | (E)-2,3-Dihydro-1-methyl-5-[2-(4-nitrobenzyloxy)styryl]-1H-1,4-benzodiazepine dihydrochloride |

TABLE A-continued

| Structure | Names |
|---|---|
| 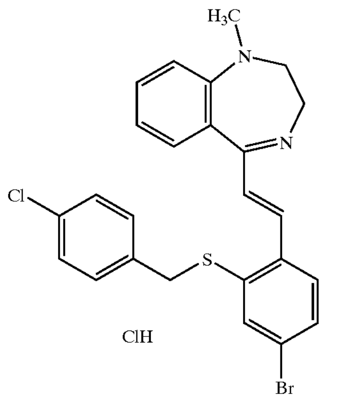 | (E)-5-[4-Bromo-2-(4-chlorobenzylthio)styryl]-2,3-dihydro-1-methyl-1H-1,4-benzodiazepine dihydrochloride |
| 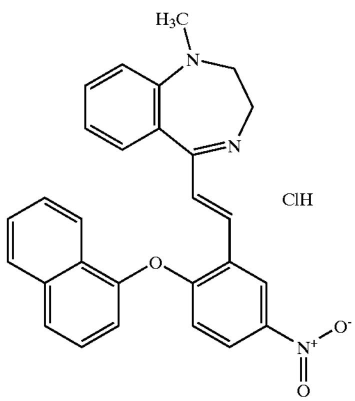 | (E)-2,3-Dihydro-1-methyl-5-[2-(1-naphthyloxy)-5-nitrostyryl]-1H-1,4-benzodiazepine dihydrochloride |
| 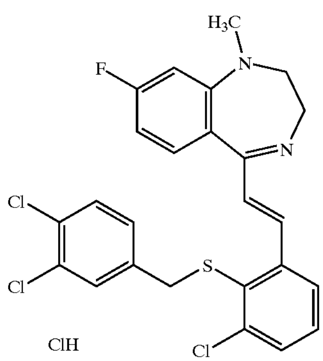 | (E)-5-[3-Chloro-2-(3,4-dichlorobenzylthio)pheflyl]-8-fluoro-2,3-dihydro-1-methyl-1H-1,4-benzodiazepine dihydrochloride |
| 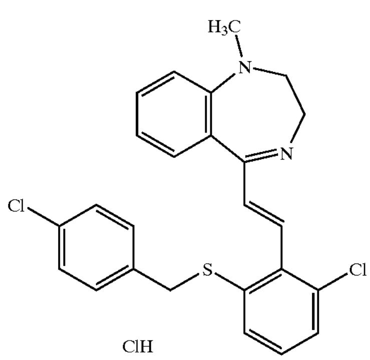 | (E)-5-[2-Chloro-6-(4-chlorobenzylthio)styryl]-2,3-dihydro-1-methyl-1H-1,4-benzodiazepine hydrochloride |

TABLE A-continued

| Structure | Names |
|---|---|
| 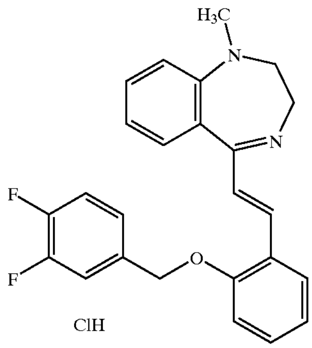 | (E)-5-[2-(3,4-Difluorobenzyloxy)styryl]-2,3-dihydro-1-methyl-1H-1,4-benzodiazepine dihydrochloride |
| 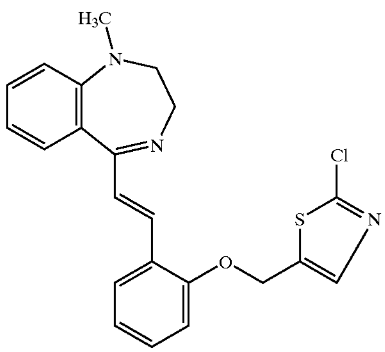 | (E)-5-[2-[(2-Chloro-5-thiazolyl)methpxy]styryl]-2,3-dihydro-1-methyl-1H-1,4-benzodiazepine |
| 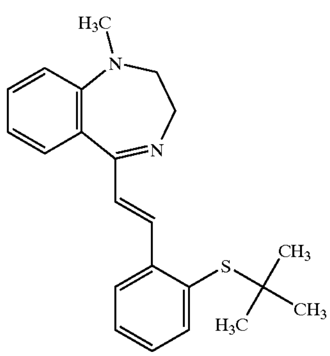 | (E)-5-[2-(tert-Butylthio)styryl]-2,3-dihydro-1-methyl-1H-1,4-benzodiazepine |
| 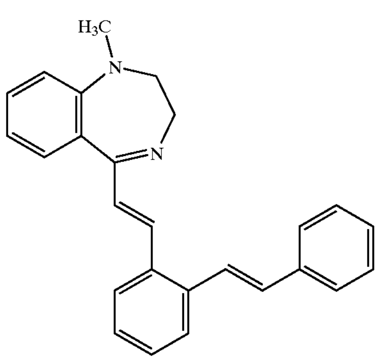 | (all-E)-2,3-Dihydro-1-methyl-5-(2-styrylstyryl)-1H-1,4-benzodiazepine |

TABLE A-continued

| Structure | Names |
|---|---|
| 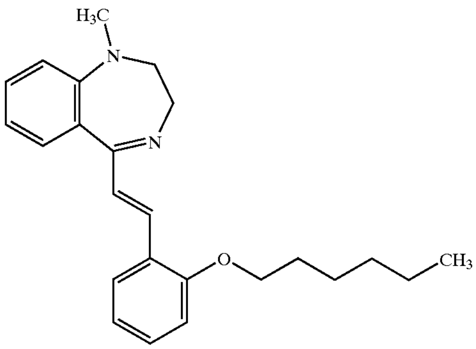 | (E)-5-(2-Hexyloxystyryl)-2,3-dihydro-1-methyl-1H-1,4-benzodiazepine |
| 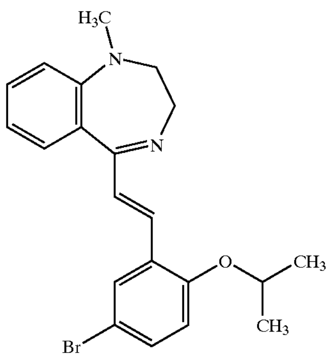 | (E)-5-(5-Bromo-2-isopropoxystyryl)-2,3-dihydro-1-methyl-1H-1,4-benzodiazepine |
| 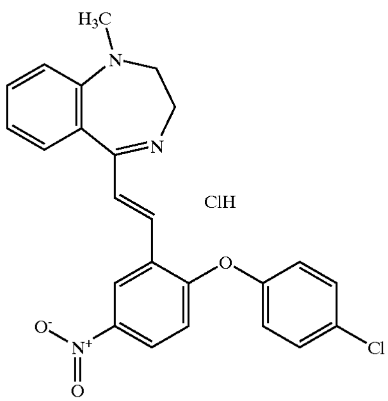 | (E)-5-[2-(4-Chlorophenoxy)-5-nitrostyryl]-3,4-dihydro-1-methyl-1H-1,4-benzodiazepine hydrochloride |
| 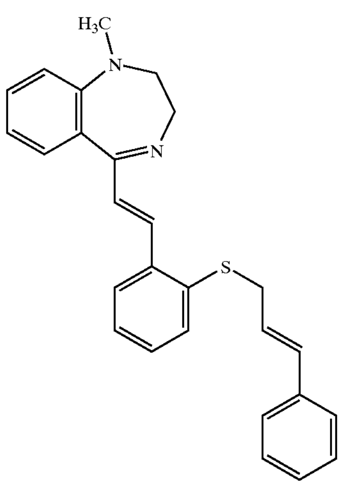 | (all-E)-2,3-Dihydro-1-methyl-5-[2-(styrylthio)styryl]-1H-1,4-benzodiazepine |

TABLE A-continued

| Structure | Names |
| --- | --- |
| 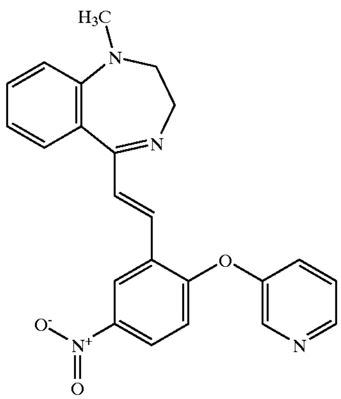 | (E)-2,3-Dihydro-1-methyl-5-[5-nitro-2-(3-pyridyloxy)styryl]-1H-1,4-benzodiazepine |
| 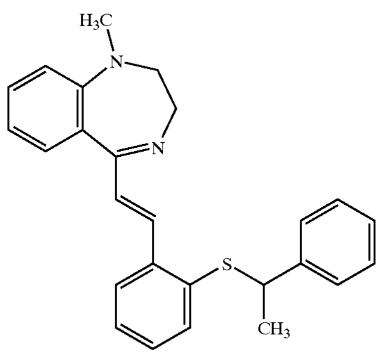 | (E)-2,3-Dihydro-1-methyl-5-[2-(1(RS)-phenylethylthio)styryl]-1H-1,4-benzodiazepine |
| 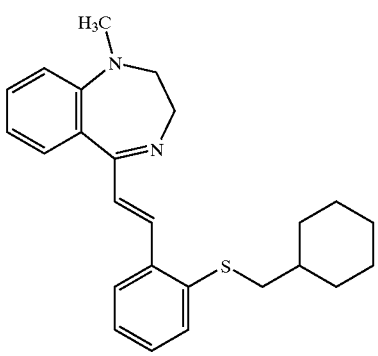 | (E)-5-[2-(Cyclohexylmethylthio)styryl]-2,3-dihydro-1-methyl-1H-1,4-benzodiazepine |
| 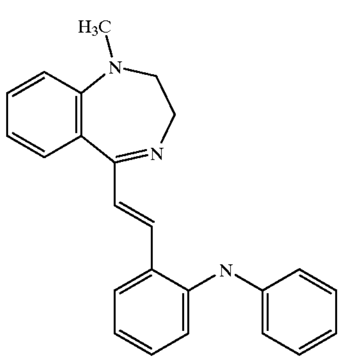 | (E)-N-[2-[2-(2,3-Dihydro-1-methyl-1H-1,4-benzodiazepin-5-yl)vinyl]phenyl]aniline |

TABLE A-continued

| Structure | Names |
|---|---|
| [structure] | (E)-5-[2-(4-Chlorophenylthio)styryl]-2,3-dihydro-1H-1,4-benzodiazepine hydrochloride |
| [structure] | (E)-5-(3,4-Dichlorostyryl)-2,3-dihydro-9-phenyl-1H-1,4-benzodiazepine hydrochloride |
| [structure] | (E)-9-Chloro-5-(3,4-dichlorostyryl)-2,3-dihydro-1H-1,4-benzodiazepine dihydrochloride |
| [structure] | (E)-5-(3,4-Difluorostyryl)-2,3-dihydro-1-methyl-1H-1,4-benzodiazepine dihydrochloride |
| [structure] | (E)-5-(3,4-Dichlorostyryl)-2,3-dihydro-1-methyl-1H-1,4-benzodiazepin-8-amine hydrochloride |
| [structure] | (E)-2,3-Dihydro-5-[2-(1H-indol-3-yl)vinyl]-1-methyl-1H-1,4-benzodiazepine hydrochloride |

The benzodiazepines provided by the present invention are potent inhibitors of the ATPase activity of the human papillomavirus E1 helicase enzyme. They accordingly are therapeutically active substances in the treatment of HPV mediated diseases and therefore can be used as medicaments, either alone or combined with other therapeutically active agents.

The benzodiazepines provided by the present invention are in particular useful in combating HPV disease states such as cutaneous warts on any part of the body, including palmar, plantar and flat/plane warts, anogenital warts (condylomata acuminata), including external and internal (intraurethral, vaginal and cervical) warts, all grades of CIN (cervical intraepithelial neoplasia) and SIL (squamous intraepithelial lesions), recurrent laryngeal papillomatosis (laryngeal warts), epidermodysplasia verruciformis, focal epithelial hyperplasia (Heck's disease), warts or intraepithelial neoplasia affecting the oral and nasal cavities and conjunctival warts.

The compounds of the present invention can be prepared by coupling of a compound of formula

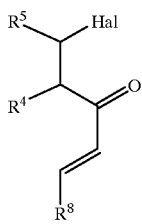

IV wherein
$R^4$ and $R^5$ are as above and Hal is a halogen atom with a diamine of formula $R^1NH(CH_2CH_2)NH_2$  V wherein $R^1$ is as above.

The reaction can be carried out in a conventional manner known to the skilled in the art or following the adaption of a method provided in Journal of Organic Chemistry (1963) p 3013 by Sternbach et al., suitably in pyridine as solvent and at elevated temperature.

The compounds of formula IV and V are new intermediates not known to the state of the art and therefore are also subject of the present invention.

The compounds of formula IV are accessible by condensation of a ketone of formula

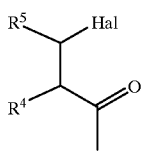

VI wherein
$R^4$ and $R^5$ are as above and Hal is a halogen atom with an aldehyde of the formula $R^8CHO$  VII wherein $R^8$ is as above following methods known to the skilled in the art.

Alternatively the compounds of the present invention can be prepared by coupling of a phosphoric acid ester of formula

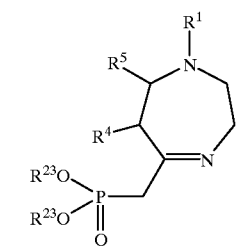

VIII wherein
$R^1$, $R^4$ and $R^5$ are as above and wherein $R^{23}$ is lower alkyl with an aldehyde of the formula $R^8CHO$  VII wherein $R^8$ is as above.

The reaction can be carried out in a conventional manner known to the skilled in the art or following the adaption of a method provided in Buzas and Finet, Tetrahedron Letters 1976, p 2433, suitably in the presence of an alkali metal hydride in tetrahydrofuran.

The phosphoric acid ester of formula VIII is accessible by a reaction of a compound of formula

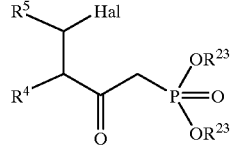

IX wherein
$R^4$, $R^5$ and $R^{23}$ and Hal are as above with a diamine of the formula $R^1NH(CH_2CH_2)NH_2$  V wherein $R^1$ is as above.

The intermediates of formulas VII, VIII, IX and X are not known to the state of the art and are therefore also subject of the present invention.

The compound of formula IX itself can be synthesized starting from a ketone of formula VI by a conversion with a compound of formula

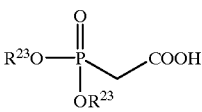

X wherein
$R^{23}$ is as above. This process can be carried out using methods known to the skilled in the art following the adaption of a method provided in Kim et al, Journal of the Chemical Society, Perkin Transactions I 1997, pp 1361.

With regard to the starting materials that are known compounds some of these may be purchased from commercial suppliers. Other starting materials that are known and their analogues can be prepared by methods well known in the art.

For assaying E1 ATPase activity the HPV E1 enzyme has been prepared and purified as follows:

The HPV(11) E1 used in this assay is expressed as a maltose binding protein (MBP) fusion protein from SF9 cells using a baculovirus expression system. Frozen pellets of these cells are thawed by adding the pellet directly into a buffer at 4 OC containing 50 mM Tris-HCl pH 7.5, 20 mM dithiothreitol (DTT), 1 mM EDTA, 600 mM NaCl, 20% glycerol and 3 "Complete" protease inhibitor tablets/50 ml (Boehringer Mannheim cat.no.1 697 498). The cell suspension is then sonicated for 3×10 seconds before centrifuging at 18000 rpm for 30 minutes to remove the cell debris. The clarified extract is then passed down a DE52 ion exchange column which is washed with a buffer containing 50 mM Tris-HCl pH 7.5, 2 mM DTT, 1 mM EDTA, 600 mM NaCl and 20% glycerol. The column flow through plus the first 10 mls of wash buffer are then passed down an amylose affinity column which binds MBP tagged proteins. This column is washed with 3 column bed volumes of the wash buffer before being eluted with wash buffer containing 10 mM maltose. The eluted protein peak containing purified HPV (11) E1 is then dialysed overnight against 2 L of buffer containing 20 mM Tris-HCl pH 7.5, 2 mM DTT, 20 mM NaCl and 20% glycerol. The dialyzed material is used in the assay.

E1 ATPase activity can be measured as follows:

The standard reaction contains 50 mM MOPs KOH pH 7.0, 500 μM MgCl2, 20 μM ATP, 50 mM NaCl, 40 μl of a suitably diluted enzyme extract and 10 μl of inhibitor in a final volume of 100 μl. The ATP contains 0.1 μCi [γ$^{33}$P]ATP per reaction. The enzyme diluent contains 50 mM MOPs KOH pH7.0 and 1 mg/ml BSA. The inhibitor is diluted to give a range of concentrations in neat DMSO. Reaction tubes are incubated for 1 hour at 37° C. (producing linear kinetics) after which the reaction is terminated by heat inactivation at 85° C. for 2 minutes. 500 μl 15% activated charcoal in PBS is then added to each reaction. The activated charcoal used is 100–400 mesh untreated powder (Sigma cat No C-5260); prior to use in the assay this is washed in PBS several times and allowed to settle out under gravity, any fine particles still in suspension being decanted off after each wash. The reactions are left on ice for 1 hour after which the charcoal is pelleted out by centrifugation at 14000 rpm for 10 minutes. The charcoal pellet contains unconverted [γ$^{33}$P] ATP, whilst any free inorganic $^{33}$P, the reaction product, will remain in the supernatant. The amount of radioactivity present in 300 μl of supernatant is then measured by scintillation spectrophotometry.

The results can be calculated as follows:

The degree of inhibition at each inhibitor concentration is expressed as a percentage of the control reaction (100%) after subtracting a measured blank value, which represents the amount of free inorganic $^{33}$P present in a reaction containing heat inactivated enzyme. An IC$_{50}$ value (concentration of test compound which inhibits enzyme activity by 50%) is then calculated from a dose response curve of log$_{10}$ inhibitor concentration against percentage of the control reaction.

Preferred compounds of the invention tested in the above assay have an IC$_{50}$ value up to about 50 μM.

Specific examples of IC$_{50}$ values for some compounds of the invention are set out in the table B below.

TABLE B

| Structure | Activity/μM | Example No. |
| --- | --- | --- |
| 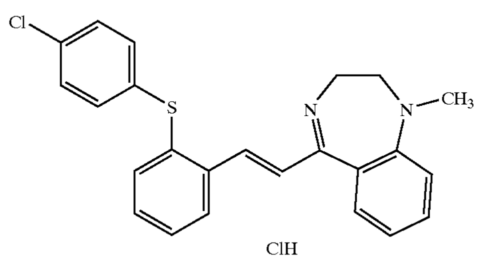 | 1.6 | 121 |
| 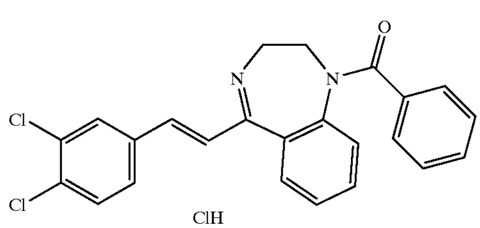 | 5.6 | 125 |

TABLE B-continued

| Structure | Activity/μM | Example No. |
|---|---|---|
| 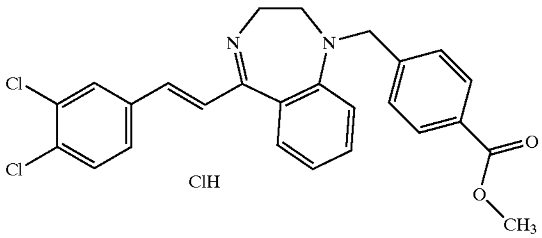 | 2.2 | 127 |
| 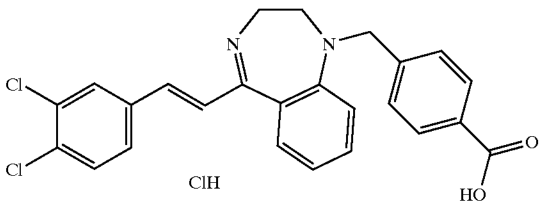 | 4.4 | 132 |
| 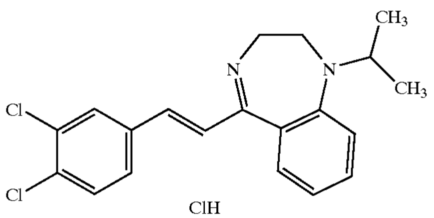 | 2 | 123 |
| 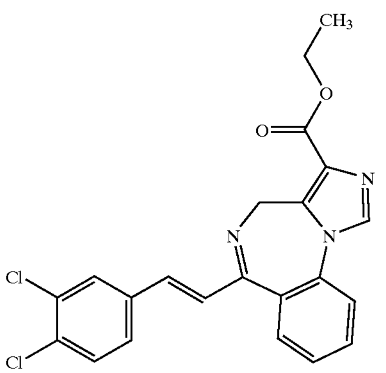 | 20 | 139 |
| 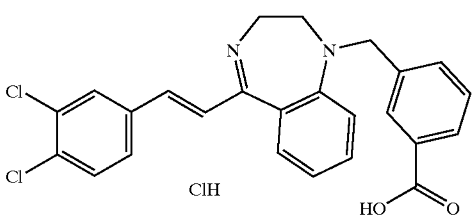 | 3.1 | 133 |
| 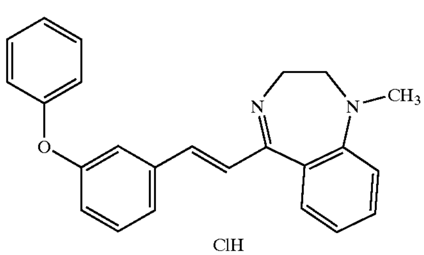 | 2.4 | 3 |

TABLE B-continued

| Structure | Activity/μM | Example No. |
|---|---|---|
| (structure) | 26 | 136 |
| (structure) | 5.6 | 38 |
| (structure) | 3 | 29 |
| (structure) | 20 | 137 |
| (structure) | 8.6 | 162 |

TABLE B-continued
| Structure | Activity/μM | Example No. |
|---|---|---|
| 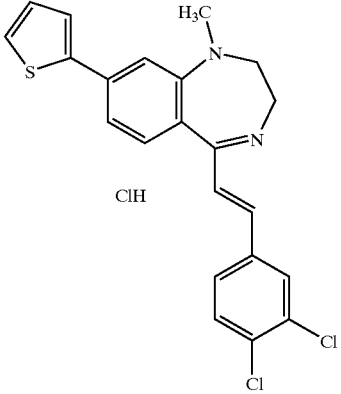 | 12 | 164 |
| 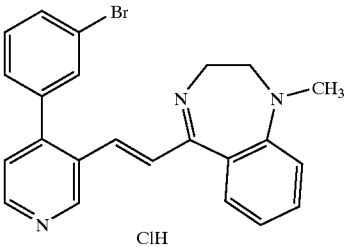 | 4.2 | 6 |
| 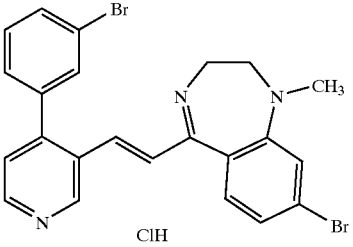 | 2.4 | 42 |
| 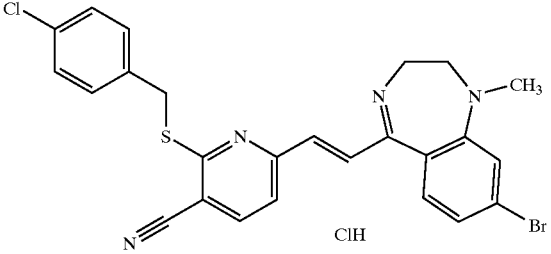 | 2.5 | 44 |
| 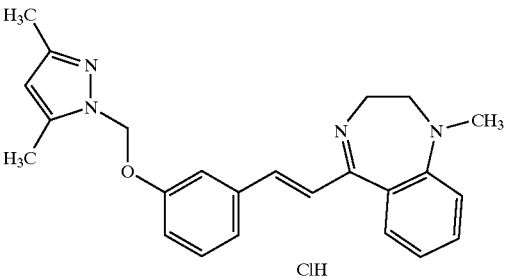 | 19 | 92 |

TABLE B-continued

| Structure | Activity/μM | Example No. |
|---|---|---|
| [Structure: 4-bromophenyl-pyridyl styryl benzodiazepine, CH3, ClH salt] | 5.4 | 147 |

The compound of the present invention as well as its pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions or topically, e.g. in the form of a cream, a gel or a solution.

The compound of the present invention and its pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Suitable excipients for topical gels are e.g. natural gums such as xanthan and tragacanth, semisynthetic cellulose derivatives such as methylcelluloses and carboxymethylcelluloses, carbomers, clays such as silicates and presevatives such as benzoic acid or parabens.

Suitable excipients for topical creams are e.g. oils and waxes, emulsifying agents such as surfactants and polymers such as polyoxamers and preservatives.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of the compound of formula I should be appropriate, although the above upper limit can also be exceeded when necessary.

The following examples illustrate the present invention:

EXAMPLE 1

(E)-5-(3,4-Difluorostyryl)-2,3-dihydro-1-methyl-1H-1,4-benzodiazepine dihydrochloride To a solution of 43 mg (0.14 mmol) of (1-methyl-1,2,3,4-tetrahydrobenzo[e][1,4]diazepin-5-ylidenemethyl) phosphonic acid diethyl ester in 2.5 ml of tetrahydrofuran was added 8.3 mg (0.21 mmol) of sodium hydride (60% dispersion in mineral oil). After 5 minutes 19.9 mg (0.14 mmol) of 3,4-difluorobenzaldehyde was added and the mixture was stirred for 2.75 hours. The product was purified by column chromatography (20 g IST pre-packed column) eluting with 3% methanol/ethyl acetate and treated with 0.05 ml of 4M hydrogen chloride in dioxan. The solvent was evaporated to leave a red gum which was recrystallized from ethyl acetate—petroleum ether (40–60° C.) to give 14 mg of (E)-5-(3,4-difluorostyryl)-2,3-dihydro-1-methyl-1H-1,4-benzodiazepine dihydrochloride as dark red crystals. 1H NMR (400 MHz, DMSO) δ: 2.97 (s, 3H), 3.77 (m, 2H), 3.83 (m, 2H), 7.06 (t, 1H), 7.18 (d, 1H), 7.50 (2H, dd), 7.55–7.70 (m, 4H), 7.95 (m, 1H); MS: m/e 298 (M+).

The starting material was prepared as follows:

To a solution of 2.34 g (11.9 mmol) of diethylphosphonoacetic acid in toluene at 0° C. was added 4.82 g (47.7 mmol) of triethylamine followed by 1.94 g (17.9 mmol) of chlorotrimethylsilane. The mixture was stirred at ambient temperature for 1 hour, then 1.13 g (11.9 mmol) of magnesium chloride was added and the mixture was stirred for a further 1 hour. To the mixture was added 2.0 g (14.3 mmol) of 2-fluorobenzoyl chloride and the mixture was stirred for 72 hours. The mixture was partitioned between 200 ml of water and 250 ml, 100 ml of dichloromethane. The combined organic portions were dried (magnesium sulphate), filtered and evaporated. The residue was purified by column chromatography eluting with 3–5% methanol/ dichloromethane to give 2.1 g (64%) of [2-(2-fluorophenyl)-2-oxoethyl]phosphonic acid diethyl ester as a colorless oil; MS: m/e 274.9 [M+H]+.

A mixture of 10.45 g (38.1 mmol) of [2-(2-fluorophenyl)-2-oxoethyl]phosphonic acid diethyl ester and 14.1 g (190 mmol) N-methylethylenediamine in 100 ml of pyridine was heated at 95° C. for 18 hours. The solvent was evaporated and the residue was partitioned between 200 ml of water and 2×100 ml of dichloromethane. The combined organic portions were dried (magnesium sulphate), filtered and evaporated. The residue was purified by column chromatography eluting with 5% methanol/dichloromethane to give 3.14 g (26%) of (1-methyl-1,2,3,4-tetrahydrobenzo[e][1,4] diazepin-5-ylidenemethyl)phosphonic acid diethyl ester as a light brown oil; MS: m/e 311.0 [M+H]+.

In a manner analogous to that described in Example 1, starting with (1-methyl-1,2,3,4-tetrahydrobenzo[e][1,4] diazepin-5-ylidenemethyl)phosphonic acid diethyl ester (prepared as described in Example 1), and the appropriate aldehyde, the compounds shown in Table 1 were also prepared:

TABLE 1

| Compound | Structure | Name | MS (ES) (M + H)+ |
|---|---|---|---|
| Example 2 | 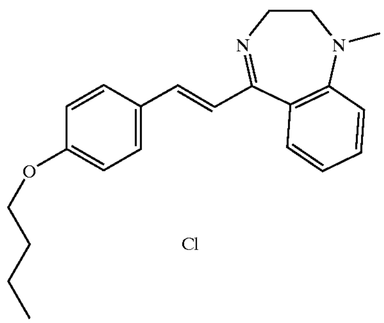 | (E)-5-(4-Butoxystyryl)-2,3-dihydro-1-methyl-1H-1,4-benzodiazepine dihydrochloride | 334 (M+; EI) |
| Example 3 | 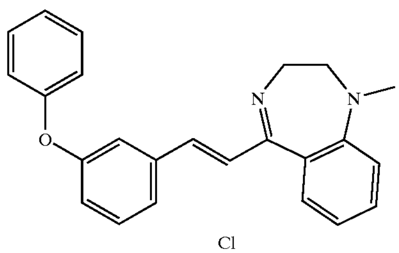 | (E)-2,3-Dihydro-1-methyl-5-(3-phenoxystyryl)-1H-1,4-benzodiazepine dihydrochloride | 354 (M+; EI) |
| Example 4 | 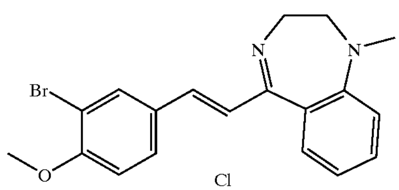 | (E)-5-(3-Bromo-4-methoxystyryl)-2,3-dihydro-1-methyl-1H-1,4-benzodiazepine dihydrochloride | 370 (M+; EI) |
| Example 5 | 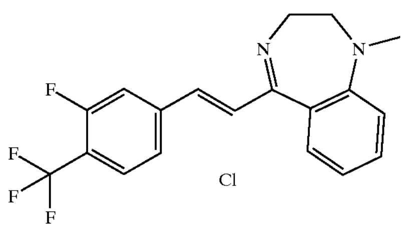 | (E)-5-[3-Fluoro-4-(trifluoromethyl)styryl]-2,3-dihydro-1-methyl-1H-benzo[e][1,4]diazepine dihydrochloride | 348 (M+; EI) |
| Example 6 | 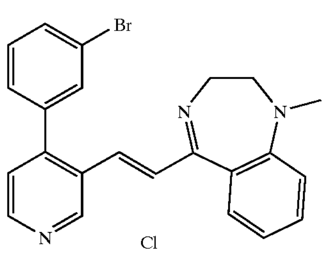 | (E)-5-[2-[4-(3-Bromophenyl)-3-pyridyl]vinyl]-2,3-dihydro-1-methyl-1H-1,4-benzodiazepine dihydrochloride | 416 (M+; EI) |
| Example 7 | 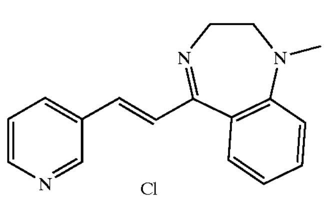 | (E)-2,3-Dihydro-1-methyl-5-[2-(3-pyridyl)vinyl]-1H-1,4-benzodiazepine dihydrochloride | 263 (M+; EI) |

TABLE 1-continued

| Compound | Name | MS (ES) (M + H)+ |
|---|---|---|
| Example 8 | (E)-5-[2-[3-(4-Chlorophenylthio)-5-(trifluoromethyl)-2-pyridyl]vinyl]-2,3-dihydro-1-methyl-1H-1,4-benzodiazepine dihydrochloride | 473 (M+; EI) |
| Example 9 | (E)-2-(4-Chlorobenzylthio)-6-[2-(2,3-dihydro-1-methyl-1H-1,4-benzodiazepin-5-yl)vinyl]-3-pyridinecarbonitrile dihydrochloride | 445 (M+) |
| Example 10 | (E)-2,3-Dihydro-5-[2-(1H-indol-3-yl)vinyl]-1-methyl-1H-1,4-benzodiazepine dihydrochloride | 302 (M+) |
| Example 11 | tert-Butyl (E)-2-[2-(2,3-dihydro-1-methyl-1H-1,4-benzodiazepin-5-yl)vinyl]benzoate dihydrochloride | 362 (M+; EI) |
| Example 12 | (E)-5-[2-[4-(4-Bromophenyl)-3-pyridyl]vinyl]-2,3-dihydro-1-methyl-1H-1,4-benzodiazepine dihydrochloride | 418 (M+; EI) |

TABLE 1-continued

| Compound | Name | MS (ES) (M + H)+ |
|---|---|---|
| Example 13 | (E)-2-[2-(2,3-Dihydro-1-methyl-1H-1,4-benzodiazepin-5-yl)vinyl]aniline dihydrochloride | 277 (M+; EI) |
| Example 14 | (E)-5-(2-Fluorostyryl)-2,3-dihydro-1-methyl-1H-1,4-benzodiazepine dihydrochloride | 280 (M+; EI) |
| Example 15 | (E)-5-(2-Benzylthio-5-nitrostyryl)-2,3-dihydro-1-methyl-1H-1,4-benzodiazepine dihydrochloride | 429 (M+; EI) |
| Example 16 | (E)-5-[2-[(2-Chloro-5-thiazolyl)methoxy]styryl]-2,3-dihydro-1-methyl-1H-1,4-benzodiazepine | 410.2 |

TABLE 1-continued

| Compound | Structure | Name | MS (ES) (M + H)+ |
|---|---|---|---|
| Example 17 | 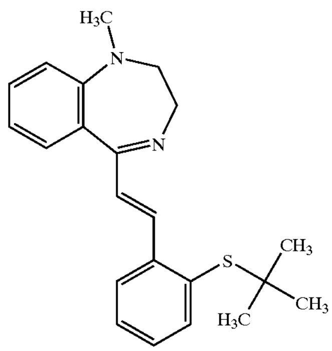 | (E)-5-[2-(tert-Butylthio)styryl]-2,3-dihydro-1-methyl-1H-1,4-benzodiazepine | 351.3 |
| Example 18 | 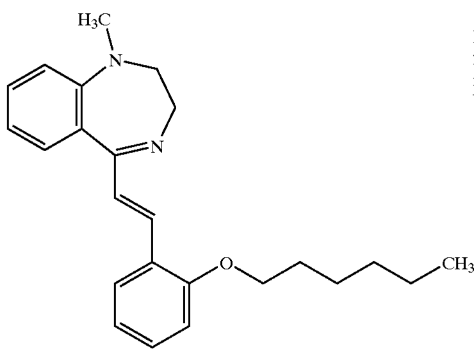 | (E)-5-(2-Hexyloxystyryl)-2,3-dihydro-1-methyl-1H-1,4-benzodiazepine | 363.4 |
| Example 19 | 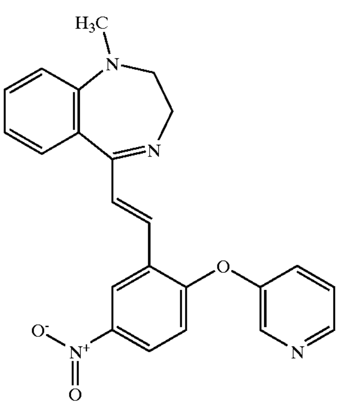 | (E)-2,3-Dihydro-1-methyl-5-[5-nitro-2-(3-pyridyloxy)styryl]-1H-1,4-benzodiazepine | 401.2 |
| Example 20 | 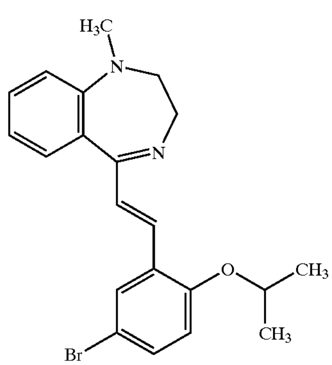 | (E)-5-(5-Bromo-2-isopropoxystyryl)-2,3-dihydro-1-methyl-1H-1,4-benzodiazepine | 399.2 |

EXAMPLE 21

(E)-2,3-Dihydro-1-methyl-5-[2-(2-phenylethyl) styryl]-1H-1,4-benzodiazepine

In an analogous fashion to Example 1 was prepared (E)-2,3-dihydro-1-methyl-5-[2-(2-phenylethyl)styryl]-1H-1,4-benzodiazepine as a light yellow oil, MS: m/e 367.3 [M+H]+.

The aldehyde starting material was prepared as follows:

A mixture of 3 g (13.2 mmol) of 2-phenethylbenzoic acid, 3.8 g (19.8 mmol) of 1-[3-(dimethylamino)propyl]-3-ethylcarbodiimide hydrochloride, 2.7 g (20.0 mmol) of 1-hydroxybenzotriazole hydrate, 3 ml (23 mmol) of N-ethylmorpholine and 1.94 g (19.9 mmol) of N,O-dimethylhydroxylamine hydrochloride was stirred in 50 ml of dichloromethane at room temperature for 2 hours. The solution was diluted with dichloromethane and washed sequentially with saturated aqueous citric acid solution and saturated aqueous sodium bicarbonate solution, dried over magnesium sulphate, filtered and evaporated to afford N-methoxy-N-methyl-2-phenethylbenzamide as a colorless oil. To a solution of 1 g (3.7 mmol) of this oil in 10 ml tetrahydrofuran at 0° C. was added 2.2 ml of a 1M solution of lithium aluminium hydride in tetrahydrofuran. The solution was stirred at 0° C. for 25 minutes and saturated aqueous potassium hydrogensulphate and ether were then added and the mixture stirred at room temperature for 30 minutes. The layers were separated and the organic layer washed with saturated aqueous sodium bicarbonate solution, dried over magnesium sulphate, filtered and evaporated to afford 2-phenethyl-benzaldehyde as a colorless oil which was used directly without further purification.

In an analogous fashion to Example 21, by replacing 2-phenethylbenzoic acid with the appropriate carboxylic acid, the compounds shown in Table 2 were also prepared:

TABLE 2

| Compound | Structure | Name | MS (ES) (M + H)+ |
|---|---|---|---|
| Example 22 | 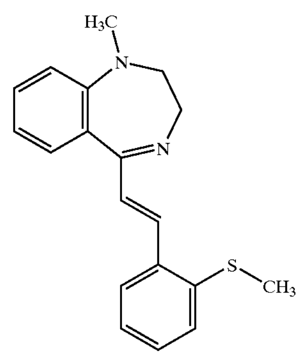 | (E)-2,3-Dihydro-1-methyl-5-(2-methylthiostyryl)-1H-1,4-benzodiazepine | 309.2 |
| Example 23 | 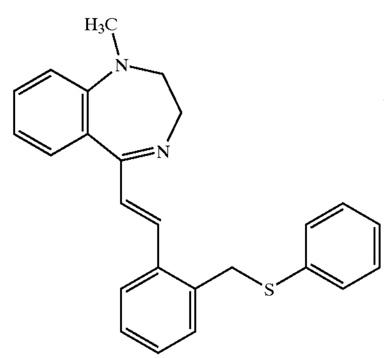 | (E)-2,3-Dihydro-1-methyl-5-[2-(phenylthiomethyl)-styryl]-1H-1,4-benzodiazepine | 385.3 |
| Example 24 | 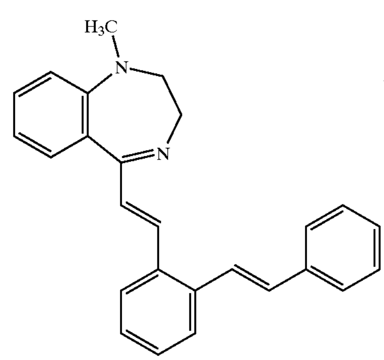 | (E,E)-2,3-Dihydro-1-methyl-5-(2-styrylstyryl)-1H-1,4-benzodiazepine | 365.3 |

TABLE 2-continued

| Compound | Structure | Name | MS (ES) (M + H)+ |
|---|---|---|---|
| Example 25 | 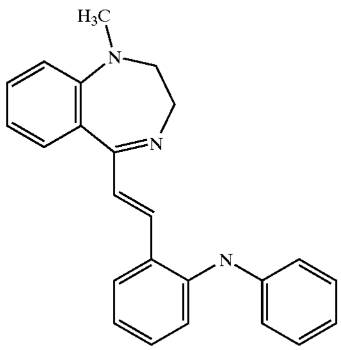 | (E)-N-[2-[2-(2,3-Dihydro-1-methyl-1H-1,4-benzo-diazepin-5-yl)vinyl]phenyl]aniline | 354.3 |

EXAMPLE 26

(E,E)-2,3-Dihydro-1-methyl-5-[2-(styrylthio)styryl]-1H-1,4-benzodiazepine

In an analogous fashion to Example 21 there was obtained (E,E)-2,3-Dihydro-1-methyl-5-[2-(styrylthio)styryl]-1H-1,4-benzodiazepine as a yellow gum, MS (ES) (M+H)+ 411.2.

The carboxylic acid starting material was prepared as follows:

To a solution of 1.28 g (6.49 mmol) of cinnamyl bromide in 8 ml of ethanol at room temperature under an atmosphere of nitrogen was added a solution of 1 g (6.49 mmol) of thiosalicylic acid in 5.3 ml of 10% aqueous sodium hydroxide solution. The solution was stirred at room temperature for 16 hours and the solvent then removed under reduced pressure. The residue was dissolved in water and concentrated hydrochloric acid was added. The resultant solid was filtered off and dried. There was obtained 1.7 g of 2-styrylsulfanylbenzoic acid as a white solid, MS: m/e 270 M+.

In an analogous fashion to Example 26, by replacing cinnamyl bromide with the appropriate bromide the compounds shown in Table 3 were also prepared:

TABLE 3

| Compound | Structure | Name | MS (ES) (M + H)+ |
|---|---|---|---|
| Example 27 | 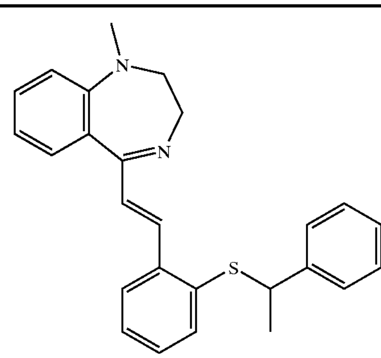 | (E)-2,3-Dihydro-1-methyl-5-[2-(1(RS)-phenylethylthio)styryl]-1H-1,4-benzodiazepine | 399.3 |
| Example 28 | 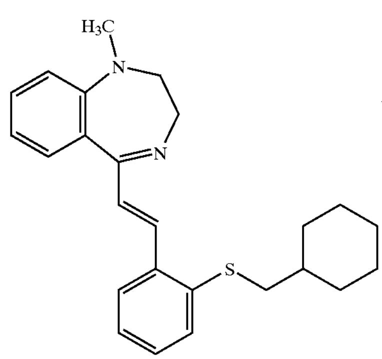 | (E)-5-[2-(Cyclohexylmethylthio)-styryl]-2,3-dihydro-1-methyl-1H-1,4-benzodiazepine | 391.3 |

In an analogous fashion to Example 1, using the appropriate acid chloride, and 3,4 dichlorobenzaldehyde the compounds shown in Table 4 were also prepared:

TABLE 4

| Example 29 | | (E)-5-(3,4-Dichlorostyryl)-2,3-dihydro-1-methyl-1H-pyrido[2,3-e][1,4]diazepine hydrochloride (1:3) | 332.1 |
|---|---|---|---|
| Example 30 | | (E)-5-(3,4-Dichlorostyryl)-2,3-dihydro-1-methyl-1H-pyrido[3,4-e][1,4]diazepine | 332.1 |
| Example 31 | | (E)-5-(3,4-Dichlorostyryl)-2,3-dihydro-1-methyl-1H-pyrido[3,2-e][1,4]diazepine | 332.2 |
| Example 32 | | (E)-5-(3,4-Dichlorostyryl)-7-(trifluoromethyl)-2,3-dihydro-1-methyl-1H-1,4-benzodiazepine hydrochloride | 399.1 |
| Example 33 | | (E)-5-(3,4-Dichlorostyryl)-8-(trifluoromethyl)-2,3-dihydro-1-methyl-1H-1,4-benzodiazepine hydrochloride | 398.8 |
| Example 34 | | (E)-5-(3,4-Dichlorostyryl)-2,3-dihydro-8-methoxy-1-methyl-1H-1,4-benzodiazepine hydrochloride | 361.2 |
| Example 35 | | (E)-5-(3,4-Dichlorostyryl)-6-fluoro-2,3-dihydro-1-methyl-1H-1,4-benzodiazepine hydrochloride | 349.2 |

TABLE 4-continued

| Example 36 | (structure) | (E)-5-(3,4-Dichlorostyryl)-2,3-dihydro-1-methyl-7-nitro-1H-1,4-benzodiazepine | 376.1 |
|---|---|---|---|
| Example 37 | (structure) | (E)-5-(3,4-Dichlorostyryl)-2,3-dihydro-1-methyl-8-nitro-1H-1,4-benzodiazepine hydrochloride | 376.2 |

In an analogous fashion to Example 1, replacing 3,4-difluorobenzaldehyde with 3,4 dichlorobenzaldehyde, and N-methylethylenediamine with ethylenediamine, and using the appropriate acid chloride, the compounds shown in Table 5 were also prepared:

TABLE 5

| Example 38 | (structure) | (E)-5-(3,4-Dichlorostyryl)-9-(trifluoromethyl)-2,3-dihydro-1H-1,4-benzodiazepine dihydrochloride | 385.5 |
|---|---|---|---|
| Example 39 | (structure) | (E)-5-(3,4-Dichlorostyryl)-8-(trifluoromethyl)-2,3-dihydro-1H-1,4-benzodiazepine hydrochloride | 385.1 |
| Example 40 | (structure) | (E)-5-(3,4-Dichlorostyryl)-7-(trifluoromethyl)-2,3-dihydro-1H-1,4-benzodiazepine hydrochloride | 384.8 |

EXAMPLE 41

(E)-8-Bromo-5-(3,4-dichlorostyryl)-2,3-dihydro-1-methyl-1H-1,4-benzodiazepine dihydrochloride To 122 mg (0.31 mmol) of (8-bromo-1-methyl-1,2,3,4-tetrahydrobenzo[e][1,4]diazepin-5-ylidenemethyl)

phosphonic acid diethyl ester in 2.5 ml of tetrahydrofuran was added 26 mg (0.55 mmol) of sodium hydride (60% priate aldehyde, the compounds shown in Table 6 were also prepared:

TABLE 6

| Compound | Structure | Name | MS (ES) (M + H)+ |
|---|---|---|---|
| Example 42 | 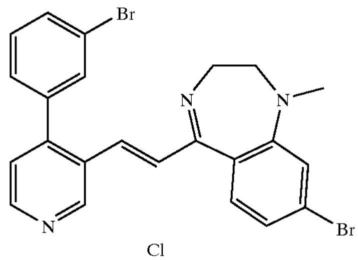 | (E)-8-Bromo-5-[2-[4-(3-bromophenyl)-3-pyridyl]vinyl]-2,3-dihydro-1-methyl-1H-1,4-benzodiazepine dihydrochloride | 429 (M+; EI) |
| Example 43 | 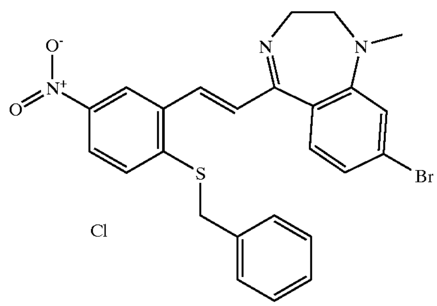 | (E)-5-(2-Benzylthio-5-nitrostyryl)-8-bromo-2,3-dihydro-1-methyl-1H-1,4-benzodiazepine dihydrochloride | 507 (M+; EI) |
| Example 44 | | (E)-6-[2-(8-Bromo-2,3-dihydro-1-methyl-1H-1,4-benzodiazepin-5-yl)vinyl]-2-(4-chlorobenzylthio)-3-pyridinecarbonitrile dihydrochloride | 523 ([M + H]+; EI) | dispersion in mineral oil). After 5 minutes 57 mg (0.33 mmol) of 3,4-difluorobenzaldehyde was added and the mixture was stirred for 6 hours. The product was purified by column chromatography (20 g IST pre-packed column) eluting with 1% methanol/dichloromethane and treated with 0.10 ml of 4M hydrogen chloride in dioxan. The solvent was evaporated to leave a red gum which was recrystallized from acetone—petroleum ether (40–60° C.) to give 77 mg of (E)-5-(3,4-difluorostyryl)-2,3-dihydro-1-methyl-1H-1,4-benzodiazepine dihydrochloride as orange crystals; MS: m/e 408 (M+).

The starting material was prepared as follows:

(8-bromo-1-methyl-1,2,3,4-tetrahydrobenzo[e][1,4]diazepin-5-ylidenemethyl)phosphonic acid diethyl ester was prepared in an analogous fashion to (1-methyl-1,2,3,4-tetrahydrobenzo[e][1,4]diazepin-5-ylidenemethyl)phosphonic acid diethyl ester, prepared in Example 1, by replacing 2-fluorobenzoic acid with 2-fluoro-4-bromobenzoic acid.

In a manner analogous to that described in Example 41, starting with (8-bromo-1-methyl-1,2,3,4-tetrahydrobenzo[e][1,4]diazepin-5-ylidenemethyl)phosphonic acid diethyl ester (prepared as described in Example 41), and the appro-

EXAMPLE 45

(E)-9-Chloro-5-(3,4-dichlorostyryl)-2,3-dihydro-1H-1,4-benzodiazepine dihydrochloride To a solution of 91 mg (0.275 mmol) of (9-chloro-1,2,3,4-tetrahydrobenzo[e][1,4]diazepin-5-ylidenemethyl)phosphonic acid diethyl ester in 2 ml of tetrahydrofuran was added 19 mg (0.48 mmol) of sodium hydride (60% dispersion in mineral oil). After 10 minutes 50 mg (0.29 mmol) of 3,4-dichlorobenzaldehyde was added and the mixture was stirred for 18 hours. The product was purified by column chromatography (20 g IST pre-packed column) eluting with 1% methanol/dichloromethane and treated with 0.10 ml of 4M hydrogen chloride in dioxan. The solvent was evaporated to give 90 mg of (E)-9-chloro-5-(3,4-dichlorostyryl)-2,3-dihydro-1H-1,4-benzodiazepine dihydrochloride as an orange solid; MS: m/e 352.7 [M+H]+.

The starting material was prepared as follows:

(9-chloro-1,2,3,4-tetrahydrobenzo[e][1,4]diazepin-5-ylidenemethyl)phosphonic acid diethyl ester was prepared in an analogous fashion to (1-methyl-1,2,3,4-tetrahydrobenzo[e][1,4]diazepin-5-ylidenemethyl)phosphonic acid diethyl ester, prepared in Example 1, by replacing 2-fluorobenzoic acid with 2-fluoro-3-chlorobenzoic acid and N-methylethylenediamine with ethylenediamine.

EXAMPLE 46

(E)-5-[4-(3-Bromophenyl)-3-pyridyl]-7-fluoro-2,3-dihydro-1-methyl-1H-1,4-benzodiazepine dihydrochloride To 95 mg (0.289 mmol) of (7-fluoro-1-methyl-1,2,3,4-tetrahydrobenzo[e][1,4]diazepin-5-ylidenemethyl)phosphonic acid diethyl ester in 2 ml of tetrahydrofuran was added 20 mg (0.51 mmol) of sodium hydride (60% dispersion in mineral oil). After 5 minutes 80 mg (0.30 mmol) of 3-formyl-4-(3-bromophenyl)pyridine was added and the mixture was stirred for 18 hours. The product was purified by column chromatography (20 g IST pre-packed column) eluting with 1% methanol/dichloromethane and treated with 0.10 ml of 4M hydrogen chloride in dioxan. The solvent was evaporated and the residue was triturated with diethyl ether to give 10 mg of (E)-5-[4-(3-bromophenyl)-3-pyridyl]-7-fluoro-2,3-dihydro-1-methyl-1H-1,4-benzodiazepine dihydrochloride as a dark red solid; MS: m/e 437.8 [M+H]$^+$.

The starting material was prepared as follows:

(7-fluoro-1-methyl-1,2,3,4-tetrahydrobenzo[e][1,4]diazepin-5-ylidenemethyl)phosphonic acid diethyl ester was prepared in an analogous fashion to (1-methyl-1,2,3,4-tetrahydrobenzo[e][1,4]diazepin-5-ylidenemethyl)phosphonic acid diethyl ester, prepared in Example 1, by replacing 2-fluorobenzoic acid with 2,5-difluorobenzoic acid.

EXAMPLE 47

(E)-5-(2-Benzylthio-5-nitrostyryl)-7-fluoro-2,3-dihydro-1-methyl-1H-1,4-benzodiazepine dihydrochloride In a manner analogous to that described in Example 46, starting with (7-fluoro-1-methyl-1,2,3,4-tetrahydrobenzo[e][1,4]diazepin-5-ylidenemethyl)phosphonic acid diethyl ester (prepared as described in Example 46), and 2-benzylthio-5-nitrobenzaldehyde there was obtained (E)-5-(2-benzylthio-5-nitrostyryl)-7-fluoro-2,3-dihydro-1-methyl-1H-1,4-benzodiazepine dihydrochloride, MS: m/e 448 [M+H]$^+$.

EXAMPLE 48

(E)-8-Chloro-5-(3,4-dichlorostyryl)-2,3-dihydro-1-methyl-1H-1,4-benzodiazepine dihydrochloride To 210 mg (0.609 mmol) of (8-chloro-1-methyl-1,2,3,4-tetrahydrobenzo[e][1,4]diazepin-5-ylidenemethyl)phosphonic acid diethyl ester in 4 ml of tetrahydrofuran was added 36 mg (0.91 mmol) of sodium hydride (60% dispersion in mineral oil). After 10 minutes 112 mg (0.64 mmol) of 3,4-dichlorobenzaldehyde was added and the mixture was stirred for 18 hours. The product was purified by column chromatography (20 g IST pre-packed column) eluting with 2% methanoludichloromethane and treated with 0.15 ml of 4M hydrogen chloride in dioxan. The solvent was evaporated and the residue was recrystallised from acetone—petroleum ether (40–60° C.) to give 40 mg of (E)-9-chloro-5-(3,4-dichlorostyryl)-2,3-dihydro-1H-1,4-benzodiazepine dihydrochloride as yellow needles; MS: m/e 364 (M$^+$).

The starting material was prepared as follows:

(8-chloro-1-methyl-1,2,3,4-tetrahydrobenzo[e][1,4]diazepin-5-ylidenemethyl)phosphonic acid diethyl ester was prepared in an analogous fashion to (1-methyl-1,2,3,4-tetrahydrobenzo[e][1,4]diazepin-5-ylidenemethyl)phosphonic acid diethyl ester, as described in Example 1 by replacing 2-fluorobenzoic acid with 4-chloro-2-fluorobenzoic acid.

In a manner analogous to that described in Example 48, starting with (8-chloro-1-methyl-1,2,3,4-tetrahydrobenzo[e][1,4]diazepin-5-ylidenemethyl)phosphonic acid diethyl ester (prepared as described in Example 48), and the appropriate aldehyde the compounds shown in Table 7 were also prepared:

TABLE 7

| Compound | Structure | Name | MS (ES) (M + H)+ |
| --- | --- | --- | --- |
| Example 49 | 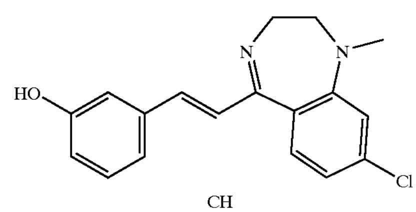 | (E)-3-[2-(8-Chloro-2,3-dihydro-1-methyl-1H-1,4-benzodiazepin-5-yl)vinyl]phenol dihydrochloride | 312 |
| Example 50 | 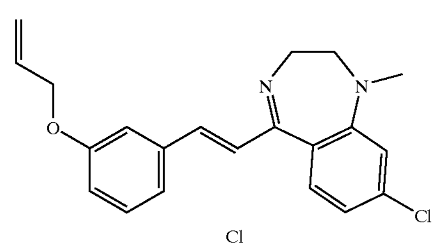 | (E)-5-(3-Allyloxystyryl)-8-chloro-2,3-dihydro-1-methyl-1H-1,4-benzodiazepine dihydrochloride | 352 (M$^+$; EI) |

TABLE 7-continued

| Compound | Structure | Name | MS (ES) (M + H)+ |
|---|---|---|---|
| Example 51 | 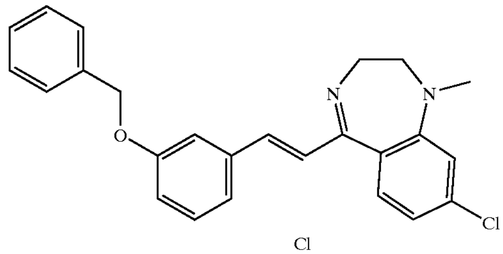 | (E)-5-(3-Benzyloxystyryl)-8-chloro-2,3-dihydro-1-methyl-1H-1,4-benzodiazepine dihydrochloride | 402 (M+; EI) |
| Example 52 | 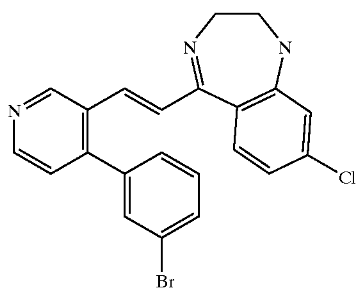 | (E)-5-[2-[4-(3-Bromophenyl)-3-pyridyl]vinyl]-8-chloro-2,3-dihydro-1H-1,4-benzodiazepine | 440.2 |

EXAMPLE 53

(E)-5-(2-Benzylthiostyryl)-2,3-dihydro-1-methyl-1H-1,4-benzodiazepine dihydrochloride To a mixture of 56 mg of 2-fluorobenzaldehyde (0.45 mmol) and 56 mg (0.45 mmol) of benzyl mercaptan in 3 ml of tetrahydrofuran was added 22 mg of sodium hydride (60% dispersion in mineral oil). After 1.2 hours 112 mg (0.36 mmol) of (1-methyl-1,2,3,4-tetrahydrobenzo[e][1,4]diazepin-5-ylidenemethyl)phosphonic acid diethyl ester (prepared as described in Example 1) was added followed by 25 mg (0.63 mmol) of sodium hydride (60% dispersion in mineral oil). The mixture was stirred for 1.3 hours. The mixture was partitioned between 20 ml of water and 5 ml of dichloromethane. The organic portion was dried (magnesium sulphate), filtered and evaporated. The product was purified by column chromatography (20 g IST prepacked column) eluting with 0–2% methanol/dichloromethane and treated with 0.25 ml of 4M hydrogen chloride in dioxan. The solvent was evaporated to leave a red gum which was lyophilised to give 75 mg of (E)-5-(2-benzylthiostyryl)-2,3-dihydro-1-methyl-1H-1,4-benzodiazepine dihydrochloride as dark red powder; MS: m/e 385 [M+H]+.

In a manner analogous to that described in Example 1, starting with (1-methyl-1,2,3,4-tetrahydrobenzo[e][1,4]diazepin-5-ylidenemethyl)phosphonic acid diethyl ester (prepared as described in Example 1), and the appropriate aldehyde, prepared in a similar fashion to that for Example 53, the compounds shown in Table 8 were also prepared:

TABLE 8

| Compound | Structure | Name | MS (ES) (M + H)+ |
|---|---|---|---|
| Example 54 | 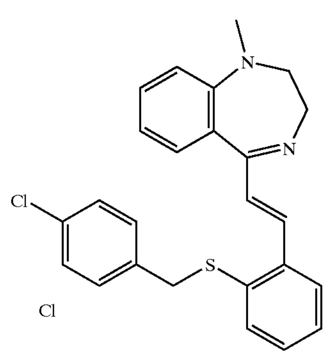 | (E)-5-[2-(4-Chlorobenzylthio)-styryl]-2,3-dihydro-1-methyl-1H-1,4-benzodiazepine dihydrochloride | 418.9 |

TABLE 8-continued

| Compound | Structure | Name | MS (ES) (M + H)+ |
|---|---|---|---|
| Example 55 | 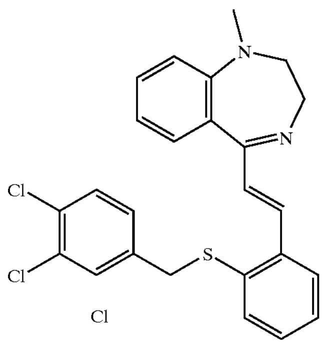 | (E)-5-[2-(3,4-Dichlorobenzylthio)-styryl]-2,3-dihydro-1-methyl-1H-1,4-benzodiazepine dihydrochloride | 452 (M$^+$; EI) |
| Example 56 | 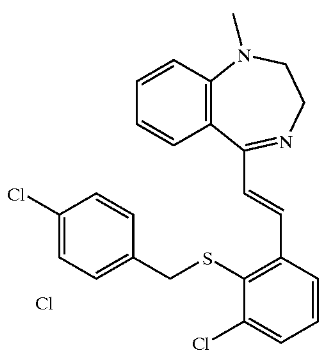 | 5-[3-Chloro-2-(4-chlorobenzylthio)-styryl]-2,3-dihydro-1-methyl-1H-1,4-benzodiazepine dihydrochloride | 453 (M$^+$) |
| Example 57 | 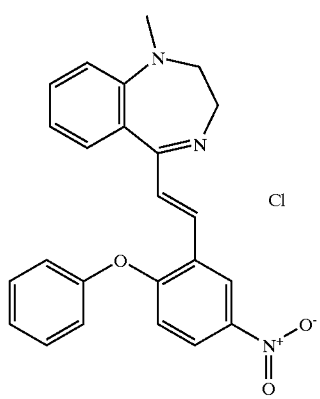 | (E)-2,3-Dihydro-1-methyl-5-(5-nitro-2-phenoxystyryl)-1H-1,4-benzodiazepine dihydrochloride | 399 (M$^+$; EI) |
| Example 58 | 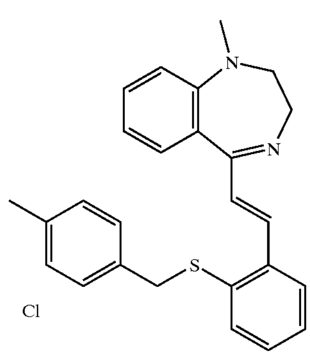 | (E)-2,3-Dihydro-1-methyl-5-[2-(4-methylbenzylthio)-styryl]-1H-1,4-benzodiazepine dihydrochloride | 399 |

TABLE 8-continued

| Compound | Name | MS (ES) (M + H)+ |
|---|---|---|
| Example 59 | (E)-2,3-Dihydro-5-[2-(4-methoxybenzyl-thio)styryl]-1-methyl-1H-1,4-benzo-diazepine dihydrochloride | 415 |
| Example 60 | (E)-5-[2-(4-Chlorophenoxy)-5-nitrostyryl]-3,4-dihydro-1-methyl-1H-1,4-benzodiazepine hydrochloride | 434.2 |
| Example 61 | (E)-5-[2-(4-tert-Butyl-benzylthio)styryl]-2,3-dihydro-1-methyl-1H-1,4-benzodiazepine dihydrochloride | 440 (M+; EI) |
| Example 62 | (E)-5-[2-[3-(Trifluoromethyl)benzyl-thio]styryl]-2,3-dihydro-1-methyl-1H-1,4-benzodiazepine dihydrochloride | 452 (M+; EI) |

TABLE 8-continued

| Compound | Name | MS (ES) (M + H)+ |
|---|---|---|
| Example 63 | (E)-5-[4-Bromo-2-(4-chlorobenzylthio)styryl]-2,3-dihydro-1-methyl-1H-1,4-benzodiazepine dihydrochloride | 496 (M+; EI) |
| Example 64 | (E)-2,3-Dihydro-1-methyl-5-[5-nitro-2-(3-phenylpropylthio)-styryl]-1H-1,4-benzodiazepine | 458.0 |
| Example 65 | (E)-2,3-Dihydro-1-methyl-5-(2-pentylthiostyryl)-1H-1,4-benzodiazepine | 365.3 |

EXAMPLE 66

(E)-5-[2-Chloro-6-(4-chlorobenzylthio)styryl]-2,3-dihydro-1-methyl-1H-1,4-benzodiazepine hydrochloride In an analogous fashion to Example 53 by replacing 2-fluorobenzaldehyde by 2-chloro-6-nitrobenzaldehyde and benzyl mercaptan with 4-chlorobenzyl mercaptan there was obtained (E)-5-[2-chloro-6-(4-chlorobenzylthio)styryl]-2,3-dihydro-1-methyl-1H-1,4-benzodiazepine hydrochloride MS: m/e 452 [M+H]+.

EXAMPLE 67

2[2-(2,3-Dihydro-1-methyl-1H-1,4-benzodiazepin-5-yl)vinyl]-N-methyl-4-nitroaniline dihydrochloride To a solution of 145 mg (0.47 mmol) of (1-methyl-1,2,3,4-tetrahydrobenzo[e][1,4]diazepin-5-ylidenemethyl) phosphonic acid diethyl ester (prepared as described in Example 1) in 3 ml of tetrahydrofuran was added 33 mg (0.82 mmol) of sodium hydride (60% dispersion in mineral oil). After 5 minutes 133 mg (0.49 mmol) of 2-(benzylmethylamino)-5-nitrobenzaldehyde was added and the mixture was stirred for 0.7 hours. The product was purified by column chromatography (20 g IST pre-packed column) eluting with 2% methanol/dichloromethane and treated with 0.25 ml of 4M hydrogen chloride in dioxan. The solvent was evaporated to leave 228 mg of 2-[2-(2,3-dihydro-1-methyl-1H-1,4-benzodiazepin-5-yl)vinyl]-N-methyl-4-nitroaniline dihydrochloride as an orange solid; MS: m/e 427 [M+H]+.

The starting material was prepared as follows:

A mixture of 300 mg (1.62 mmol) of 2-chloro-5-nitrobenzaldehyde, 196 mg (1.62 mmol) of N-benzylmethylamine and 268 mg (1.94 mmol) of potassium carbonate in dimethylformamide was heated at 80° C. for 5 hour. The solvent was removed and the residue was partitioned between water and ethyl acetate (×2). The combined organic phases were evaporated and the residue was purified by column chromatography eluting with 25% ethyl acetate/petroleum ether (40–60° C.) to give 290 mg of 2-(benzylmethylamino)-5-nitrobenzaldehyde as a yellow oil which solidified on standing; MS: m/e 270.9 [M+H]$^+$.

EXAMPLE 68

(E)-4'-[2-[2-(2,3-Dihydro-1-methyl-1H-1,4-benzodiazepin-5-yl)vinyl]phenylthio]acetanilide dihydrochloride To a mixture of 56 mg of 2-fluorobenzaldehyde (0.45 mmol) and 75 mg (0.45 mmol) of 4-acetamidothiophenol in 2.5 ml of dimethylformamide was added 62 mg of potassium carbonate. The mixture was heated at 65° C. for 0.75 hours then allowed to cool. To the mixture was added 112 mg (0.36 mmol) of (1-methyl-1,2,3,4-tetrahydrobenzo[e][1,4]diazepin-5-ylidenemethyl)phosphonic acid diethyl ester (prepared as described in Example 1) was added followed by 25 mg (0.63 mmol) of sodium hydride (60% dispersion in mineral oil). The mixture was stirred for 1 hour. The product was purified by column chromatography (20 g IST prepacked column) eluting with 1–6% methanol/ethyl acetate and treated with 0.15 ml of 4M hydrogen chloride in dioxan. The solvent was evaporated to leave 20 mg of a red gum which was recrystallised from methanol/acetone/petroleum ether (40–60° C.) to give 2 mg of (E)-4'-[2-[2-(2,3-dihydro-1-methyl-1H-1,4-benzodiazepin-5-yl)vinyl]phenylthio]acetanilide dihydrochloride as dark red powder; MS: m/e 428 [M+H]$^+$.

In a manner analogous to that described in Example 1, starting with (1-methyl-1,2,3,4-tetrahydrobenzo[e][1,4]diazepin-5-ylidenemethyl)phosphonic acid diethyl ester (prepared as described in Example 1), and the appropriate aldehyde, prepared in a similar fashion to that for Example 68, the compounds shown in Table 9 were also prepared:

TABLE 9

| Example 69 | 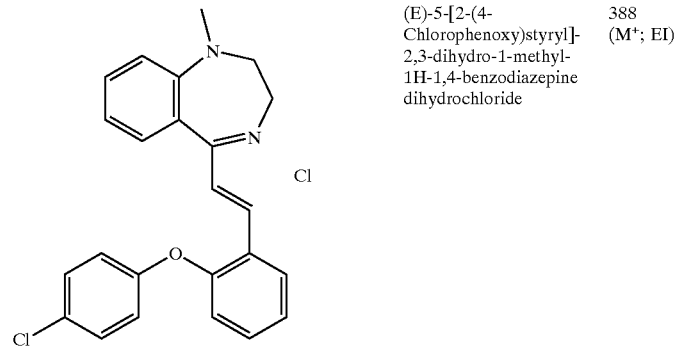 | (E)-5-[2-(4-Chlorophenoxy)styryl]-2,3-dihydro-1-methyl-1H-1,4-benzodiazepine dihydrochloride | 388 (M$^+$; EI) |
| --- | --- | --- | --- |
| Example 70 | 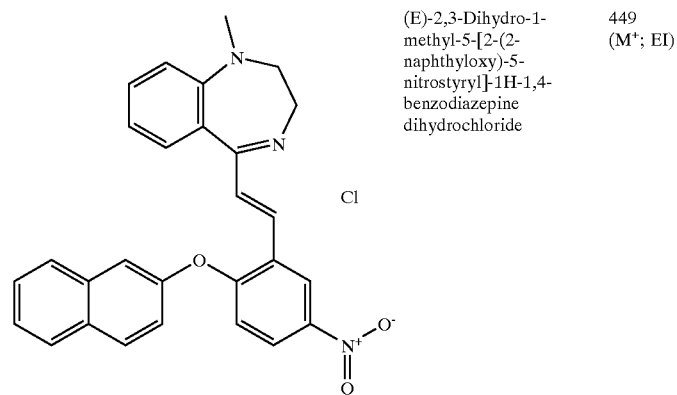 | (E)-2,3-Dihydro-1-methyl-5-[2-(2-naphthyloxy)-5-nitrostyryl]-1H-1,4-benzodiazepine dihydrochloride | 449 (M$^+$; EI) |

TABLE 9-continued

| | | | |
|---|---|---|---|
| Example 71 | | (E)-2,3-Dihydro-1-methyl-5-[2-(1-naphthyloxy)-5-nitrostyryl]-1H-1,4-benzodiazepine dihydrochloride | 450 (M+) |
| Example 72 | | (E)-2,3-Dihydro-1-methyl-5-(2-p-tolylthiostyryl)-1H-1,4-benzodiazepine dihydrochloride | 385 |
| Example 73 | | (E)-2,3-Dihydro-5-[2-(4-methoxyphenylthio)styryl]-1-methyl-1H-1,4-benzodiazepine dihydrochloride | 400 (M+; EI) |
| Example 74 | | (E)-2,3-Dihydro-1-methyl-5-[2-(2-naphthylthio)styryl]-1H-1,4-benzodiazepine dihydrochloride | 420 (M+; EI) |

EXAMPLE 75

(E)-2,3-Dihydro-1-methyl-5-[2-[(2-naphthyl)methoxy]styryl]-1H-1,4-benzodiazepine dihydrochloride To a mixture of 55 mg (0.45 mmol) of 2-hydroxybenzaldehyde and 99 mg (0.45 mmol) of 2-bromomethylnaphthalene in 3 ml of tetrahydrofuran was added 124 mg (0.90 mmol) of potassium carbonate. The mixture was heated at 65° C. for 18 hours before 112 mg (0.36 mmol) of (1-methyl-1,2,3,4-tetrahydrobenzo[e][1,4]diazepin-5-ylidenemethyl)phosphonic acid diethyl ester (prepared as described in Example 1) was added followed by 25 mg (0.63 mmol) of sodium hydride (60% dispersion in mineral oil). The mixture was stirred for 18 hours. The mixture was purified by column chromatography (20 g IST pre-packed column) eluting with 2% methanol/ethyl acetate and treated with 0.15 ml of 4M hydrogen chloride in dioxan. The solvent was evaporated and the residue was recrystallised from methanol/ethyl acetate/ether to give 63 mg of (E)-2,3-dihydro-1-methyl-5-[2-[(2-naphthyl)methoxy] styryl]-1H-1,4-benzodiazepine dihydrochloride as an orange solid; MS: e/z 419 [M+S]$^+$.

In a manner analogous to that described in Example 75, starting with (1-methyl-1,2,3,4-tetrahydrobenzo[e][1,4]diazepin-5-ylidenemethyl)phosphonic acid diethyl ester (prepared as described in Example 1), and the appropriate aldehyde, prepared in a similar fashion to that for Example 75, the compounds shown in Table 10 were also prepared:

TABLE 10

| Compound | Structure | Name | MS (ES) (M + H)$^+$ |
|---|---|---|---|
| Example 76 | 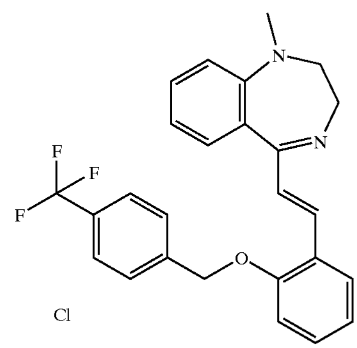 | (E)-5-[2-[4-(Trifluoromethyl)benzyloxy]styryl]-2,3-dihydro-1-methyl-1H-1,4-benzodiazepine dihydrochloride | 437 |
| Example 77 | 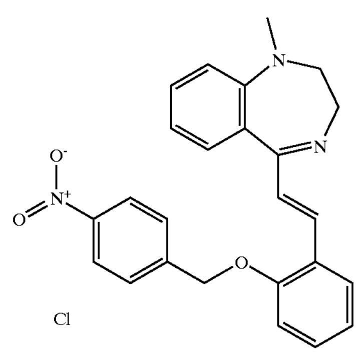 | (E)-2,3-Dihydro-1-methyl-5-[2-(4-nitrobenzyloxy)styryl]-1H-1,4-benzodiazepine dihydrochloride | 413 (M$^+$; EI) |
| Example 78 | 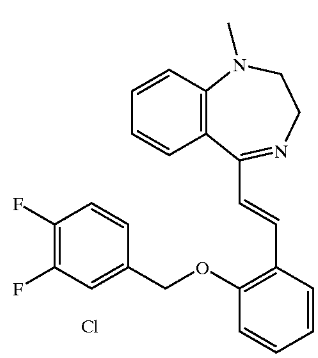 | (E)-5-[2-(3,4-Difluorobenzyloxy)-styryl]-2,3-dihydro-1-methyl-1H-1,4-benzodiazepine dihydrochloride | 334 (M$^+$; EI) |

TABLE 10-continued

| Compound | Name | MS (ES) (M + H)+ |
|---|---|---|
| Example 79 | (E)-5-(2-Benzyloxy-styryl)-2,3-dihydro-1-methyl-1H-1,4-benzodiazepine dihydrochloride | 369 |
| Example 80 | (E)-5-[2-(4-Chloro-benzyloxy)styryl]-2,3-dihydro-1-methyl-1H-1,4-benzodiazepine dihydrochloride | 402 (M+; EI) |
| Example 81 | (E)-4-(4-Chlorobenzyloxy)-3-[2-(2,3-dihydro-1-methyl-1H-1,4-benzodiazepin-5-yl)vinyl]-N,N-diethylaniline dihydrochloride | 474 |

EXAMPLE 82

(E)-4-Benzylthio-3-[2-(2,3-dihydro-1-methyl-1H-1,4-benzodiazepin-5-yl)vinyl]aniline dihydrochloride To 215 mg (0.50 mmol) of (E)-5-(2-benzylthio-5-nitrostyryl)-2,3-dihydro-1-methyl-1H-1,4-benzodiazepine dihydrochloride (prepared as described in Example 15) in 8 ml of tetrahydrofuran and 8 ml of ethanol was added 380 mg (0.90 mmol) of tin (II) chloride and 0.48 ml of concentrated hydrochloric acid. The mixture was heated at 60° C. for 7 hours. The solution was reduced to half volume and partitioned between 50 ml of saturated sodium hydrogen carbonate solution and 100 ml and 50 ml of dichloromethane. The combined organic phases were dried (magnesium sulphate), filtered and evaporated. The residue was purified by column chromatography eluting with 2–5% methanol/dichloromethane and treated with 0.30 ml of 4M hydrogen chloride in dioxan. The solvent was evaporated and the residue was recrystallised from methanol/ether to give 46 mg of (E)-4-benzylthio-3-[2-(2,3-dihydro-1-methyl-1H-1,4-benzodiazepin-5-yl)vinyl]aniline dihydrochloride as dark red crystals; MS: m/e 400 [M+H]+.

EXAMPLE 83

(E)-3-[2-(2,3-Dihydro-1-methyl-1H-1,4-benzodiazepin-5-yl)vinyl]-4-(3-phenylpropylthio) aniline hydrochloride In an analogous fashion to Example 82 from (E)-2,3-dihydro-1-methyl-5-[5-nitro-2-(3-phenylpropylthio)styryl]-1H-1,4-benzodiazepine (prepared as described in Example 75) there was obtained (E)-3-[2-(2,3-dihydro-1-methyl-1H-1,4-benzodiazepin-5-yl)vinyl]-4-(3-phenylpropylthio) aniline hydrochloride as a dark red solid MS: m/e 428.0 [M+H]+.

EXAMPLE 84

(E)-2-Acetamido-4'-benzylthio-3'-[2-(2,3-dihydro-1-methyl-1H-1,4-benzodiazepin-5-yl)vinyl]acetanilide dihydrochloride

To a mixture of 58 mg (0.114 mmol) of (E)-4-benzylthio-3-[2-(2,3-dihydro-1-methyl-1H-1,4-benzodiazepin-5-yl)vinyl]aniline dihydrochloride (prepared as described in Example 82), 20 mg (0.171 mmol) of N-acetylglycine and 1-hydroxy-7-azabenzotriazole in 5 ml of dimethylformamide was added 44 mg (0.228 mmol) of 1-[3-(dimethylamino)propyl]-3-ethylcarbodiimide hydrochloride. The mixture was stirred for 4 hours. The solvent was removed and the residue was purified by column chromatography eluting with 5–20% methanol/dichloromethane and treated with 0.10 ml of 4M hydrogen chloride in dioxan. The solvent was evaporated and the residue was recrystallised from acetone/methanol/diethyl ether to give 10 mg of (E)-2-acetamido-4'-benzylthio-3'-[2-(2,3-dihydro-1-methyl-1H-1,4-benzodiazepin-5-yl)vinyl]acetanilide dihydrochloride as a yellow solid; MS: m/e 499 (M+).

EXAMPLE 85

(E)-2,3-Dihydro-1-methyl-5-[3-[(2-pyridyl)methoxy]styryl]-1H-1,4-benzodiazepine dihydrochloride

To a mixture of 74 mg (0.266 mmol) of (E)-3-[2-(2,3-dihydro-1-methyl-1H-1,4-benzodiazepin-5-yl)vinyl]phenol and 29 mg (0.266 mmol) of 2-pyridylmethanol in 4 ml of tetrahydrofuran was added 134 mg (0.40 mmol) of polymer supported triphenylphosphine followed by 91 mg (0.40 mmol) of di-tert-butylazodicarboxylate. After 19 hours a further 134 mg (0.40 mmol) of polymer supported triphenylphosphine was added and the mixture was stirred for 72 hours. The mixture was filtered and the product was purified by column chromatography (20 g IST pre-packed column) eluting with 5% methanol/ethyl acetate and treated with 0.15 ml of 4M hydrogen chloride in dioxan. The solvent was evaporated and the residue lyophilised to give 26 mg of (E)-2,3-dihydro-1-methyl-5-[3-[(2-pyridyl)methoxy]styryl]-1H-1,4-benzodiazepine dihydrochloride as a dark red solid; MS: m/e 370 [M+H]+.

The starting material, (E)-3-[2-(2,3-dihydro-1-methyl-1H-1,4-benzodiazepin-5-yl)vinyl]phenol was prepared in an analogous fashion to Example 1, replacing 3,4-difluorobenzaldehyde by 2-hydroxybenzaldehyde.

In a manner analogous to that described in Example 85, starting with (E)-3-[2-(2,3-dihydro-1-methyl-1H-1,4-benzodiazepin-5-yl)vinyl]phenol and the appropriate alcohol, the compounds shown in Table 11 were also prepared:

TABLE 11

| Compound | Structure | Name | MS (ES) (M + H)+ |
|---|---|---|---|
| Example 86 | 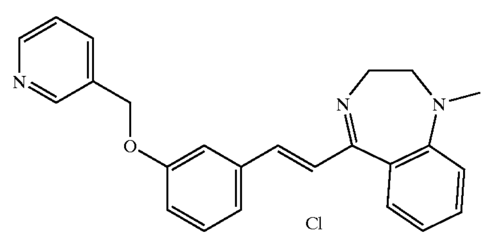 | (E)-2,3-Dihydro-1-methyl-5-[3-[(3-pyridyl)methoxy]-styryl]-1H-1,4-benzodiazepine dihydrochloride | 370 |
| Example 87 | 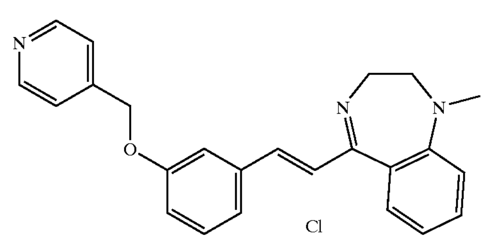 | (E)-2,3-Dihydro-1-methyl-5-[3-[(4-pyridyl)methoxy]-styryl]-1H-1,4-benzodiazepine dihydrochloride | 370 |
| Example 88 | 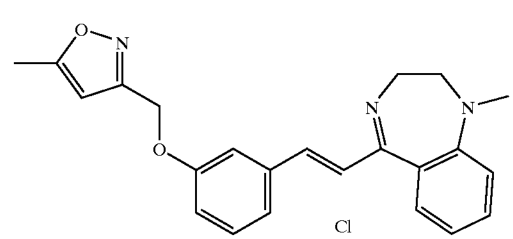 | (E)-2,3-Dihydro-1-methyl-5-[3-[(5-methyl-3-isoxazolyl)-methoxy]styryl]-1H-1,4-benzodiazepine dihydrochloride | 374 |

TABLE 11-continued

| Compound | Name | MS (ES) (M + H)+ |
|---|---|---|
| Example 89 | (E)-5-[3-[(1-Benzyl-1H-imidazol-2-yl)methoxy]styryl]-2,3-dihydro-1-methyl-1H-1,4 benzodiazepine dihydrochloride | 448 (M+; EI) |
| Example 90 | (E)-5-[2,3-Dihydro-3-(4-methoxybenzyl-oxy)styryl]-1-methyl-1H-1,4-benzodiazepine dihydrochloride | 398 (M+; EI) |
| Example 91 | Methyl (E)-4-[[3-[2-(2,3-dihydro-1-methyl-1H-1,4-benzodiazepin-5-yl)vinyl]phenoxy]-methyl]benzoate dihydrochloride | 426 (M+; EI) |
| Example 92 | (E)-2,3-Dihydro-1-methyl-5-[3-[(3,5-dimethyl-1-pyrazolyl)methoxy]-styryl]-1H-1,4-benzodiazepine dihydrochloride | 387 |
| Example 93 | (E)-4'-[[3-[2-(2,3-Dihydro-1-methyl-1H-1,4-benzo-diazepin-5-yl)vinyl]phenoxy]-methyl]acetanilide hydrochloride | 426 |

EXAMPLE 94

(E)-5-[2-(4-Chlorophenoxy)styrl]-8-fluoro-2,3-dihydro-1-methyl-1H-1,4-benzodiazepine dihydrochloride To a mixture of 56 mg (0.45 mmol) of 2-fluorobenzaldehyde and 64 mg (50 mmol) of 4-chlorophenol in 2.5 ml of dimethylformamide was added 75 mg (0.54 mmol) of sodium hydrogen carbonate. The mixture was heated at 95° C. for 18 hours. To the mixture at ambient temperature was added 118 mg (0.36 mmol) of (8-fluoro-1-methyl-1,2,3,4-tetrahydrobenzo[e][1,4] diazepin-5-ylidenemethyl)phosphonic acid diethyl ester followed by 25 mg (0.63 mmol) of sodium hydride (60% dispersion in mineral oil). The mixture was stirred for 2 hours. The mixture was partitioned between 12 ml of water and 3×4 ml of dichloromethane. The combined organic portions were dried (magnesium sulphate), filtered and evaporated. The product was purified by column chromatography (20 g IST pre-packed column) eluting with ethyl acetate and treated with 0.15 ml of 4M hydrogen chloride in dioxan. The solvent was evaporated to leave a red gum which was recrystallised from acetone/ethyl acetate/diethyl ether to give 17 mg of (E)-5-[2-(4-chlorophenoxy)styryl]-8-fluoro-2,3-dihydro-1-methyl-1H-1,4-benzodiazepine dihydrochloride as a red solid; MS: m/e 452 (M⁺).

The starting material (8-fluoro-1-methyl-1,2,3,4-tetrahydrobenzo[e][1,4]-diazepin-5-ylidenemethyl)phosphonic acid diethyl ester was prepared in an analogous fashion to (1-methyl-1,2,3,4-tetrahydrobenzo[e][1,4]diazepin-5-ylidenemethyl)phosphonic acid diethyl ester, as described in Example 1 by replacing 2-fluorobenzoic acid with 2,4-difluorobenzoic acid.

EXAMPLE 95

(E)-5-[3-Chloro-2-(3,4-dichlorobenzylthio)styryl]-8-fluoro-2,3-dihydro-1-methyl-1H-1,4-benzodiazepine dihydrochloride To a mixture of 71 mg of 3-chloro-2-fluorobenzaldehyde (0.45 mmol) and 96 mg (0.45 mmol) of 3,4-dichlorobenzyl mercaptan in 3 ml of tetrahydrofuran was added 22 mg of sodium hydride (60% dispersion in mineral oil). After 3 hours 118 mg (0.36 mmol) of (8-fluoro-1-methyl-1,2,3,4-tetrahydrobenzo[e][1,4]diazepin-5-ylidenemethyl)phosphonic acid diethyl ester (prepared as described in Example 94) was added followed by 25 mg (0.63 mmol) of sodium hydride (60% dispersion in mineral oil). The mixture was stirred for 1 hour. The product was purified by column chromatography (20 g IST pre-packed column) eluting with ethyl acetate and treated with 0.15 ml of 4M hydrogen chloride in dioxan. The solvent was evaporated to leave 113 mg of an orange gum which was recrystallised from methanol/acetone/petroleum ether (40–60° C.) to give 44 mg of (E)-5-[3-chloro-2-(3,4-dichlorobenzylthio)styryl]-8-fluoro-2,3-dihydro-1-methyl-1H-1,4-benzodiazepine dihydrochloride as an orange solid; MS: m/e 402 (M)⁺.

EXAMPLE 96

(E)-5-(2Benzylthiostyryl)-8-fluoro-2,3-dihydro-1-methyl-1H-4-benzodiazepine dihydrochloride In a manner analogous to that described in Example 95, by replacing 3,4-dichlorobenzyl mercaptan with benzyl mercaptan and 3-chloro-2-fluorobenzaldehyde with 2-fluorobenzaldehyde there was obtained (E)-5-(2-benzylthiostyryl)-8-fluoro-2,3-dihydro-1-methyl-1H-1,4-benzodiazepine dihydrochloride MS: m/e 504 (M⁺).

EXAMPLE 97

(E)-5-(2-Benzylthio-5-nitrostyryl)-8-fluoro-2,3-dihydro-1-methyl-1H-1,4-benzodiazepine dihydrochloride In an analogous fashion to Example 1 and by replacing (1-methyl-1,2,3,4-tetrahydrobenzo[e][1,4]diazepin-5-ylidenemethyl)phosphonic acid diethyl ester with (8-fluoro-1-methyl-1,2,3,4-tetrahydrobenzo[e][1,4]diazepin-5-ylidenemethyl)phosphonic acid diethyl ester (prepared as described in Example 94), and 3,4-difluorobenzaldehyde with 2-benzylthio-5-nitrobenzaldehyde there was obtained (E)-5-(2-benzylthio-5-nitrostyryl)-8-fluoro-2,3-dihydro-1-methyl-1H-1,4-benzodiazepine dihydrochloride; MS: m/e 448 (M⁺H).

EXAMPLE 98

(E)-5-(3,4-Dichlorostyryl)-2,3-dihydro-8-(3-methoxyphenyl)-1-methyl-1H-1,4-benzodiazepine dihydrochloride To 100 mg (0.24 mmol) of [8-(3-methoxyphenyl)-1-methyl-1,2,3,4-tetrahydrobenzo[e][1,4]diazepin-5-ylidenemethyl]phosphonic acid diethyl ester in 2 ml of tetrahydrofuran was added 17 mg (0.42 mmol) of sodium hydride (60% dispersion in mineral oil). After 10 minutes 44 mg (0.25 mmol) of 3,4-dichlorobenzaldehyde was added and the mixture was stirred for 3 hours. The product was purified by column chromatography (20 g IST pre-packed column) eluting with 1% methanol/ethyl acetate and treated with 0.10 ml of 4M hydrogen chloride in dioxan. The solvent was evaporated to leave a red gum which was recrystallized from ethyl acetate to give 25 mg of (E)-5-(3,4-dichlorostyryl)-2,3-dihydro-8-(3-methoxyphenyl)-1-methyl-1H-1,4-benzodiazepine dihydrochloride as an orange solid; MS: m/e 436 (M⁺).

The starting material was prepared as follows:

To 300 mg (0.77 mmol) of (8-bromo-1-methyl-1,2,3,4-tetrahydrobenzo[e][1,4]diazepin-5-ylidenemethyl)phosphonic acid diethyl ester (prepared as described in Example 41) in 1 ml of dioxane was added 123 mg (0.81 mmol) of 3-methoxyphenylboronic acid, 7.8 mg (0.028 mmol) of tricyclohexylphosphine, 10.5 mg 0.012 mmol) of tris-(dibenzylideneacetone)-palladium (0) and 141 mg of caesium fluoride. The mixture was heated at 80° C. for 6 hours. The mixture was partitioned between ethyl acetate and water. The organic phase was evaporated and the product was purified by column chromatography (20 g IST pre-packed column) eluting with acetone—petroleum ether (40–60° C.) (1:2) to give 217 mg of [8-(3-methoxyphenyl)-1-methyl-1,2,3,4-tetrahydrobenzo[e][1,4]diazepin-5-ylidenemethyl]phosphonic acid diethyl ester as a yellow gum; MS: m/e 417 (M⁺).

EXAMPLE 99

(E)-5-(3,4-Dichlorostyryl)-2,3-dihydro-1-methyl-8-phenyl-1H-1,4-benzodiazepine dihydrochloride To 105 mg (0.25 mmol) of (1-methyl-8-phenyl-1,2,3,4-tetrahydrobenzo[e][1,4]diazepin-5-ylidenemethyl) phosphonic acid diethyl ester in 2 ml of tetrahydrofuran was added 18 mg (0.42 mmol) of sodium hydride (60% dispersion in mineral oil). After 10 minutes 112 mg (0.64 mmol) of 3,4-dichlorobenzaldehyde was added and the mixture was stirred for 18 hours. The product was purified by column chromatography (50 g IST pre-packed column) eluting with 2% methanol/dichloromethane and treated with 0.15 ml of 4M hydrogen chloride in dioxan. The solvent was evaporated and the residue was recrystallized from acetone/petroleum ether (40–60° C.) to give 40 mg of (E)-5-(3,4-dichlorostyryl)-2,3-dihydro-8-(3-methoxyphenyl)-1-methyl-1H-1,4-benzodiazepine dihydrochloride as an orange solid; MS: m/e 406 (M⁺).

The starting material was prepared as follows:

To 286 mg (0.83 mmol) of (8-chloro-1-methyl-1,2,3,4-tetrahydrobenzo[e][1,4]diazepin-5-ylidenemethyl) phosphonic acid diethyl ester (prepared as described in Example 48) in 1 ml of dioxane was added 106 mg (0.87 mmol) of phenylboronic acid, 8.4 mg (0.03 mmol) of tricyclohexylphosphine, 11.5 mg 0.013 mmol)of tris-(dibenzylideneacetone)-palladium (0) and 152 mg of caesium fluoride. The mixture was heated at 80° C. for 14 hours. The mixture was purified by column chromatography (20 g IST pre-packed column) eluting with acetone—petroleum ether (40–60° C.) (1:2) to give 227 mg of (1-methyl-8-phenyl-1,2,3,4-tetrahydro-benzo[e][1,4]diazepin-5-ylidenemethyl)phosphonic acid diethyl ester as a yellow oil; MS: m/e 387 [M+H]⁺.

EXAMPLE 100

(E)-5-[2-(4-Chlorophenylthio)styryl]-2,3-dihydro-8-(3-methoxyphenyl)-1-methyl-1H-1,4-benzodiazepine dihydrochloride To 112 mg (0.27 mmol) of [8-(3-methoxyphenyl)-1-methyl-1,2,3,4-tetrahydro-benzo[e][1,4]diazepin-5- ylidenemethyl]phosphonic acid diethyl ester (prepared as described in Example 98) in 2 ml of tetrahydrofuran was added 19 mg (0.47 mmol) of sodium hydride (60% dispersion in mineral oil). After 10 minutes 70 mg (0.28 mmol) of 2-(4-chlorophenylthio)benzaldehyde was added and the mixture was stirred for 3 hours. The product was purified by column chromatography (20 g IST pre-packed column) eluting with 1% methanol/ethyl acetate and treated with 0.10 ml of 4M hydrogen chloride in dioxan. The solvent was evaporated to leave an orange gum which was recrystallized from ethyl acetate to give 10 mg of (E)-5-[2-(4-chlorophenylthio)styryl]-2,3-dihydro-8-(3-methoxyphenyl)-1-methyl-1H-1,4-benzodiazepine dihydrochloride as a red solid; MS: m/e 510 (M+).

EXAMPLE 101

(E)-5-(3,4-Dichlorostyryl)-2,3-dihydro-1-methyl-8-(3-thienyl)-1H-1,4-benzodiazepine dihydrochloride To 105 mg (0.27 mmol) of (1-methyl-8-thiophen-3-yl-1,2,3,4-tetrahydrobenzo[e][1,4]diazepin-5-ylidenemethyl)phosphonic acid diethyl ester in 2 ml of tetrahydrofuran was added 19 mg (0.47 mmol) of sodium hydride (60% dispersion in mineral oil). After 10 minutes 49 mg (0.28 mmol) of 3,4-dichlorobenzaldehyde was added and the mixture was stirred for 3 hours. The product was purified by column chromatography (20 g IST pre-packed column) eluting with 1% methanol/dichloromethane and treated with 0.15 ml of 4M hydrogen chloride in dioxan. The solvent was evaporated and the residue was recrystallized from acetone to give 75 mg of (E)-5-(3,4-dichlorostyryl)-2,3-dihydro-1-methyl-8-(3-thienyl)-1H-1,4-benzodiazepine dihydrochloride as an orange solid; MS: 412 (M+).

The starting material was prepared as follows:

To 300 mg (0.77 mmol) of (8-bromo-1-methyl-1,2,3,4-tetrahydrobenzo[e][1,4]diazepin-5-ylidenemethyl)phosphonic acid diethyl ester (prepared as described in Example 41) in 2 ml of dioxane was added 116 mg (0.81 mmol) of thiophene-3-boronic acid, 8 mg (0.028 mmol) of tricyclohexylphosphine, 10.8 mg 0.012 mmol) of tris-(dibenzylideneacetone)-palladium (0) and 140 mg of caesium fluoride. The mixture was heated at 80° C. for 6 hours. The mixture was partitioned between ethyl acetate and water. The organic phase was evaporated and the product was purified by column chromatography (20 g IST pre-packed column) eluting with acetone—petroleum ether (40–60° C.) (1:3) to give 185 mg of (1-methyl-8-thiophen-3-yl-1,2,3,4-tetrahydrobenzo[e][1,4]diazepin-5-ylidenemethyl)phosphonic acid diethyl ester as a yellow gum; MS: m/e 393 [M+H]+.

EXAMPLE 102

(E)-5-(3,4-Dichlorostyryl)-2,3-dihydro-9-phenyl-1H-1,4-benzodiazepine hydrochloride In an analogous fashion to Example 101, by replacing (8-bromo-1-methyl-1,2,3,4-tetrahydrobenzo[e][1,4]diazepin-5-ylidenemethyl)phosphonic acid diethyl ester with (9-chloro-1,2,3,4-tetrahydrobenzo[e][1,4]diazepin-5-ylidenemethyl)phosphonic acid diethyl ester (prepared as described in Example 45) and thiophene-3-boronic acid with phenylboronic acid, there was obtained (E)-5-(3,4-dichlorostyryl)-2,3-dihydro-9-phenyl-1H-1,4-benzodiazepine hydrochloride as a red foam MS: m/e 393.2 [M+H]+.

EXAMPLE 103

(E)-5-(3,4-Dichlorostyryl)-2,3-dihydro-9-(4-methoxyphenyl)-1H-1,4-benzodiazepine hydrochloride In an analogous fashion to Example 101, by replacing (8-bromo-1-methyl-1,2,3,4-tetrahydrobenzo[e][1,4]diazepin-5-ylidenemethyl)phosphonic acid diethyl ester by (9-chloro-1,2,3,4-tetrahydrobenzo[e][1,4]diazepin-5-ylidenemethyl)phosphonic acid diethyl ester (prepared as described in Example 45) and thiophene-3-boronic acid by 4-methoxyphenylboronic acid, there was obtained (E)-5-(3,4-dichlorostyryl)-2,3-dihydro-9-(4-methoxyphenyl)-1H-1,4-benzodiazepine hydrochloride as a red foam MS: m/e 423.2 [M+H]+.

EXAMPLE 104

(E)-5-[2-(4-Chlorophenylthio)styryl]-2,3-dihydro-1-methyl-8-(3-thienyl)-1H-1,4-benzodiazepine dihydrochloride To 105 mg (0.27 mmol) of (1-methyl-8-thiophen-3-yl-1,2,3,4-tetrahydrobenzo[e][1,4]diazepin-5-ylidenemethyl)phosphonic acid diethyl ester (prepared as described in Example 101) in 2 ml of tetrahydrofuran was added 19 mg (0.47 mmol) of sodium hydride (60% dispersion in mineral oil). After 10 minutes 70 mg (0.28 mmol) of 3,4-dichlorobenzaldehyde was added and the mixture was stirred for 3 hours. The product was purified by column chromatography (20 g IST pre-packed column) eluting with 1% methanol/dichloromethane and treated with 0.15 ml of 4M hydrogen chloride in dioxan. The solvent was evaporated and the residue was recrystallized from ethyl acetate to give 32 mg of (E)-5-[2-(4-chlorophenylthio)styryl]-2,3-dihydro-1-methyl-8-(3-thienyl)-1H-1,4-benzodiazepine dihydrochloride as an orange solid; MS: m/e 486 (M+).

EXAMPLE 105

(E)-5-(3,4-Dichlorostyryl)-2,3-dihydro-1-methyl-8-vinyl-1H-1,4-benzodiazepine dihydrochloride To 123 mg (0.32 mmol) of (8-bromo-1-methyl-1,2,3,4-tetrahydrobenzo[e][1,4]diazepin-5-ylidenemethyl)phosphonic acid diethyl ester (prepared as described in Example 41) in 2 ml of dioxane was added 120 mg (0.38 mmol) of vinyl tributylstannane, followed by 11.1 mg (0.016 mmol)of palladium (II) bis-triphenylphosphine-dichloride. The mixture was heated at 80° C. for 18 hours. To the mixture at ambient temperature was added 22 mg (0.55 mmol) of sodium hydride (60% dispersion in mineral oil). After 5 minutes 57 mg (0.33 mmol) of 3,4-dichlorobenzaldehyde was added and the mixture was stirred for 18 hours. The solvent was removed and the product was purified by column chromatography eluting with 1–4% methanol/dichloromethane and treated with 0.10 ml of 4M hydrogen chloride in dioxan. The solvent was evaporated and the residue was dissolved from acetone/petroleum ether (40 60° C.). The solvent was removed to give 25 mg of (E)-5-(3,4-dichlorostyryl)-2,3-dihydro-1-methyl-8-vinyl-1H-1,4-benzodiazepine dihydrochloride as a red solid; MS: 357 (M+).

EXAMPLE 106

(E)-5-[2-(4-Chlorophenylthio)styryl]-8-(2-furly)-2,3-dihydro-1-methyl-1H-1,4-benzodiazepine dihydrochloride To 123 mg (0.32 mmol) of (8-bromo-1-methyl-1,2,3,4-tetrahydrobenzo[e][1,4]diazepin-5-ylidenemethyl)phosphonic acid diethyl ester (prepared as described in Example 41) in 2 ml of dioxane was added 135 mg (0.38 mmol) of 2-(tributylstannyl)furan, followed by 11.1 mg (0.016 mmol) of palladium (II) bis-triphenylphosphinedichloride. The mixture was heated at 80° C. for 18 hours. To the mixture at ambient temperature was added 55 mg (1.37 mmol) of sodium hydride (60% dispersion in mineral oil). After 5 minutes 82 mg (0.33 mmol) of 2-(4-chlorophenylthio)benzaldehyde was added and the mixture was stirred for 18 hours. The solvent was removed and the product was purified by column chromatography eluting with 24–40% acetone/petroleum ether (40–60° C.) and treated with 0.10 ml of 4M hydrogen chloride in dioxan. The solvent was evaporated and the residue was dissolved from acetone/petroleum ether (40 60° C.). The solvent was removed and the residue was recrystallised from acetone/petroleum ether (40 60° C.) to give 63 mg of (E)-5-[2-(4-chlorophenylthio)styryl]-8-(2-furyl)-2,3-dihydro-1-methyl-1H-1,4-benzodiazepine dihydrochloride as dark red crystals; MS: m/e 471 (M+).

EXAMPLE 107

(E)-5-(3,4-Dichlorostyryl)-1,3-dihydro-1-methyl-2H-benzo-1,4-diazepin-2-one 65 mg (0.14 mmol) of (E)-N-[[N-[2-[3-(3,4-dichlorophenyl)acryloyl]phenyl]-N-methylcarbamoyl]methyl]pivalamide were dissolved in 5 ml of ethyl acetate saturated with hydrogen chloride and were stirred at room temperature for 30 minutes. The solvent was removed by evaporation and the residue dissolved in 5 ml of methanol and 40 mg (0.04 mmol) of triethylamine added. After 2 hours at room temperature the solvent was removed by evaporation and the residue chromatographed on silica gel using ethyl acetate/petrol 2:1 for the elution. There was obtained 33 mg of (E)-5-(3,4-dichlorostyryl)-1,3-dihydro-1-methyl-2H-benzo-1,4-diazepin-2-one as a pale yellow foam. MS: m/e 344.9 [M+H]+.

The starting material was prepared as follows:

404 mg (2 mmol) of bromoacetyl bromide were added to a stirred, ice-cooled solution of 298 mg (2 mmol) of 2'-(methylamino)acetophenone in 5 ml of dichloromethane. The mixture was stirred for 20 minutes then 2 ml of 1M sodium hydroxide solution were added and stirring was continued for a further 15 minutes. The resulting solution was washed with 2M hydrochloric acid and saturated sodium bicarbonate solution, dried over magnesium sulphate and evaporated to dryness to give 2.1 g of 2'-acetyl-2-bromo-N-methylacetanilide as a viscous gum. $^1$H NMR (400 MHz CDCl$_3$) δ: 2.54 (3H,s), 3.16 (3H,s), 3.45–3.52 (2H,q), 7.34 (1H,dd), 7.48 (1H,dt), 7.56 (1H,dt), 7.77 (1H, dd).

2.05 g (7.59 mmol) of 2'-acetyl-2-bromo-N-methylacetanilide and 2 g (30.77 mmol) of sodium azide were stirred in 20 ml of dimethylformamide at room temperature for 4 hours. The resulting mixture was diluted with water and extracted with diethyl ether. The organic phase was washed twice with water, dried over magnesium sulphate, evaporated to dryness and the residue chromatographed on silica gel using ethyl acetate/petrol 5:3 for the elution. There was obtained 910 mg of 2'-acetyl-2-azido-N-methylacetanilide as a colorless gum. MS: m/e 233 [M+H]+.

1.8 g (7.76 mmol) of 2'-acetyl-2-azido-N-methylacetanilide and 2 g (9.17 mmol) of di-tert-butyl dicarbonate were hydrogenated with 250 mg of 10% palladium on carbon in 50 ml of ethyl acetate for 45 minutes. The mixture was filtered, evaporated to dryness, dissolved in 5 ml of dichloromethane and left at room temperature for 24 hours. The solvent was removed by evaporation and the residue triturated with diethyl ether/petrol (1:1) and filtered. The filtrate was evaporated to dryness and chromatographed on silica gel using ethyl acetate/petrol (55:45) to give 171 mg of N-[[N-(2-acetylphenyl)-N-methylcarbamoyl]methyl]pivalamide as a gum. MS: m/e 307 [M+H]+.

5 drops of 3M sodium hydroxide solution were added to a mixture of 160 mg (0.52 mmol) of N-[[N-(2-acetylphenyl)-N-methylcarbamoyl]methyl]pivalamide and 100 mg (0.57 mmol) of 3,4-dichlorobenzaldehyde in 3 ml of methanol. After 1 hr at room temperature the solvent was removed by evaporation and the residue chromatographed on silica gel using ethyl acetate/petrol (55:45) for the elution. There was obtained 65 mg of (E)-N-[[N-[2-[3-(3,4-dichlorophenyl)acryloyl]phenyl]-N-methylcarbamoyl]methyl]pivalamide as a yellow gum. MS: m/e 463 [M+H]+.

EXAMPLE 108

(E)-1,3-Dihydro-5-styryl-2H-benzo-1,4-diazepin-2-one

In an analogous manner to Example 107 but replacing 2'-(methylamino)acetophenone with 2'-aminoacetophenone and 3,4-dichlorobenzaldehyde with benzaldehyde there was obtained (E)-1,3-dihydro-5-styryl-2H-benzo-1,4-diazepin-2-one as an off-white solid MS: m/e 263.4 [M+H]+.

EXAMPLE 109

(E)-5-(2,3-Dichlorostyryl)-1,3-dihydro-2H-1,4-benzodiazepin-2-one

In an analogous manner to Example 107 but replacing 2'-(methylamino)acetophenone with 2'-aminoacetophenone and 3,4-dichlorobenzaldehyde with 2,3-dichlorobenzaldehyde there was obtained (E)-5-(2,3-dichlorostyryl)-1,3-dihydro-2H-1,4-benzodiazepin-2-one as a light yellow solid MS: m/e 331.1 [M+H]+.

EXAMPLE 110

(E)-5-(3,4-Dichlorostyryl)-1,3-dihydro-2H-1,4-benzodiazepin-2-one

In an analogous manner to Example 107 but replacing 2'-(methylamino)acetophenone with 2'-aminoacetophenone there was obtained (E)-5-(3,4-dichlorostyryl)-1,3-dihydro-2H-1,4-benzodiazepin-2-one as an off white solid, MS: m/e 331.1 [M+H]+.

EXAMPLE 111

(E)-5-[2-(4-Chlorophenylthio)styryl]-2,3-dihydro-1H-1,4-benzodiazepine hydrochloride In an analogous manner to Example 107 but replacing 3,4-dichlorobenzaldehyde with 2-(4-chlorophenylthio) benzaldehyde there was obtained (E)-5-[2-(4-chlorophenylthio)styryl]-2,3-dihydro-1H-1,4-benzodiazepine hydrochloride as a red solid MS: m/e 391.2 [M+H]+.

EXAMPLE 112

(E)-5-(3,4-Dichlorostyryl)-2,3-dihydro-1H-benzo-1,4-diazepine dihydrochloride 1.3 g (4.41 mmol) of (E)-3-(3,4-dichlorophenyl)-1-(2-fluorophenyl)propenone were refluxed in a mixture of 5 ml of ethylenediamine and 10 ml of pyridine for 17 hours. The solvent was removed by evaporation and the residue chromatographed on silica gel using dichloromethane/methanol (92:8) for the elution. The product was added to a mixture of ethyl acetate and 2M hydrochloric acid and the solid filtered off and recrystallized from ethanol/acetone to give 35 mg of (E)-5-(3,4-dichlorostyryl)-2,3-dihydro-1H-benzo-1,4-diazepine dihydrochloride as a red solid. MS: m/e 316.9 [M+H]$^+$.

The starting material was prepared as follows:

0.2 ml of 3M sodium hydroxide solution were added to a solution of 1.38 g (10 mmol) of 2-fluoroacetophenone and 1.75 g (10 mmol) of 3,4-dichlorobenzaldehyde in 20 ml of ethanol. After 30 minutes the solid was filtered off and washed with ethanol and petrol to give 1.49 g of (E)-3-(3,4-dichlorophenyl)-1-(2-fluorophenyl)propenone as a white solid. 1H NMR (400 MHz CDCl$_3$) 7.08–7.58 (8H,m), 7.75–7.85 (1H,dt).

EXAMPLE 113

(E)-5-(3,4-Dichlorostyryl)-2,3-dihydro-1-methyl-1H-benzo-1,4-diazepine dihydrochloride In an analogous manner to Example 112 but replacing ethylenediamine with N-methylethylenediamine there was obtained (E)-5-(3,4-dichlorostyryl)-2,3-dihydro-1-methyl-1H-benzo-1,4-diazepine dihydrochloride as a red solid MS: m/e 331 [M+H]$^+$.

EXAMPLE 114

(E)-5-(3,4-Dichlorostyryl)-2,3-dihydro-8-(tetrahydro-2(RS)-pyranyloxy)-1-methyl-1H-1,4-benzodiazepine In an analogous manner to Example 112 but replacing 2-fluoroacetophenone with 2-fluoro-4-(RS)-pyranyloxyacetophenone and ethylenediamine with N-methylethylenediamine there was obtained (E)-5-(3,4-dichlorostyryl)-2,3-dihydro-8-(tetrahydro-2(RS)-pyranyloxy)-1-methyl-1H-1,4-benzodiazepine as a dark red solid MS: m/e 431.2 [M+H]$^+$.

EXAMPLE 115

(E)-5-[2-(4-Chlorophenylthio)styryl]-2,3-dihydro-8-(tetrahydro-2(RS)-pyranyloxy)-1-methyl-1H-1,4-benzodiazepine In an analogous manner to Example 112 but replacing 2-fluoroacetophenone with 2-fluoro-4-(RS)-pyranyloxyacetophenone and ethylenediamine with N-methylethylenediamine and 3,4-dichlorobenzaldehyde with 2-(4-chlorophenylthio)-benzaldehyde there was obtained (E)-5-[2-(4-chlorophenylthio)styryl]-2,3-dihydro-8-(tetrahydro-2(RS)-pyranyloxy)-1-methyl-1H-1,4-benzodiazepine as a yellow foam MS: m/e 505.2 [M+H]$^+$.

EXAMPLE 116 tert-Butyl (E)-[5-(3,4-dichlorostyryl)-2,3-dihydro-1-methyl-1H-1,4-benzodiazepin-7-yl]carbamate In an analogous manner to Example 112 but replacing 2-fluoroacetophenone with (3-Acetyl4-fluorophenyl)carbamic acid tert-butyl ester and ethylenediamine with N-methylethylenediamine there was obtained tert-butyl (E)-[5-(3,4-dichlorostyryl)-2,3-dihydro-1-methyl-1H-1,4-benzodiazepin-7-yl]carbamate as a light brown solid MS: m/e 446.2 [M+H]$^+$.

The (3-acetyl-4-fluorophenyl)carbamic acid tert-butyl ester starting material was prepared as follows.

To a solution of 1.19 g (7.77 mmol) of 1-(5-amino-2-fluorophenyl)ethanone in 18 ml of dry tetrahydrofuran at room temperature under an atmosphere of nitrogen was added 1.86 g (8.54 mol) of tert-butyl dicarbonate. The solution was stirred for 28 hours at room temperature followed by 17 hours at 45° C., cooled to room temperature and evaporated under reduced pressure. The residue was dissolved in ethyl acetate and the solution washed with sodium bicarbonate solution, dried over magnesium sulphate, evaporated to dryness and the residue chromatographed on silica gel using ethyl acetate/petrol 4:1 for the elution. There was obtained 1.45 g of (3-acetyl-4-fluorophenyl)carbamic acid tert-butyl ester MS: m/e 271 [M+CH$_3$CN]$^+$.

EXAMPLE 117

(E)-5-(3,4-Dichlorostyryl)-1-ethyl-2,3-dihydro-1H-1,4-benzodiazepine dihydrochloride In an analogous manner to Example 112 but replacing ethylenediamine with N-ethylethylenediamine there was obtained (E)-5-(3,4-dichlorostyryl)-1-ethyl-2,3-dihydro-1H-1,4-benzodiazepine dihydrochloride as a dark red solid. MS: m/e 344.9 [M+H]$^+$.

EXAMPLE 118

(E)-5-(3,4-Dichlorostyryl)-2,3-dihydro-1-propyl-1H-1,4-benzodiazepine dihydrochloride In an analogous manner to Example 112 but replacing ethylenediamine with N-propylethylenediamine there was obtained (E)-5-(3,4-dichlorostyryl)-2,3-dihydro-1-propyl-1H-1,4-benzodiazepine dihydrochloride as a dark red solid MS: m/e 359 [M+H]$^+$.

EXAMPLE 119

(E)-1-Benzyl-5-(3,4-dichlorostyrl)-2,3-dihydro-1H-1,4-benzodiazepine dihydrochloride In an analogous manner to Example 112 but replacing ethylenediamine with N-benzylethylenediamine there was obtained (E)-1-benzyl-5-(3,4-dichlorostyryl)-2,3-dihydro-1H-1,4-benzodiazepine dihydrochloride as a red solid. MS: m/e 406.9 [M+H]$^+$.

EXAMPLE 120

(E)-5-(3,4-Dichlorostyryl)-2,3-dihydro-1H-1,4-benzodiazepine-1-ethanol dihydrochloride In analogous manner to Example 112 but replacing ethylenediamine with 2-(2-aminoethylamino)ethanol there was obtained (E)-5-(3,4-dichlorostyryl)-2,3-dihydro-1H-1,4-benzodiazepine-1-ethanol dihydrochloride as a red solid MS: m/e 360.9 [M+H]$^+$.

EXAMPLE 121

(E)-5-[2-(4-Chlorophenylthio)styryl]-2,3-dihydro-1-methyl-1H-1,4-benzodiazepine dihydrochloride In an analogous manner to Example 112 but replacing ethylenediamine with N-methylethylenediamine and 3,4-dichlorobenzaldehyde with 2-(4-chlorophenylthio)-benzaldehyde there was obtained (E)-5-[2-(4- chlorophenylthio)styryl]-2,3-dihydro-1-methyl-1H-1,4-benzodiazepine dihydrochloride as a red solid. MS: m/e 405 [M+H]$^+$.

EXAMPLE 122

(E)-5-(3,4-Dichlorostyryl)-6-(trifluoromethyl)-2,3-dihydro-1-methyl-1H-1,4-benzodiazepine dihydrochloride In an analogous manner to Example 112 but replacing ethylenediamine with N-methylethylenediamine and 2-fluoroacetophenone with 2-fluoro-6-trifluoromethyl-acetophenone there was obtained (E)-5-(3,4-dichlorostyryl)-6-(trifluoromethyl)-2,3-dihydro-1-methyl-1H-1,4-benzodiazepine dihydrochloride as a light orange solid. MS: m/e 398.9 [M+H]$^+$.

EXAMPLE 123

(E)-5-(3,4-Dichlorostyryl)-2,3-dihydro-1-isopropyl-1H-1,4-benzodiazepine dihydrochloride A mixture of 1,475 g (5 mmol) of (E)-3-(3,4-dichlorophenyl)-1-(2-fluorophenyl)propenone and 1.1 g (5.45 mmol) of N-[2-(isopropylamino)ethyl]pivalamide was refluxed in 10 ml of pyridine for 6 hours. The solvent was removed by evaporation and the residue dissolved in water and ethyl acetate. The organic phase was dried over magnesium sulphate, evaporated to dryness, triturated with ethanol and filtered. After evaporation the filtrate was chromatographed on silica gel using ethyl acetate/petrol (1:4) for the elution then chromatographed again using dichloromethane/methanol (49:1) to give 26 mg of a yellow gum which was added to a solution of 50 mg (0.26 mmol) of 4-toluenesulphonic acid in 5 ml of acetonitrile and refluxed for 30 seconds. The solvent was removed by evaporation and the residue dissolved in 5 ml of methanol and 50 mg (0.5 mmol) of triethylamine added. After refluxing for 1 minute the solvent was removed and the residue dissolved in saturated sodium bicarbonate solution and ethyl acetate. The organic phase was dried over magnesium sulphate, filtered, evaporated to dryness and the residue chromatographed on silica gel using ethyl acetate for the elution. The product was dissolved in a solution of hydrogen chloride in ethyl acetate, evaporated to dryness, redissolved in a small volume of ethyl acetate and allowed to crystallize. There was obtained 7 mg of (E)-5-(3,4-dichlorostyryl)-2,3-dihydro-1-isopropyl-1H-1,4-benzodiazepine dihydrochloride as an orange solid. MS: m/e 359 [M+H]$^+$.

The starting material was prepared as follows:

6.54 g (30 mmol) of di-tert-butyl dicarbonate in 30 ml of tetrahydrofuran were added dropwise over 30 minutes to an ice-cooled, stirred solution of 5.1 g (50 mmol) of N-isopropylethylenediamine in 100 ml of tetrahydrofuran. The mixture was stirred at room temperature for 3 hours then evaporated to dryness. The residue was dissolved in diethyl ether and water and the organic phase dried over magnesium sulphate, evaporated to dryness and the residue chromatographed on silica gel using dichloromethane/methanol/ acetic acid/water (120:15:3:2) for the elution. There was obtained 3.6 g of N-[2-(isopropylamino)ethyl]pivalamide as a colorless oil. $^1$H NM (400 MHz, CDCl3) δ: 1.01 (6H,d), 1.41 (9H,s), 2.69 (2H,t), 2.75 (1H,m), 3.18 (2H,q), 4.92 (1H,br.s)

EXAMPLE 124

(E)-1-Acetyl-5-(3,4-dichlorostyryl)-2,3-dihydro-1H-1,4-benzodiazepine hydrochloride 50 mg (0.158 mmol) of (E)-5-(3,4-dichlorostyryl)-2,3-dihydro-1H-benzo-1,4-diazepine were dissolved in a mixture of 0.1 ml of acetic anhydride and 1 ml of pyridine by heating to 80° C. The mixture was left to cool for 30 minutes then evaporated to dryness and the residue dissolved in water and ethyl acetate. The organic phase was dried over magnesium sulphate, filtered, evaporated to dryness and the residue chromatographed on silica gel using ethyl acetate for the elution. The product was dissolved in a solution of hydrogen chloride in ethyl acetate, evaporated to dryness and the residue dissolved in a small volume of acetone and left to crystallize. There was obtained 12 mg of (E)-1-acetyl-5-(3,4-dichlorostyryl)-2,3-dihydro-1H-1,4-benzodiazepine hydrochloride as an off-white solid. MS: m/e 358.9 [M+H]$^+$.

EXAMPLE 125

(E)-1-Benzoyl-5-(3,4-dichlorostyryl)-2,3-dihydro-1H-1,4-benzodiazepine hydrochloride In an analogous manner to Example 124 but replacing acetic anhydride with benzoic anhydride there was obtained (E)-1-benzoyl-5-(3,4-dichlorostyryl)-2,3-dihydro-1H-1,4-benzodiazepine hydrochloride as an off-white solid. MS: m/e 420.9 [M+H]$^+$.

EXAMPLE 126

(E)-5-(3,4-Dichlorostyryl)-2,3-dihydro-1-(4-nitrobenzyl)-1H-1,4-benzodiazepine dihydrochloride A mixture of 117 mg (0.3 mmol) of (E)-5-(3,4-dichlorostyryl)-2,3-dihydro-1H-benzo-1,4-diazepine dihydrochloride, 70 mg (0.32 mmol) of 4-nitrobenzyl bromide and 127 mg (1.2 mmol) of sodium carbonate were heated at 70° C. in 3 ml of ethanol for 18 hours. The mixture was diluted with ethyl acetate and water and the organic phase dried over magnesium sulphate, filtered and evaporated to dryness. The residue was chromatographed three times on silica gel using ethyl acetate/petrol (3:1), dichloromethane/methanol (97:3) and ethyl acetate/petrol (9:1) for the elutions. The product was dissolved in a solution of hydrogen chloride in methanol, evaporated to dryness and the residue triturated with diethyl ether to give 12 mg of (E)-5-(3,4-dichlorostyryl)-2,3-dihydro-1-(4-nitrobenzyl)-1H-1,4-benzodiazepine dihydrochloride. MS: m/e 451.9 [M+H]$^+$.

EXAMPLE 127

Methyl (E)4-[[5-(3,4-dichlorostyryl)-2,3-dihydro-1H-1,4-benzodiazepin-1-yl]methyl]benzoate dihydrochloride In an analogous manner to Example 126 but replacing 4-nitrobenzyl bromide with methyl 4-(bromomethyl) benzoate there was obtained methyl (E)-4-[[5-(3,4-dichlorostyryl)-2,3-dihydro-1H-1,4-benzodiazepin-1-yl] methyl]benzoate dihydrochloride as a red solid. MS: m/e 465 [M+H]$^+$.

EXAMPLE 128

Methyl (E)-3-[[5-(3,4-dichlorostyryl)-2,3-dihydro-1H-1,4-benzodiazepin-1-yl]methyl]benzoate hydrochloride In an analogous manner to Example 126 but replacing 4-nitrobenzyl bromide with methyl 3-(bromomethyl) benzoate there was obtained methyl (E)-3-[[5-(3,4-dichlorostyryl)-2,3-dihydro-1H-1,4-benzodiazepin-1-yl] methyl]benzoate hydrochloride as a dark orange solid_MS: m/e 465.2 [M+H]$^+$.

EXAMPLE 129

Methyl (E)-2-[[5-(3,4-dichlorostyryl)-2,3-dihydro-1H-1,4-benzodiazepin-1-yl]methyl]benzoate hydrochloride In an analogous manner to Example 126 but replacing 4-nitrobenzyl bromide with methyl 2-(bromomethyl)benzoate there was obtained methyl (E)-2-[[5-(3,4-dichlorostyryl)-2,3-dihydro-1H-1,4-benzodiazepin-1-yl]methyl]benzoate hydrochloride as a dark orange solid_MS: m/e 465.2 [M+H]$^+$.

EXAMPLE 130

Methyl (E)-4-[[5-[2-(4-chlorophenylthio)styryl]-2,3-dihydro-1H-1,4-benzodiazepin-1-yl]methyl]benzoate hydrochloride In an analogous manner to Example 126 but replacing 4-nitrobenzyl bromide with methyl 4-(bromomethyl)benzoate and replacing 3,4-dichlorobenzaldehyde with 2-(4-chlorophenylthio)benzaldehyde there was obtained methyl (E)-4-[[5-[2-(4-chlorophenylthio)styryl]-2,3-dihydro-1H-1,4-benzodiazepin-1-yl]methyl]benzoate hydrochloride as a dark orange solid_MS: m/e 539.2 [M+H]$^+$.

EXAMPLE 131

(E)-5-(3,4-dichlorostyryl)-2,3-dihydro-1-[(2-naphthyl)methyl]-1H-1,4-benzodiazepine dihydrochloride In an analogous manner to Example 126 but replacing 4-nitrobenzyl bromide with 2-(bromomethyl)naphthalene there was obtained (E)-5-(3,4-dichlorostyryl)-2,3-dihydro-1-[(2-naphthyl)methyl]-1H-1,4-benzodiazepine dihydrochloride as a red solid. MS: m/e 457 [M+H]$^+$.

EXAMPLE 132

(E)-4-[[5-(3,4-dichlorostyryl)-2,3-dihydro-1H-1,4-benzodiazepin-1-yl]methyl]benzoic acid dihydrochloride 0.4 ml of 1M potassium hydroxide solution were added to a solution of 80 mg (0.17 mmol) of methyl (E)-4-[[5-(3,4-dichlorostyryl)-2,3-dihydro-1H-1,4-benzodiazepin-1-yl]methyl]benzoate in 8 ml of methanol. The mixture was heated at 60° C. for 4 hours then left at room temperature for 3 days. A further 0.2 ml of 1M potassium hydroxide solution were added followed by heating at 60° C. for 4 hours. The solvent was removed by evaporation and the residue dissolved in diethyl ether and water. The aqueous phase was separated, acidified with acetic acid and extracted three times with ethyl acetate. The combined organic extracts were dried over magnesium sulphate, filtered and evaporated to dryness. The residue was chromatographed on silica gel using dichloromethane/methanol/acetic acid/water (120:15:3:2) for the elution. The product was dissolved in a mixture of 10 ml of acetone and 0.2 ml of concentrated hydrochloric acid, evaporated to dryness and the residue triturated with diethyl ether. There was obtained 55 mg of (E)-4-[[5-(3,4-dichlorostyryl)-2,3-dihydro-1H-1,4-benzodiazepin-1-yl]methyl]benzoic acid dihydrochloride MS: m/e 451 [M+H]$^+$.

EXAMPLE 133

(E)-3-[[5-(3,4-Dichlorostyryl)-2,3-dihydro-1H-14-benzodiazepin-1-yl]methyl]benzoic]acid hydrochloride In an analogous manner to Example 132 but replacing methyl (E)-4-[[5-(3,4-dichlorostyryl)-2,3-dihydro-1H-1,4-benzodiazepin-1-yl]methyl]benzoate with methyl (E)-3-[[5-(3,4-dichlorostyryl)-2,3-dihydro-1H-1,4-benzodiazepin-1-yl]methyl]benzoate there was obtained (E)-3-[[5-(3,4-dichlorostyryl)-2,3-dihydro-1H-1,4-benzodiazepin-1-yl]methyl]benzoic acid hydrochloride as a dark red solid MS: m/e 451 [M+H]$^+$.

EXAMPLE 134

(E)-2-[[5-(3,4-Dichlorostyryl)-2,3-dihydro-1H-1,4-benzodiazepin-1-yl]methyl]benzoic]acid hydrochloride In an analogous manner to Example 132 but replacing methyl (E)-4-[[5-(3,4-dichlorostyryl)-2,3-dihydro-1H-1,4-benzodiazepin-1-yl]methyl]benzoate with methyl (E)-2-[[5-(3,4-dichlorostyryl)-2,3-dihydro-1H-1,4-benzodiazepin-1-yl]methyl]benzoate there was obtained (E)-2-[[5-(3,4-dichlorostyryl)-2,3-dihydro-1H-1,4-benzodiazepin-1-yl]methyl]benzoic acid hydrochloride as a red solid. MS: m/e 451.2 [M+H]$^+$.

EXAMPLE 135

(E)-4-[[5-[2-(4-Chlorophenylthio)styryl]-2,3-dihydro-1H-1,4-benzodiazepin-1-yl]methyl]benzoic acid hydrochloride In an analogous manner to Example 132 but replacing methyl (E)-4-[[5-(3,4-dichlorostyryl)-2,3-dihydro-1H-1,4-benzodiazepin-1-yl]methyl]benzoate with methyl (E)4-[[5-[2-(4-chlorophenylthio)styryl]-2,3-dihydro-1H-1,4-benzodiazepin-1-yl]methyl]benzoate hydrochloride there was obtained (E)4-[[5-[2-(4-chlorophenylthio)styryl]-2,3-dihydro-1H-1,4-benzodiazepin-1-yl]methyl]benzoic acid hydrochloridehydrochloride as a dark orange solid. MS: m/e 525.2 [M+H]$^+$.

EXAMPLE 136

(E)-5-(3,4-Dichlorostyryl)-N-ethyl-2,3-dihydro-1H-1,4-benzodiazepine-1-carboxamide A solution of 32 mg (0.1 mmol) of (E)-5-(3,4-dichlorostyryl)-2,3-dihydro-1H-benzo-1,4-diazepine and 10 mg (0.14 mmol) of ethyl isocyanate was heated at 85° C. for 48 hours, a further 10 mg of ethyl isocyanate being added after 6 hours and again after 30 hours. The solvent was removed by evaporation and the residue chromatographed on silica gel using dichloromethane/methanol (19:1) for the elution. The product was recrystallized from diethyl ether. There was obtained 16 mg of (E)-5-(3,4-dichlorostyryl)-N-ethyl-2,3-dihydro-1H-1,4-benzodiazepine-1-carboxamide as an off-white solid. MS: m/e 387.9 [M+H]$^+$.

EXAMPLE 137

(E)-5-(3,4-Dichlorostyryl)-2,3-dihydro-1H-1,4-benzodiazepine-1-acetic acid 0.5 ml of 1M sodium hydroxide solution were added to a solution of 113 mg (0.28 mmol) of ethyl (E)-2-[5-(3,4-dichlorostyryl)-2,3-dihydro-1,4-benzodiazepin-1-yl]acetate in 3 ml of ethanol and the mixture left at room temperature for 1.5 hours. The solvent was removed by evaporation and the residue dissolved in water and washed with diethyl ether. The aqueous layer was acidified with acetic acid and a red gum separated out. The gum was dissolved in a small amount of ethanol and diluted with ethyl acetate and washed with water. The organic phase was dried over magnesium sulphate, filtered and evaporated to dryness to give 88 mg of (E)-5-(3,4-dichlorostyryl)-2,3-dihydro-1H-1,4-benzodiazepine-1-acetic acid as a red solid. MS: m/e 374.9 $[M+H]^+$.

The starting material was prepared in an analogous manner to Example 126 but replacing 4-nitrobenzyl bromide with ethyl bromoacetate there was obtained ethyl (E)-2-[5-(3,4-dichlorostyryl)-2,3-dihydro-1,4-benzodiazepin-1-yl] acetate as an orange gum. MS: m/e 402.9 $[M+H]^+$.

EXAMPLE 138

(E)-5-(3,4-Dichlorostyryl)-2,3-dihydro-N-(2-methoxyethyl)-1H-1,4-benzodiazepine-1-acetamide dihydrochloride A mixture of 33 mg (0.088 mmol) of (E)-5-(3,4-dichlorostyryl)-2,3-dihydro-1H-1,4-benzodiazepine-1-acetic acid, 30 mg (0.157 mmol) of 1-[3-(dimethylamino)propyl]-3-ethylcarbodiimide hydrochloride, 16 mg (0.105 mmol) of 1-hydroxybenzotriazole hydrate and 14 mg (0.187 mmol) of 2-methoxyethylamine was stirred in 3 ml of dichloromethane for 3 hours. The solution was washed with saturated sodium bicarbonate solution, dried over magnesium sulphate, filtered and evaporated to dryness. The residue was chromatographed three times on silica gel using dichloromethane/methanol (94:6), dichloromethane/methanol 92:8) and ethyl acetate/methanol (9:1) for the elutions. The product was dissolved in a solution of hydrogen chloride in ethyl acetate, evaporated to dryness and the residue triturated with diethyl ether. There was obtained 5 mg of (E)-5-(3,4-dichlorostyryl)-2,3-dihydro-N-(2-methoxyethyl)-1H-1,4-benzodiazepin-1-acetamide dihydrochloride as a red solid. MS: m/e 431.9 $[M+H]^+$.

EXAMPLE 139

Ethyl (E)-6-(3,4-dichlorostyryl)-4H-imidazo[1,5-a] benzodiazepine-3-carboxylate 100 mg (2.5 mmol) of 60% sodium hydride disperion in mineral oil were added to a solution of 728 mg (2.2 mmol) of (E)-5-(3,4-dichlorostyryl)-1,3-dihydro-2H-1,4-benzodiazepin-2-one in 5 ml of anhydrous dimethylformamide at room temperature under a nitrogen atmosphere and stirred for 30 minutes. The mixture was cooled to −20° C., 431 mg (2.5 mmol) of diethyl chlorophosphate were added and stirring was continued for a further 30 minutes at −10° C. before being added to a solution prepared by addition of 1.65 ml (3.3 mmol) of 2M lithium diisopropylamide to a solution of 375 mg (3.32 mmol) of ethyl isocyanoacetate in 5 ml of anhydrous tetrahydrofuran at −78° C. under a nitrogen atmosphere. The resulting mixture was stirred at −78° C. for 2 hours then warmed to −30° C. and 180 mg (3 mmol) of acetic acid were added followed by water and ethyl acetate. The organic phase was washed twice with water, dried over magnesium sulphate, filtered and evaporated to dryness. The residue was chromatographed on silica gel using ethyl acetate/methanol (49:1) for the elution. The product was dissolved in 1 ml of ethyl acetate and 10 ml of diethyl ether and left to crystallize. There was obtained 116 mg of ethyl (E)-6-(3,4-dichlorostyryl)-4H-imidazo[1,5-a][1,4]benzodiazepine-3-carboxylate as a light-brown solid. MS: m/e 425.9 $[M+H]^+$.

EXAMPLE 140

(E)-4-[2-(2,3-Dihydro-1-methyl-1H-1,4-benzodiazepin-5-yl)vinyl]benzoic acid acetate 2.2 ml of 2M potassium hydroxide solution were added to a solution of 770 mg (2.41 mmol) of methyl (E)-4-[2-(2,3-dihydro-1-methyl-1H-1,4-benzodiazepin-5-yl)vinyl] benzoate in 22 ml of methanol. The temperature was raised to 60° C. and the solution was stirred for 3 hours. A further 2 ml of 2M potassium hydroxide solution was added and the solution was stirred for a further 16 hours. The solvent was removed by evaporation and the residue dissolved in water and washed with diethyl ether. The aqueous layer was acidified with acetic acid and extracted three times with ethyl acetate. The organic phases were combined, dried over magnesium sulphate, filtered and evaporated to dryness. There was obtained (E)-4-[2-(2,3-dihydro-1-methyl-1H-1,4-benzodiazepin-5-yl)vinyl]benzoic acid acetate as a red oil, MS: m/e 307.2 $[M+H]^+$.

The starting material was prepared by analogy to Example 1 replacing 3,4-difluorobenzaldehyde with methyl-4-formyl benzoate.

EXAMPLE 141

(E)-4-[2-(2,3-Dihydro-1-methyl-1H-1,4-benzodiazepin-5-yl)vinyl]-N-(4-methoxybenzyl) benzamide hydrochloride A mixture of 50 mg (0.164 mmol) of (E)-5-(3,4-dichlorostyryl)-2,3-dihydro-1H-1,4-benzodiazepine-1-acetic acid, 38 mg (0.199 mmol) of 1-[3-(dimethylamino)propyl]-3-ethylcarbodiimide hydrochloride, 27 mg (0.199 mmol) of 1-hydroxybenzotriazole hydrate and 0.021 ml (0.145 mmol) of 4-methoxybenzylamine was stirred in 5 ml of dichloromethane for 3 hours at room temperature and then left to stand at 4° C. for 54 hours. The solution was diluted with dichloromethane and then sequentially washed with citric acid, saturated sodium bicarbonate solution and brine, dried over magnesium sulphate, filtered and evaporated to dryness. The residue was chromatographed twice on silica gel using sequentially dichloromethane/methanol (98:2), dichloromethane/methanol (97:3) and dichloromethane/methanol (95:5) for the elutions. The product was dissolved in a solution of hydrogen chloride in ether and evaporated to dryness. There was obtained 9 mg of (E)-4-[2-(2,3-dihydro-1-methyl-1H-1,4-benzodiazepin-5-yl)vinyl]-N-(4-methoxybenzyl)benzamide hydrochloride as a red oil MS: m/e 426.3 $[M+H]^+$.

EXAMPLE 142

(E)-4-[2-(2,3-Dihydro-1-methyl-1H-1,4-benzodiazepin-5-yl)vinyl]-N-(3-methoxybenzyl) benzamide hydrochloride In an analogous manner to Example 141 but replacing 4-methoxybenzylamine with 3-methoxybenzylamine there was obtained (E)-4-[2-(2,3-dihydro-1-methyl-1H-1,4-benzodiazepin-5-yl)vinyl]-N-(3-methoxybenzyl)benzamide hydrochloride as a red oil MS: m/e 426.1 $[M+H]^+$.

EXAMPLE 143

(E)-4-[2-(2,3-Dihydro-1-methyl-1H-1,4-benzodiazepin-5-yl)vinyl]-N-(2-methoxybenzyl) benzamide hydrochloride In an analogous manner to Example 141 but replacing 4-methoxybenzylamine with 2-methoxybenzylamine there was obtained (E)4-[2-(2,3-dihydro-1-methyl-1H-1,4-benzodiazepin-5-yl)vinyl]-N-(2-methoxybenzyl)benzamide hydrochloride as a red oil MS: m/e 426.0 $[M+H]^+$.

EXAMPLE 144 tert-Butyl (E)-[2-[4-[2-(2,3-dihydro-1-methyl-1H-1,4-benzodiazepin-5-yl)-vinyl]-benzamido]ethyl)] carbamate In an analogous manner to Example 1 but replacing 3,4-difluorobenzaldehyde with [2-(4-formylbenzoylamino)-ethyl]carbamic acid tert-butyl ester there was obtained tert-butyl (E)-[2-[4-[2-(2,3-dihydro-1-methyl-1H-1,4-benzodiazepin-5-yl)-vinyl]-benzamido]ethyl)]carbamate as a light yellow glass MS: m/e 449.1 [M+H]⁺.

The starting material was prepared as follows

A mixture of 100 mg (0.67 mmol) of 4-carboxybenzaldehyde, 153 mg (0.798 mmol) of 1-[3-(dimethylamino)propyl]-3-ethylcarbodiimide hydrochloride and 106 mg (0.67 mmol) of N-(2-aminoethyl)carbamic acid tert-butyl ester was stirred in 5 ml of dichloromethane for 16 hours at room temperature. The solution was diluted with dichloromethane and then sequentially washed with citric acid, saturated sodium bicarbonate solution and brine, dried over magnesium sulphate, filtered and evaporated to dryness. There was obtained 184 mg of[2-(4-formylbenzoylamino)ethyl]carbamic acid tert-butyl ester as a colorless oil MS: m/e 316 [M+Na]⁺.

In a manner analogous to that described in Example 144, starting with 4-carboxybenzaldehyde, and the appropriate amine, the compounds shown in Table 12 were also prepared:

TABLE 12

| Compound | Structure | Name | MS (ES) (M + H)+ |
|---|---|---|---|
| Example 145 | 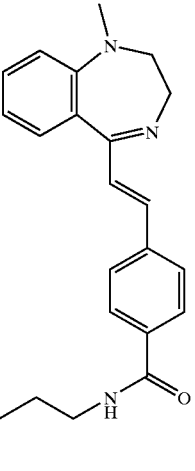 | tert-Butyl (E)-[3-[4-[2-(2,3-dihydro-1-methyl-1H-1,4-benzodiazepin-5-yl)vinyl]benzamido]-propyl]carbamate | 463.4 |
| Example 146 | 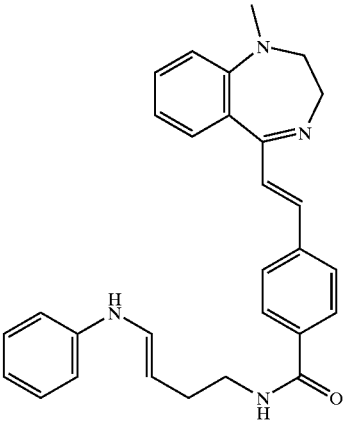 | (E)-4-[2-(2,3-Dihydro-1-methyl-1H-1,4-benzodiazepin-5-yl)vinyl]-N-[2-(1H-indol-3-yl)ethyl]benzamide | 449.1 |

TABLE 12-continued

| Compound | Name | MS (ES) (M + H)+ |
|---|---|---|
| Example 147 | (E)-N-[4-(Trifluoromethyl)benzyl]-4-[2-(2,3-dihydro-1-methyl-1H-1,4-benzodiazepin-5-yl)vinyl]benzamide | 464.3 |
| Example 148 | (E)-4-[2-(2,3-Dihydro-1-methyl-1H-1,4-benzodiazepin-5-yl)vinyl]-N-(2-methoxyethyl)benzamide | 364.0 |
| Example 149 | tert-Butyl (E)-(4-[4-[2-(2,3-dihydro-1-methyl-1H-1,4 benzodiazepin-5-yl)vinyl]benzamido]-butyl)carbamate | 477.1 |

TABLE 12-continued
| Compound | Structure | Name | MS (ES) (M + H)+ |
|---|---|---|---|
| Example 150 | 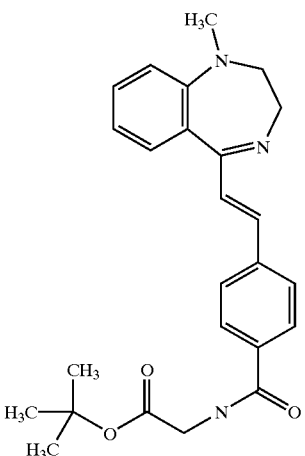 | tert-Butyl (E)-[4-[2-(2,3-dihydro-1-methyl-1H-1,4-benzodiazepin-5-yl)vinyl]benzamido]-acetate | 306.1 (M + H-Boc) |
| Example 151 | 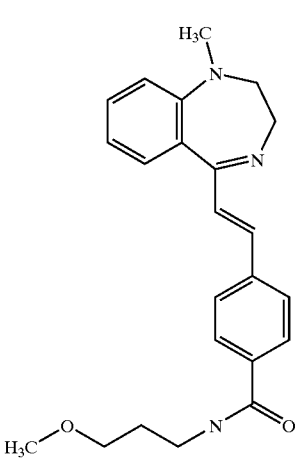 | (E)-4-[2-(2,3-Dihydro-1-methyl-1H-1,4-benzodiazepin-5-yl)vinyl]-N-(3-methoxypropyl)benz-amide | 378.3 |
| Example 152 | 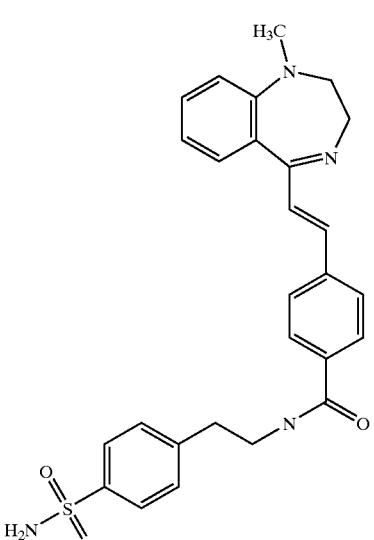 | (E)-4-[2-(2,3-Dihydro-1-methyl-1H-1,4-benzodiazepin-5-yl)vinyl]-N-[2-(4-sulfamoylphenyl)ethyl]-benzamide | 489.1 |

EXAMPLE 153

N-(2-Aminoethyl)-4-[2-(2,3-dihydro-1-methyl-1H-1,
4-benzodiazepin-5-yl)vinyl]benzamide
hydrochloride A few drops of a saturated solution of hydrogen chloride in diethyl ether were added to a solution of 15 mg (0.033 mmol) (tert-butyl (E)-[2-[4-[2-(2,3-dihydro-1-methyl-1H-1, 4-benzodiazepin-5-yl)-vinyl]-benzamido]ethyl)]carbamate. The mixture was stirred at room temperature for 16 hours and the resultant solid filtered off, dissolved in methanol and evaporated. There was obtained 8 mg of N-(2-aminoethyl)-4-[2-(2,3-dihydro-1-methyl-1H-1,4-benzodiazepin-5-yl) vinyl]benzamide hydrochloride as a dark red gum MS: m/e 349.0 [M+H]$^+$.

EXAMPLE 154

(E)-N-(3-Aminopropyl)-4-[2-(2,3-dihydro-1-methyl-
1H-1,4-benzodiazepin-5-yl)vinyl]benzamide
hydrochloride In an analogous manner to Example 153, starting with tert-butyl (E)-[3-[4-[2-(2,3-dihydro-1-methyl-1H-1,4-benzodiazepin-5-yl)vinyl]benzamido]propyl]carbamate, there was obtained (E)-N-(3-aminopropyl)-4-[2-(2,3-dihydro-1-methyl-1H-1,4-benzodiazepin-5-yl)vinyl] benzamide hydrochloride as a dark red glass MS: m/e 363.3 [M+H]$^+$.

EXAMPLE 155

(E)-N-(4-Aminobutyl)-4-[2-(2,3-dihydro-1-methyl-
1H-1,4-benzodiazepin-5-yl)vinyl]benzamide
hydrochloride In an analogous manner to Example 153, starting with tert-butyl (E)-(4-[4-[2-(2,3-dihydro-1-methyl-1H-1,4-benzodiazepin-5-yl)vinyl]benzamido]butyl)carbamate, there was obtained (E)-N-(4-Aaminobutyl)-4-[2-(2,3-dihydro-1-methyl-1H-1,4-benzodiazepin-5-yl)vinyl] benzamide hydrochloride as a red glass MS: m/e 377.3 [M+H]$^+$.

EXAMPLE 156

4-[2-(2,3-Dihydro-1-methyl-1H-1,4-benzodiazepin-
5-yl)vinyl]benzamide hydrochloride In an analogous manner to Example 153, starting with tert-butyl (E)-[4-[2-(2,3-dihydro-1-methyl-1H-1,4-benzodiazepin-5-yl)vinyl]benzamido]acetate, there was obtained 4-[2-(2,3-dihydro-1-methyl-1H-1,4-benzodiazepin-5-yl)vinyl]benzamide hydrochloride as a dark red glass MS: m/e 306.2 [M+H]$^+$.

EXAMPLE 157

(E)-5-(3,4-Dichlorostyryl)-2,3-dihydro-1-methyl-
1H-1,4-benzodiazepin-8-ol hydrochloride To a solution of 74 mg (0.17 mmol) of (E)-5-(3,4-dichlorostyryl)-2,3-dihydro-8-(tetrahydro-2(RS)-pyranyloxy)-1-methyl-1H-1,4-benzodiazepine (prepared in EXAMPLE 114) in methanol (5 ml) was added 33 mg (0.17 mmol) p-toluenesulphonic acid and the solution stirred at room temperature for 1 hour. A further 33 mg (0.17 mmol) of p-toluenesulphonic acid was added and the solution stirred for a further 2 hours. The solvent was removed by evaporation and the residue partitioned between water and ethyl acetate. The ethyl acetate layer was washed with saturated aqueous sodium hydrogen carbonate, dried over magnesium sulphate, filtered and evaporated to dryness. The residue was chromatographed on silica gel using first dichloromethane/methanol (95:5), and then dichloromethane/methanol (9:1) for the elution. The product was dissolved in a solution of hydrogen chloride in ether and evaporated to dryness. After trituration there was obtained 8 mg of (E)-5-(3,4-dichlorostyryl)-2,3-dihydro-1-methyl-1H-1,4-benzodiazepin-8-ol hydrochloride as a dark orange solid MS: m/e 347.2 [M+H]$^+$.

EXAMPLE 158

(E)-5-(3,4-Dichlorostyryl)-2,3-dihydro-1-methyl-8-
(2-thenyloxy)-1H-1,4-benzodiazepine To a stirred solution of 50 mg (0.14 mmol) of (E)-5-(3, 4-dichlorostyryl)-2,3-dihydro-1-methyl-1H-1,4-benzodiazepin-8-ol (prepared as described in Example 157) in 5 ml of dry tetrahydrofuran was added 0.014 ml (0.14 mmol) of thiophene-2-methanol and 0.053 ml (0.21 mmol) of tributylphosphine. The solution was cooled, under an atmosphere of nitrogen, to 0° C. and 37 mg (0.21 mmol) of 1,1'-azobis(N,N-dimethylformamide) was added. The mixture was allowed to warm up to room temperature and then stirred for 16 hours. A further 0.053 ml (0.21 mmol) of tributylphosphine and 37 mg (0.21 mmol) of 1,1'-azobis(N, N-dimethylformamide) were added and the mixture stirred for a further 4 hours. The mixture was filtered and the filtrate evaporated and then chromatographed on silica gel using dichloromethane/methanol (98:2) for the elution. There was obtained 4.2 mg of (E)-5-(3,4-dichlorostyryl)-2,3-dihydro-1-methyl-8-(2-thenyloxy)-1H-1,4-benzodiazepine as an orange gum MS: m/e 442.8 [M+H]$^+$.

EXAMPLE 159

Methyl (E)-4-[[5-(3,4-dichlorostyryl)-2,3-dihydro-1-
methyl-1H-1,4-benzodiazepin-8-yloxy]methyl]
benzoate diacetate In an analogous fashion to Example 158, replacing thiophene-2-methanol by 4-hydroxymethylbenzoic acid, there was obtained 30 mg of methyl (E)-4-[[5-(3,4-dichlorostyryl)-2,3-dihydro-1-methyl-1H-1,4-benzodiazepin-8-yloxy]methyl]benzoate diacetate as a dark red gum MS: m/e 495.2 [M+H]$^+$.

EXAMPLE 160

(E)-5-(3,4-Dichlorostyryl)-2,3-dihydro-1-methyl-
1H-1,4-benzodiazepin-7-amine hydrochloride To a solution of 11 mg (0.025 mmol) of tert-butyl (E)-[5-(3,4-dichlorostyryl)-2,3-dihydro-1-methyl-1H-1,4-benzodiazepin-7-yl]carbamate in 0.5 ml of acetonitrile and 1 drop of anisole was added 1 drop of trifluoroacetic acid. The solution was stirred for 20 minutes, concentrated under reduced pressure and the residue partitioned between brine and dichloromethane. The organic phase was dried over magnesium sulphate, filtered and evaporated, redissolved in a solution of hydrogen chloride in ethyl acetate and the solvent removed to afford 7.9 mg of (E)-5-(3,4-dichlorostyryl)-2,3-dihydro-1-methyl-1H-1,4-benzodiazepin-7-amine hydrochloride as a red solid MS: m/e 346.2 [M+H]$^+$.

EXAMPLE 161

(E)-5-(3,4-Dichlorostyryl)-2,3-dihydro-1-methyl-
1H-1,4-benzodiazepin-7-acetamide hydrochloride To a solution of 43 mg, 0.125 mmol) of (E)-5-(3,4-dichlorostyryl)-2,3-dihydro-1-methyl-1H-1,4- benzodiazepin-7-amine hydrochloride in 3 ml of dichloromethane was added 0.05 ml, 0.626 mmol) of pyridine, and 0.02 ml of acetic anhydride (0.15 mmol). The solution was stirred for 4 hours, concentrated under reduced pressure and the residue partitioned between brine and dichloromethane. The organic phase was dried over magnesium sulphate, filtered and evaporated, The residue was chromatographed on silica gel using first dichloromethane/methanol (98:2) and then dichloromethane/methanol (97:3) for the elution. The product was redissolved in a solution of hydrogen chloride in ethyl acetate and the solvent removed to afford (E)-5-(3,4-dichlorostyryl)-2,3-dihydro-1-methyl-1H-1,4-benzodiazepin-7-acetamide hydrochloride as a dark red solid MS: m/e 388.2 [M+H]$^+$.

EXAMPLE 162

(E)-N-[5-(3,4-Dichlorostyryl)-2,3-dihydro-1-methyl-1H-1,4-benzodiazepin-7-yl]methanesulfonamide To a solution of 100 mg, 0.219 mmol) of (E)-5-(3,4-dichlorostyryl)-2,3-dihydro-1-methyl-1H-1,4-benzodiazepin-7-amine hydrochloride in 3 ml of dichloromethane was added 0.073 ml, 0.9 mmol) of pyridine, and 0.018 ml, (0.231 mmol) of methanesulphonyl chloride. The solution was stirred for 1 hour, concentrated under reduced pressure and the residue partitioned between brine and dichloromethane. The organic phase was dried over magnesium sulphate, filtered and evaporated, The residue was chromatographed on silica gel using first dichloromethane/methanol (98:2) and then dichloromethane/methanol (97:3) for the elution. There was obtained (E)-5-(3,4-dichlorostyryl)-2,3-dihydro-1-methyl-1H-1,4-benzodiazepin-7-acetamide hydrochloride as a brown solid MS: m/e 424.1 [M+H]$^+$.

EXAMPLE 163

(E)-5-(3,4-Dichlorostyryl)-2,3-dihydro-8-(4-methoxyphenyl)-1-methyl-1H-1,4-benzodiazepine In an analogous fashion to Example 101, by replacing thiophene-3-boronic acid by 4-methoxyphenylboronic acid, there was obtained (E)-5-(3,4-dichlorostyryl)-2,3-dihydro-8-(4-methoxyphenyl)-1-methyl-1H-1,4-benzodiazepine as a red solid MS: m/e 473.2 [M+H]$^+$.

EXAMPLE 164

(E)-5-(3,4-Dichlorostyryl)-2,3-dihydro-1-methyl-8-(2-thienyl)-1H-1,4-benzodiazepine hydrochloride In an analogous fashion to Example 101, by replacing thiophene-3-boronic acid with thiophene-2-boronic acid, there was obtained (E)-5-(3,4-dichlorostyryl)-2,3-dihydro-1-methyl-8-(2-thienyl)-1H-1,4-benzodiazepine hydrochloride as a red solid MS: m/e 413.1 [M+H]$^+$.

EXAMPLE 165

(E)-5-(3,4-Dichlorostyryl)-2,3-dihydro-1-methyl-1H-1,4-benzodiazepin-8-amine hydrochloride In an analogous fashion to Example 83, from (E)-5-(3,4-dichlorostyryl)-2,3-dihydro-1-methyl-8-nitro-1H-1,4-benzodiazepine hydrochloride, there was obtained (E)-5-(3,4-dichlorostyryl)-2,3-dihydro-1-methyl-1H-1,4-benzodiazepin-8-amine hydrochloride as a red solid MS: m/e 346.2 [M+H]$^+$.

EXAMPLE 166

Methyl (E)-4-[[5-[2-[4-(3-bromophenyl)-3-pyridyl]vinyl]-8-chloro-2,3-dihydro-1,4-benzodiazepin-1-yl]methyl]benzoate In an analogous fashion to Example 126, using methyl 4-(bromomethyl)benzoate, and 4-(3-bromophenyl)-2-formyl-pyridine there was obtained methyl (E)-4-[[5-[2-[4-(3-bromophenyl)-3-pyridyl]vinyl]-8-chloro-2,3-dihydro-1,4-benzodiazepin-1-yl]methyl]benzoate as a light yellow solid, MS: m/e 588.1 [M+H]$^+$.

EXAMPLE 167

Methyl (E)-4-[[5-(2-benzylthio-5-nitrostyral)-8-chloro-2,3-dihydro-1,4-benzodiazepin-1-yl]methyl] benzoate In an analogous fashion to Example 126, using methyl 4-(bromomethyl)benzoate, and 2-benzylthio-5-nitrobenzaldehyde there was obtained methyl (E)-4-[[5-(2-benzylthio-5-nitrostyryl)-8-chloro-2,3-dihydro-1,4-benzodiazepin-1-yl]methyl]benzoate as a light yellow solid, MS: m/e 598.2 [M+H]$^+$.

EXAMPLE 168

(E)4-[[5-[2-[4-(3-Bromophenyl)-3-pyridyl]vinyl]-8-chloro-2,3-dihydro-1,4-benzodiazepin-1-yl]methyl] benzoic acid hydrochloride In an analogous fashion to Example 132, from methyl (E)-4-[[5-[2-[4-(3-bromophenyl)-3-pyridyl]vinyl]-8-chloro-2,3-dihydro-1,4-benzodiazepin-1-yl]methyl]benzoate, there was obtained (E)-4-[[5-[2-[4-(3-bromophenyl)-3-pyridyl]vinyl]-8-chloro-2,3-dihydro-1,4-benzodiazepin-1-yl]methyl]benzoic acid hydrochloride as a red solid, MS: m/e 574.2 [M+H]$^+$.

EXAMPLE 169

(E)-9-(3,4-Dichlorostyryl)-5,7-dihydro-6H-1,3-dioxolo[4,5-h][1,4]benzodiazepin-6-one In an analogous fashion to Example 112, by replacing 2-fluoroacetophenone with 1-(6-fluoro-benzo[1,3]dioxol-5-yl)-ethanone there was obtained (E)-9-(3,4-dichlorostyryl)-5,7-dihydro-6H-1,3-dioxolo[4,5-h][1,4]benzodiazepin-6-one as a red solid, MS: m/e 374.9 [M+H]$^+$.

EXAMPLE 170

(E)-9-(3,4-Dichlorostyryl)-5,7-dihydro-6H-1,3-dioxolo[4,5-h][1,4]benzodiazepin-6-one In an analogous fashion to Example 112, by replacing 2-fluoroacetophenone with 1-(2-fluoro-4,5-dimethoxyphenyl)ethanone there was obtained (E)-9-(3,4-dichlorostyryl)-5,7-dihydro-6H-1,3-dioxolo[4,5-h][1,4] benzodiazepin-6-one as a red solid, MS: m/e 390.9 [M+H]$^+$.

EXAMPLE 171

(E)-2,3-Dihydro-5-(4-methoxystyryl)-1-methyl-1H-1,4-benzodiazepine hydrochloride In an analogous fashion to Example 1, replacing 3,4-difluorobenzaldehyde with 4-methoxybenzaldehyde, there was obtained (E)-2,3-dihydro-5-(4-methoxystyryl)-1-methyl-1H-1,4-benzodiazepine hydrochloride as a dark red solid, MS: m/e 293.2 [M+H]$^+$.

EXAMPLE 172

(E)-2,3-Dihydro-1-methyl-5-(4-phenoxystyryl)-1H-1,4-benzodiazepine hydrochloride In an analogous fashion to Example 1, replacing 3,4-difluorobenzaldehyde with 4-phenoxybenzaldehyde, there was obtained (E)-2,3-dihydro-5-(4-methoxystyryl)-1-methyl-1H-1,4-benzodiazepine hydrochloride as a red oil, MS: m/e 355.3 [M+H]+.

EXAMPLE 173

(E)-2,3-Dihydro-1-methyl-5-styryl-1H-1,4-benzodiazepine dihydrochloride

In an analogous manner to example 107 but replacing 3,4-dichlorobenzaldehyde with benzaldehyde there was obtained (E)-2,3-dihydro-1-methyl-5-styryl-1H-1,4-benzodiazepine dihydrochloride as a red solid ms: m/e 263.0 [M+H]+.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A compound of the formula

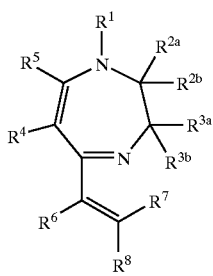

I wherein $R^1$ is H, lower alkyl, lower alkenyl, lower alkynyl, aryl lower alkyl, lower alkyl carbonyl, aryl carbonyl, lower alkyl amino carbonyl, aryl amino carbonyl, lower alkoxy carbonyl, aryloxy carbonyl, $R^{2a}$, $R^{2b}$ independently are H or lower alkyl or $R^{2a}$ and $R^{2b}$ together are oxo, $R^{3a}$, $R^{3b}$ independently are H or lower alkyl, $R^4$ and $R^5$ together with the two carbon atoms to which they are attached form an aryl, $R^6$ and $R^7$ is H or lower alkyl, and $R^8$ is aryl or a substituted or unsubstituted heterocycle selected from the group consisting of oxazolyl, isoxazolyl, furyl, tetrahydrofuryl, 1,3-dioxolanyl, dihydropyranyl, thienyl, pyrazinyl, isothiazolyl isoquinolinyl, indolyl, indazolyl, quinolinyl, dihydrooxazolyl, pyrimidinyl, benzofuranyl, tetrazolyl, pyrrolidinonyl, (N-oxide)-pyridinyl, pyrrol, triazolyl e.g. 1,2,4-triazolyl, pyrazolyl, benzotriazolyl, priperidinyl, morpholinyl, thiazolyl, pyridinyl, dihydrothiazolyl, imidazolidinyl, pyrazolinyl, benzothienyl, piperazinyl, imidazolyl, and thiadiazolyl, or pharmaceutically acceptable salts thereof.

2. The compounds of claim 1 wherein $R^{2a}$, $R^{2b}$, $R^{3a}$ and $R^{3b}$ are H.

3. The compounds of claim 1 or 2 having the formula

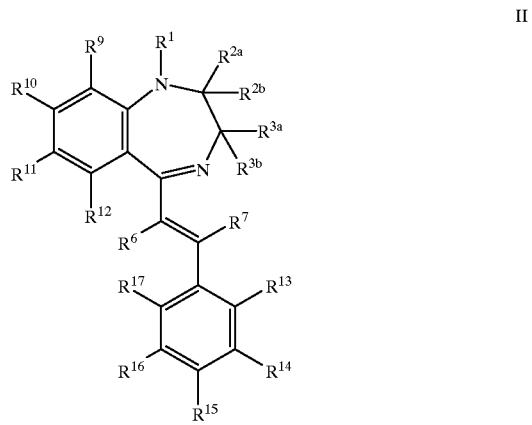

II wherein $R^9$, $R^{10}$, $R^{11}$, $R^{12}$, $R^{13}$, $R^{14}$, $R^{15}$, $R^{16}$ and $R^{17}$ independently are H, lower alkyl, lower alkenyl, lower alkynyl, cycloalkyl, aryl, heterocyclyl, carboxyl, cyano, alkoxy, cycloalkyl oxy, aryl oxy, heterocyclyl oxy, hydroxyl, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocylyl oxy carbonyl amino, alkyl amino carbonyl amino, dialkyl amino carbonyl amino, cycloalkyl amino carbonyl amino, aryl amino carbonyl amino, heterocyclyl amino carbonyl amino, alkyl carbonyl amino alkyl carbonyl amino, dialkyl amino carbonyl amino alkyl carbonyl amino, cycloalkyl carbonyl amino alkyl carbonyl amino, aryl carbonyl amino alkyl carbonyl amino and heterocyclyl carbonyl amino alkyl carbonyl amino, alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen or $R^{10}$ and $R^{11}$ together with the two carbon atoms to which they are attached form optionally substituted aryl or an optionally substituted heterocycle, or pharmaceutically acceptable salts thereof.

4. The compounds of claim 3 having the formula

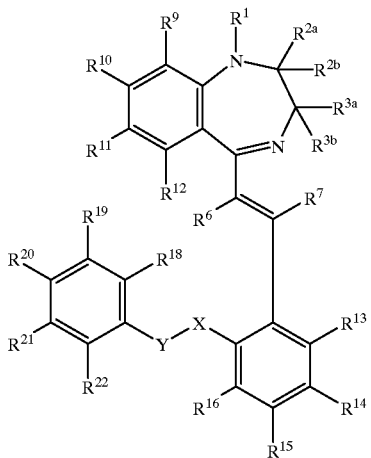

III wherein
- X is $(CH_2-)_n$ with n being an integer between 0 and 3, —S—, —O— or $NR^{23}$—, wherein $R^{23}$ is H or lower alkyl,
- Y is —$(CH_2—)_n$ with n being an integer between 0 and 3, and when X is $(CH_2—)_n$ with n being an integer between 0 and 3 then Y is S, O or —$NR^{23}$ wherein $R^{23}$ is as above,
- $R^{18}$, $R^{19}$, $R^{20}$ and $R^{22}$ independently are H, lower alkyl, lower alkenyl, lower alkynyl, cycloalkyl, aryl, heterocyclyl, carboxyl, cyano, alkoxy, cycloalkyl oxy, aryl oxy, heterocyclyl oxy, hydroxyl, alkyl carbonyl, cycloalkyl carbonyl, aryl carbonyl, heterocyclyl carbonyl, alkoxy carbonyl, cycloalkyl oxy carbonyl, aryl oxy carbonyl, heterocyclyl oxy carbonyl, amino carbonyl, alkyl amino carbonyl, dialkyl amino carbonyl, cycloalkyl amino carbonyl, aryl amino carbonyl, heterocyclyl amino carbonyl, amino, alkyl amino, dialkyl amino, alkenyl amino, alkynyl amino, cycloalkyl amino, aryl amino, heterocyclyl amino, alkyl carbonyl amino, dialkyl carbonyl amino, cycloalkyl carbonyl amino, aryl carbonyl amino, heterocyclyl carbonyl amino, alkoxy carbonyl amino, cycloalkyl oxy carbonyl amino, aryloxy carbonyl amino, heterocyclyl oxy carbonyl amino, alkyl amino carbonyl amino, dialkyl amino carbonyl amino, cycloalkyl amino carbonyl amino, aryl amino carbonyl amino, heterocyclyl amino carbonyl amino, alkyl carbonyl amino alkyl carbonyl amino, dialkyl amino carbonyl amino alkyl carbonyl amino, cycloalkyl carbonyl amino alkyl carbonyl amino, aryl carbonyl amino alkyl carbonyl amino and heterocyclyl carbonyl amino alkyl carbonyl amino, alkyl sulfonyl amino, cycloalkyl sulfonyl amino, aryl sulfonyl amino, heterocyclyl sulfonyl amino, nitro, alkyl sulfonyl, cycloalkyl sulfonyl, aryl sulfonyl, heterocyclyl sulfonyl, thio, alkyl thio, cycloalkyl thio, aryl thio, heterocyclyl thio or halogen or pharmaceutically acceptable salts thereof.

5. The compound according to claim 3, wherein $R^1$ is methyl and $R^6$ and $R^7$ are hydrogen.

6. A compound selected from the group consisting of:

| Structure | Name |
|---|---|
| 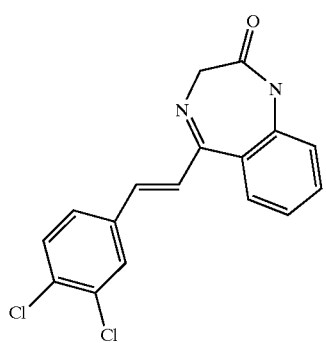 | (E)-5-(3,4-Dichlorostyryl)-1,3-dihydro-2H-benzo-1,4-diazepin-2-one |
| 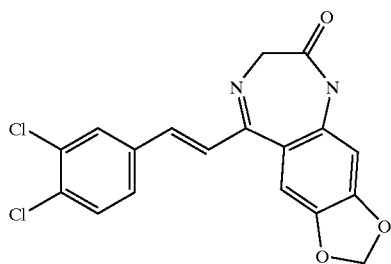 | (E)-9-(3,4-Dichlorostyryl)-5,7-dihydro-6H-1,3-dioxolo[4,5-h][1,4]benzodiazepin-6-one |

| Structure | Name |
|---|---|
| 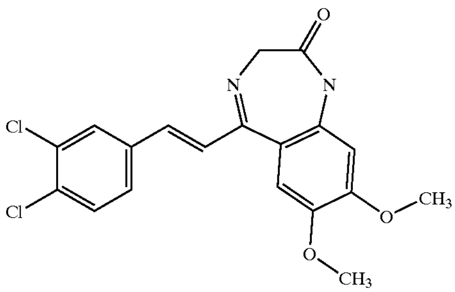 | (E)-5-(3,4-Dichlorostyryl)-1,3-dihydro-7,8-dimethoxy-2H-1,4-benzodiazepin-2-one |
| 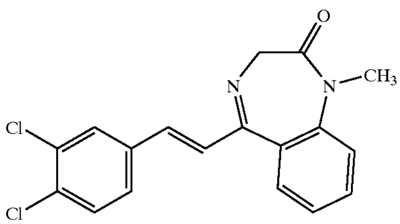 | (E)-5-(3,4-Dichlorostyryl)-1,3-dihydro-1-methyl-2H-benzo-1,4-diazepin-2-one |
| 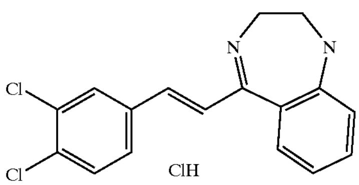 | (E)-5-(3,4-Dichlorostyryl)-2,3-dihydro-1H-benzo-1,4-diazepin dihydrochloride |
| 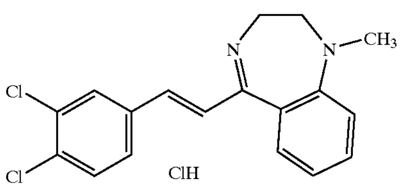 | (E)-5-(3,4-Dichlorostyryl)-2,3-dihydro-1-methyl-1H-benzo-1,4-diazepin dihydrochloride |
| 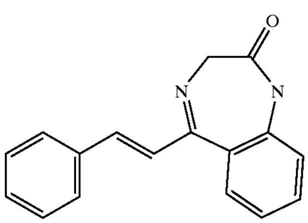 | (E)-1,3-Dihydro-5-styryl-2H-benzo-1,4-diazepin-2-one |
| 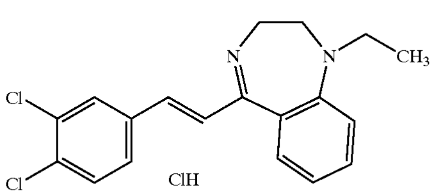 | (E)-5-(3,4-Dichlorostyryl)-1-ethyl-2,3-dihydro-1H-1,4-benzodiazepin dihydrochloride |
| 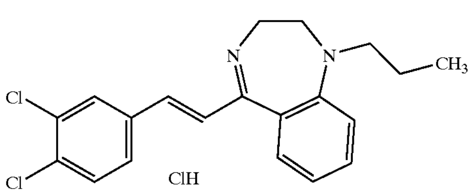 | (E)-5-(3,4-Dichlorostyryl)-2,3-dihydro-1-propyl-1H-1,4-benzodiazepin dihydrochloride |

-continued

| Structure | Name |
|---|---|
| 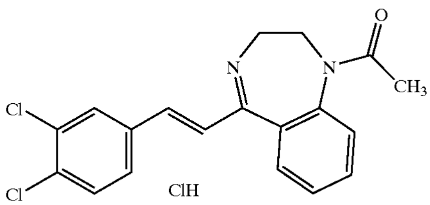 | (E)-1-Acetyl-5-(3,4-dichlorostyryl)-2,3-dihydro-1H-1,4-benzodiazepine hydrochloride |
| 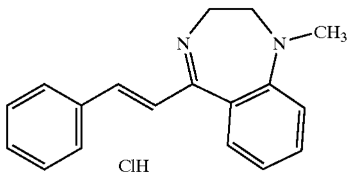 | (E)-2,3-Dihydro-1-methyl-5-styryl-1H-1,4-benzodiazepine dihydrochloride |
| 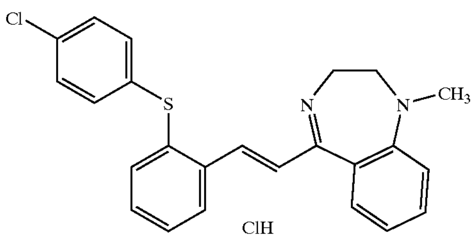 | (E)-5-[2-(4-Chlorophenylthio)styryl]-2,3-dihydro-1-methyl-1H-1,4-benzodiazepin dihydrochloride |
| 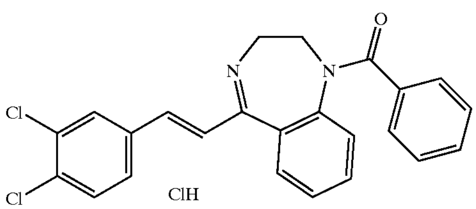 | (E)-1-Benzoyl-5-(3,4-dichlorostyryl)-2,3-dihydro-1H-1,4-benzodiazepin hydrochloride |
| 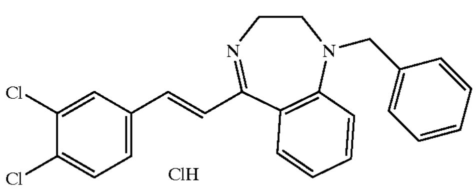 | (E)-1-Benzyl-5-(3,4-duchlorostyryl)-2,3-dihydro-1H-1,4-benzodiazepine dihydrochloride |
| 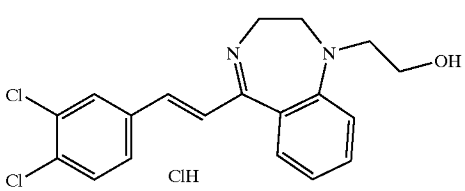 | (E)-5-(3,4-Dichlorostyryl)-2,3-dihydro-1H-1,4-benzodiazepin-1-ethanol hydrochloride |
| 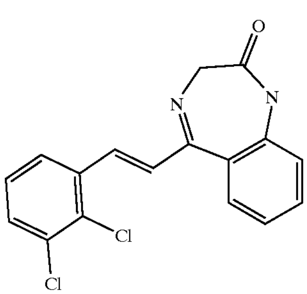 | (E)-5-(2,3-Dichlorostyryl)-1,3-dihydro-2H-1,4-benzodiazepin-2-one |

-continued

| Structure | Name |
|---|---|
| 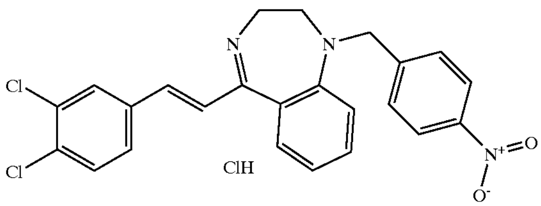 | (E)-5-(3,4-Dichlorostyryl)-2,3-dihydro-1-(4-nitrobenzyl)-1H-1,4-benzodiazepine dihydrochloride |
| 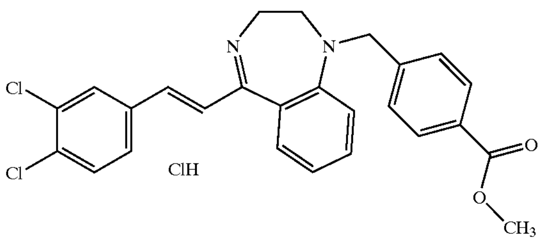 | Methyl (E)-4-[[5-(3,4-Dichlorostyryl)-2,3-dihydro-1H-1,4-benzodiazepin-1-yl]methyl]benzoate dihydrochloride |
| 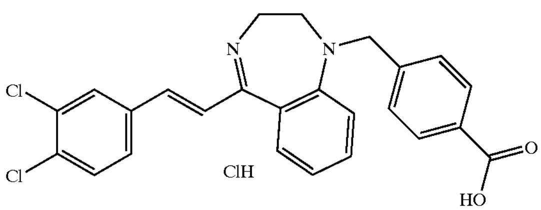 | (E)-4-[[5-(3,4-Dichlorostyryl)-2,3-dihydro-1H-1,4-benzodiazepin-1-yl]methyl]benzoic acid dihydrochloride |
| 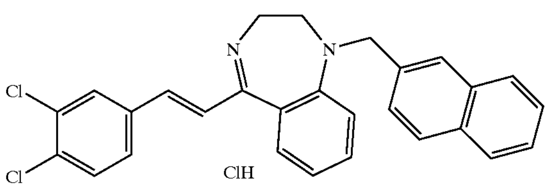 | (E)-5-(3,4-Dichlorostyryl)-2,3-dihydro-1-[(2-naphthyl)methyl]-1H-1,4-benzodiazepine dihydrochloride |
| 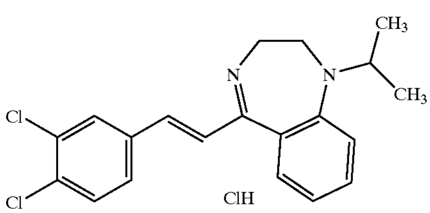 | (E)-5-(3,4-Dichlorostyryl)-2,3-dihydro-1-isopropyl-1H-1,4-benzodiazepine dihydrochloride |
| 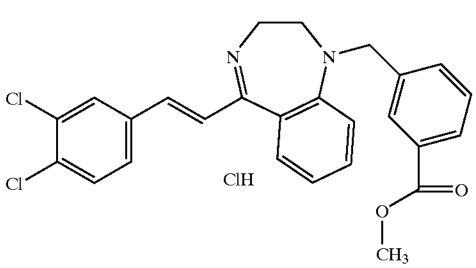 | Methyl (E)-3-[[5-(3,4-dichlorostyryl)-2,3-dihydro-1H-1,4-benzodiazepin-1-yl]methyl]benzoate hydrochloride |
| 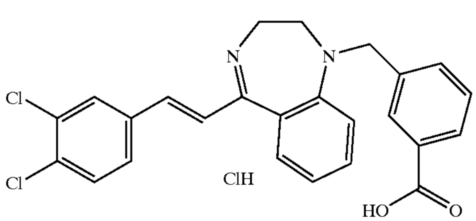 | (E)-3-[[5-(3,4-Dichlorostyryl)-2,3-dihydro-1H-1,4-benzodiazepin-1-yl]methyl]benzoic acid hydrochloride |

-continued

| Structure | Name |
|---|---|
| 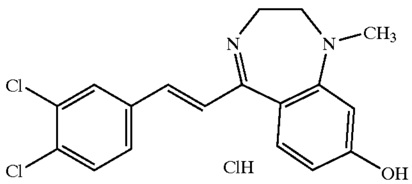 | (E)-5-(3,4-Dichlorostyryl)-2,3-dihydro-1-methyl-1H-1,4-benzodiazepin-8-ol hydrochloride |
| 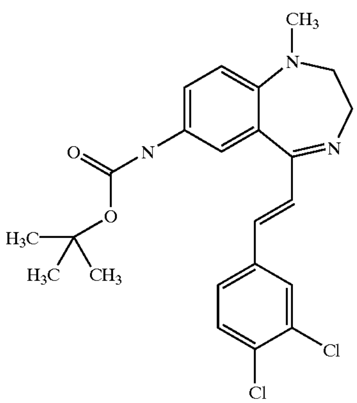 | tert-Butyl (E)-[5-(3,4-Dichlorostyryl)-2,3-dihydro-1-methyl-1H-1,4-benzodiazepin-7-yl]carbamate |
| 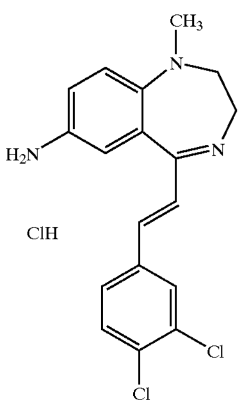 | (E)-5-(3,4-Dichlorostyryl)-2,3-dihydro-1-methyl-1H-1,4-benzodiazepin-7-amine hydrochloride |
| 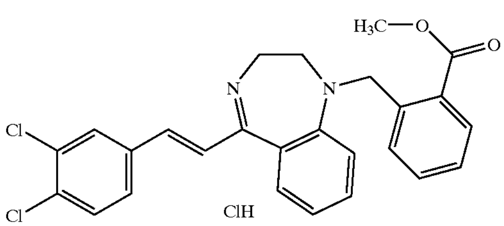 | Methyl (E)-2-[[5-(3,4-dichlorostyryl)-2,3-dihydro-1H-1,4-benzodiazepin-1-yl]methyl]benzoate hydrochloride |
| 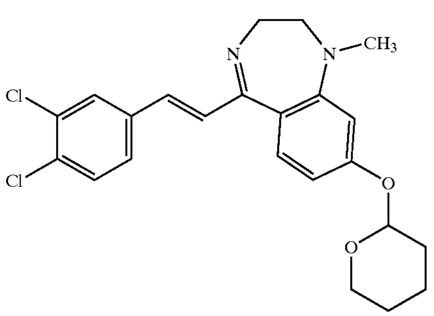 | (E)-5-(3,4-Dichlorostyryl)-2,3-dihydro-8-(tetrahydro-2(RS)-pyranyloxy)-1-methyl-1H-1,4-benzodiazepine |

-continued

| Structure | Name |
|---|---|
| 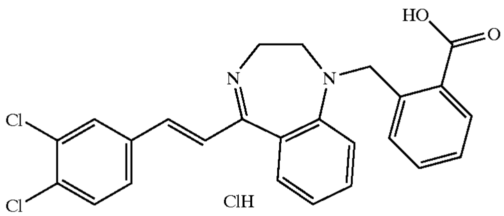 | (E)-2-[[5-(3,4-Dichlorostyryl)-2,3-dihydro-1H-1,4-benzodiazepin-1-yl]methyl]benzoic acid hydrochloride |
| 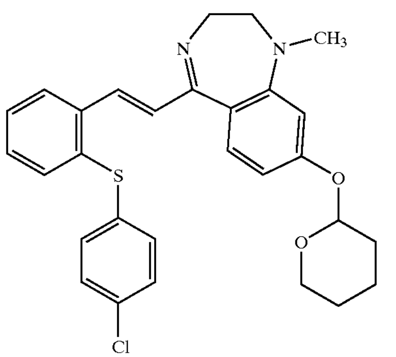 | (E)-5-[2-(4-Chlorophenylthio)styryl]-2,3-dihydro-8-(tetrahydro-2(RS)-pyranyloxy)-1-methyl-1H-1,4-benzodiazepine |
| 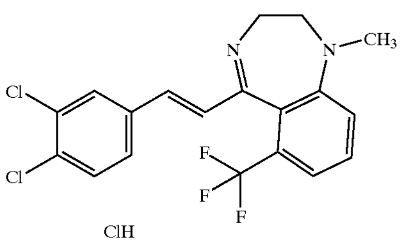 | (E)-5-(3,4-Dichlorostyryl)-6-(trifluoromethyl)-2,3-dihydro-1-methyl-1H-1,4-benzodiazepine dihydrochloride |
| 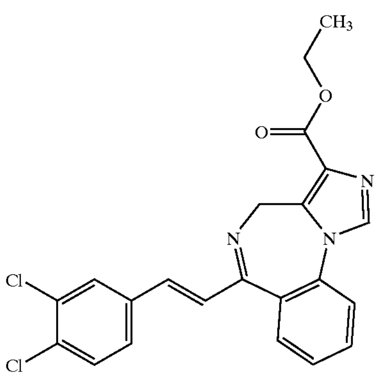 | Ethyl (E)-6-(3,4-dichlorostyryl)-4H-imidazo[1,5-a][1,4]benzo-diazepine-3-carboxylate |
| 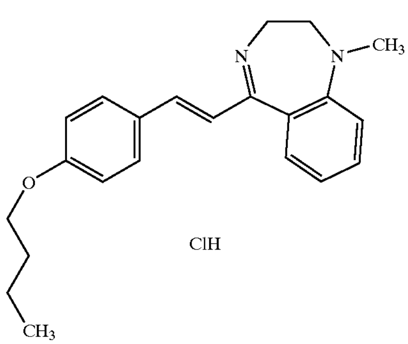 | (E)-5-(4-Butoxystyryl)-2,3-dihydro-1-methyl-1H-1,4-benzodiazepine dihydrochloride |

-continued

| Structure | Name |
|---|---|
| 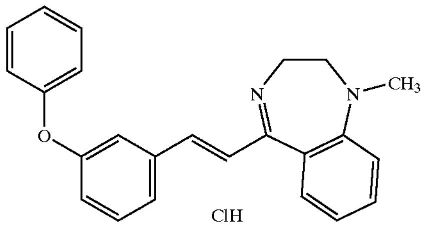 | (E)-2,3-Dihydro-1-methyl-5-(3-phenoxystyryl)-1H-1,4-benzodiazepine dihydrochloride |
| 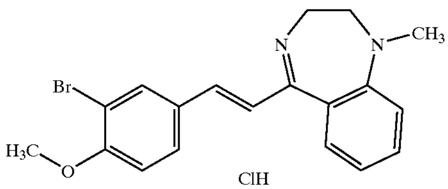 | (E)-5-(3-Bromo-4-methoxystyryl)-2,3-dihydro-1-methyl-1H-1,4-benzodiazepine dihydrochloride |
| 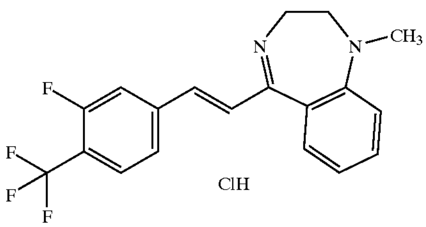 | (E)-5-[3-Fluoro-4-(trifluoromethyl)styryl]-2,3-dihydro-1-methyl-1H-benzo[e][1,4]diazepine dihydrochloride |
| 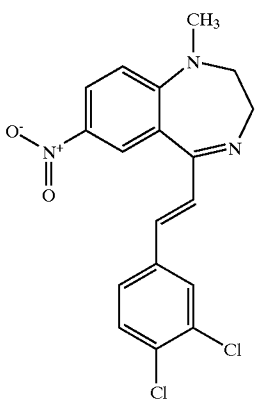 | (E)-5-(3,4-Dichlorostyryl)-2,3-dihydro-1-methyl-7-nitro-1H-1,4-benzodiazepine |
| 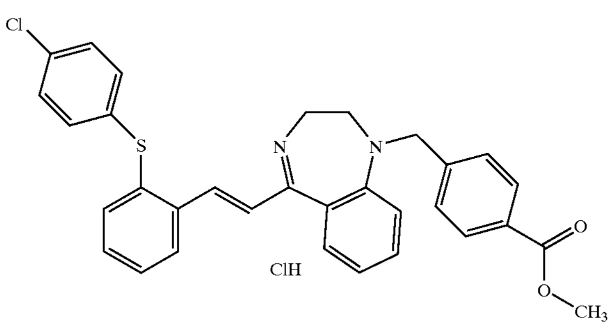 | Methyl (E)-4-[[5-[2-(4-Chlorophenylthio)styryl]-2,3-dihydro-1H-1,4-benzodiazepin-1-yl]methyl]benzoate hydrochloride |
| 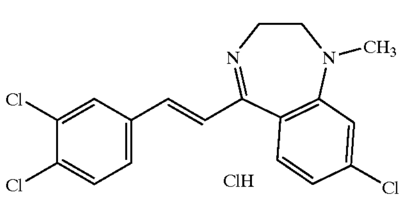 | (E)-8-Chloro-5-(3,4-dichlorostyryl)-2,3-dihydro-1-methyl-1H-1,4-benzodiazepine dihydrochloride |

-continued

| Structure | Name |
|---|---|
| 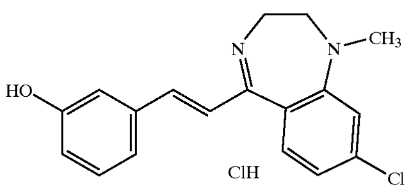 | (E)-3-[2-(8-Chloro-2,3-dihydro-1-methyl-1H-1,4-benzodiazepin-5-yl) vinyl]phenol hydrochloride |
| | (E)-5-(3,4-Dichlorostyryl)-2,3-dihydro-1-methyl-8-phenyl-1H-1,4-benzodiazepine dihydrochloride |
| 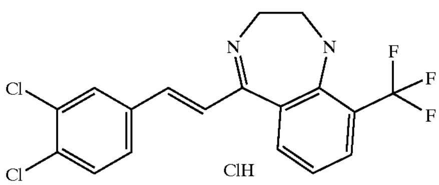 | (E)-5-(3,4-Dichlorostyryl)-9-(trifluoromethyl)-2,3-dihydro-1H-1,4-benzodiazepine dihydrochloride |
| 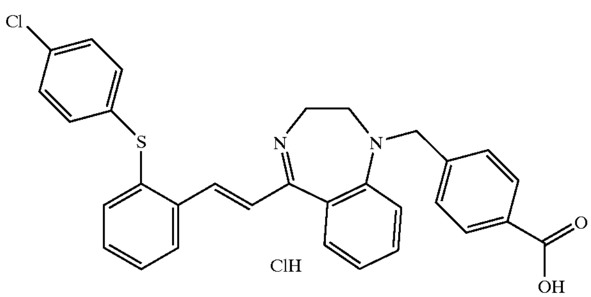 | (E)-4-[[5-[2-(4-Chlorophenylthio)styryl]-2,3-dihydro-1H-1,4-benzodiazepin-1-yl]methyl]benzoic acid hydrochloride |
| 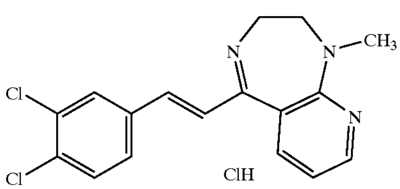 | (E)-5-(3,4-Dichlorostyryl)-2,3-dihydro-1-methyl-1H-pyrido[2,3-e][1,4]diazepine hydrochloride (1:3) |
| 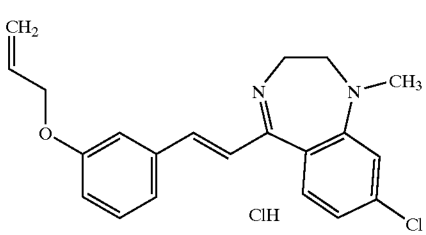 | (E)-5-(3-Allyloxystyryl)-8-chloro-2,3-dihydro-1-methyl-1H-1,4-benzodiazepine dihydrochloride |
| 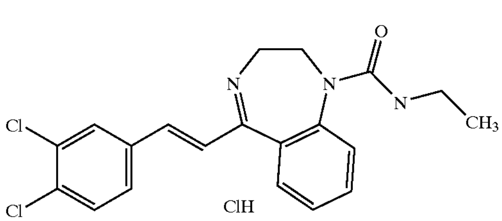 | (E)-5-(3,4-Dichlorostyryl)-N-ethyl-2,3-dihydro-1H-1,4-benzodiazepine-1-carboxamide |

-continued

| Structure | Name |
|---|---|
| 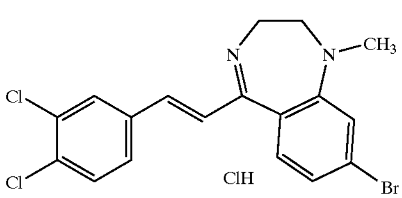 | (E)-8-Bromo-5-(3,4-dichlorostyryl)-2,3-dihydro-1-methyl-1H-1,4-benzodiazepine dihydrochloride |
| 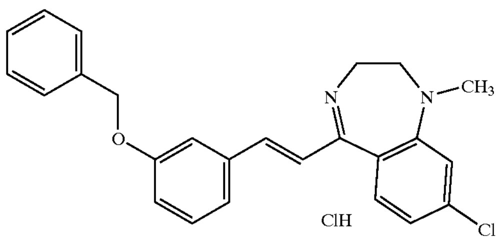 | (E)-5-(3-Benzyloxystyryl)-8-chloro-2,3-dihydro-1-methyl-1H-1,4-benzodiazepine dihydrochloride |
| 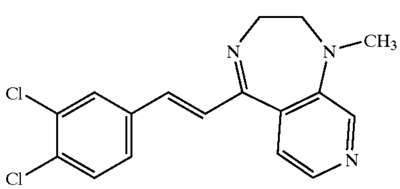 | (E)-5-(3,4-Dichlorostyryl)-2,3-dihydro-1-methyl-1H-pyrido[3,4-e][1,4]diazepine |
| 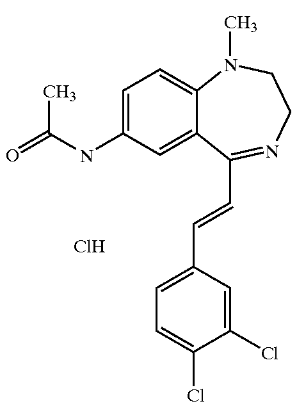 | (E)-5-(3,4-Dichlorostyryl)-2,3-dihydro-1-methyl-1H-1,4-benzodiazepin-7-acetamide hydrochloride |
| 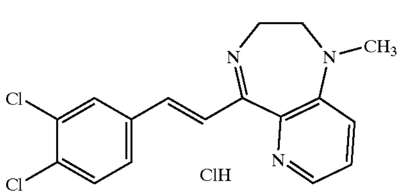 | (E)-5-(3,4-Dichlorostyryl)-2,3-dihydro-1-methyl-1H-pyrido[3,2-e][1,4]diazepine |

| Structure | Name |
|---|---|
| 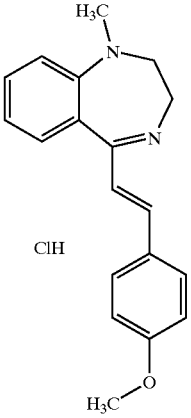 | (E)-2,3-Dihydro-5-(4-methoxystyryl)-1-methyl-1H-1,4-benzodiazepine hydrochloride |
| 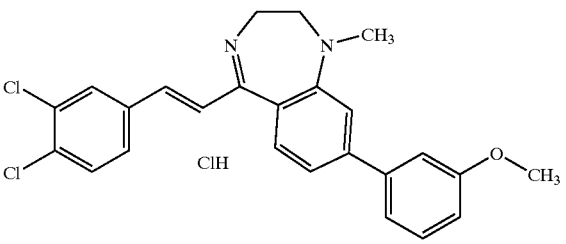 | (E)-5-(3,4-Dichlorostyryl)-2,3-dihydro-8-(3-methoxyphenyl)-1-methyl-1H-1,4-benzodiazepine dihydrochloride |
| 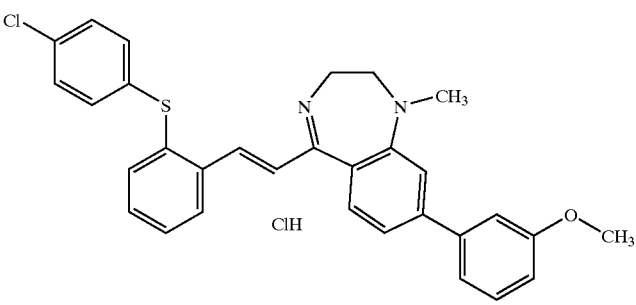 | (E)-5-[2-(4-Chlorophenylthio)-styryl]-2,3-dihydro-8-(3-methoxyphenyl)-1-methyl-1H-1,4-benzodiazepine dihydrochloride |
| 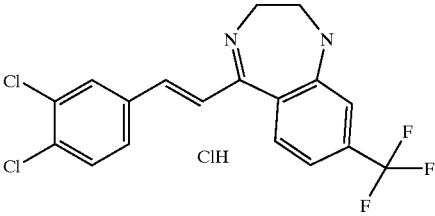 | (E)-5-(3,4-Dichlorostyryl)-8-(trifluoromethyl)-2,3-dihydro-1H-1,4-benzodiazepine hydrochloride |

-continued

| Structure | Name |
|---|---|
| 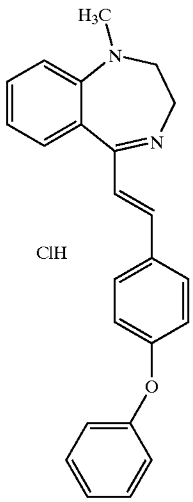 | (E)-2,3-Dihydro-1-methyl-5-(4-phenoxystyryl)-1H-1,4-benzodiazepine hydrochloride |
| 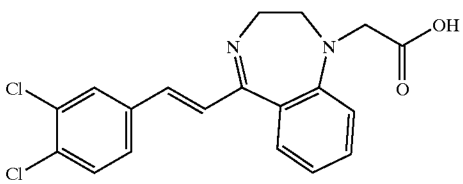 | (E)-5-(3,4-Dichlorostyryl)-2,3-dihydro-1H-1,4-benzodiazepine-1-acetic acid |
| 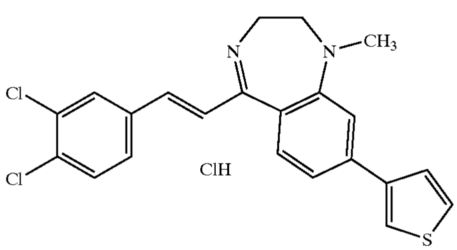 | (E)-5-(3,4-Dichlorostyryl)-2,3-dihydro-1-methyl-8-(3-thienyl)-1H-1,4-benzodiazepine dihydrochloride |
| 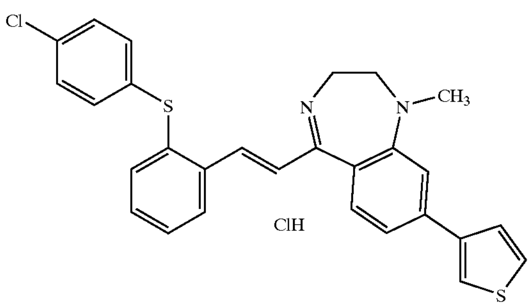 | (E)-5-[2-(4-Chlorophenylthio)styryl]-2,3-dihydro-1-methyl-8-(3-thienyl)-1H-1,4-benzodiazepine dihydrochloride |
| 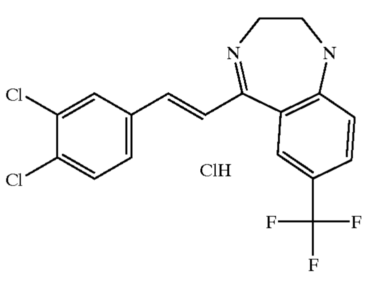 | (E)-5-(3,4-Dichlorostyryl)-7-(trifluoromethyl)-2,3-dihydro-1H-1,4-benzodiazepine hydrochloride |

-continued

| Structure | Name |
|---|---|
| 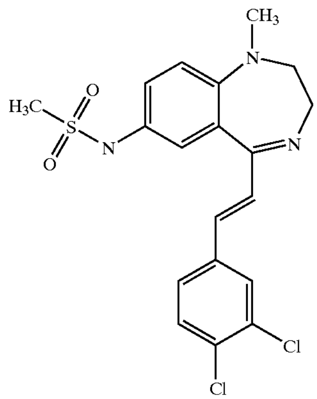 | (E)-N-[5-(3,4-Dichlorostyryl)-2,3-dihydro-1-methyl-1H-1,4-benzodiazepine-7-yl]methanesulfonamide |
| 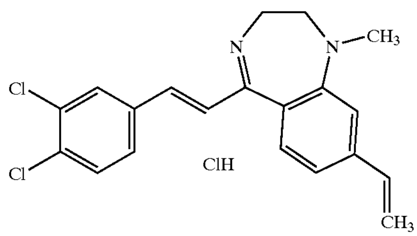 | 5-(3,4-Dichlorostyryl)-2,3-dihydro-1-methyl-8-vinyl-1H-1,4-benzodiazepine dihydrochloride |
| 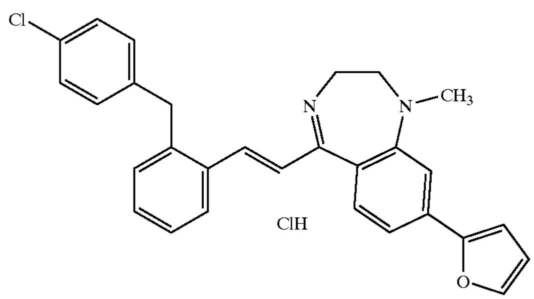 | (E)-5-[2-(4-Chlorophenylthio)styryl]-8-(2-furyl)-2,3-dihydro-1-methyl-1H-1,4-benzodiazepine dihydrochloride |
| 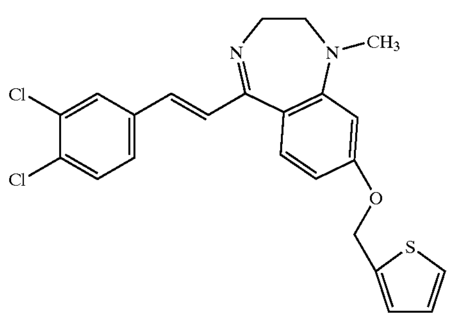 | (E)-5-(3,4-Dichlorostyryl)-2,3-dihydro-1-methyl-8-(2-thenyloxy)-1H-1,4-benzodiazepine |
| 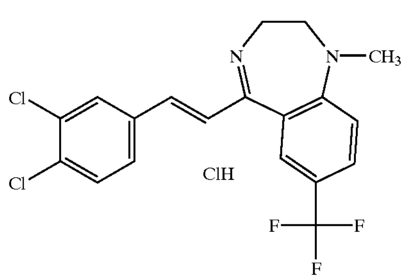 | (E)-5-(3,4-Dichlorostyryl)-7-(trifluoromethyl)-2,3-dihydro-1-methyl-1H-1,4-benzodiazepine hydrochloride |

-continued

| Structure | Name |
|---|---|
| 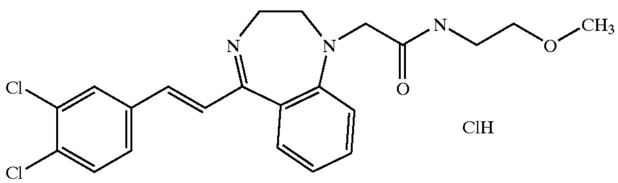 | (E)-5-(3,4-Dichlorostyryl)-2,3-dihydro-N-(2-methoxyethyl)-1H-1,4-benzodiazepin-1-acetamide dihydrochloride |
| 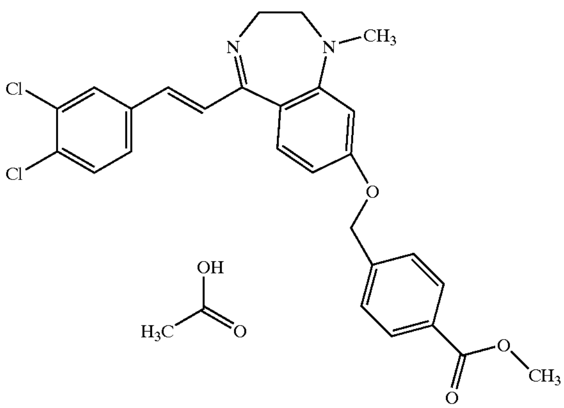 | Methyl (E)-4-[[5-(3,4-Dichlorostyryl)-2,3-dihydro-1-methyl-1H-1,4-benzodiazepin-8-yloxy]methyl]benzoate acetate (1:2) |
| 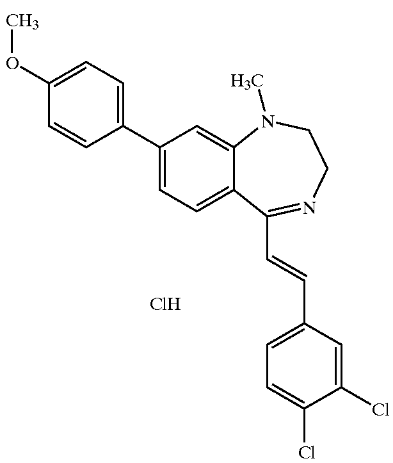 | (E)-5-(3,4-Dichlorostyryl)-2,3-dihydro-8-(4-methoxyphenyl)-1-methyl-1H-1,4-benzodiazepine |
| 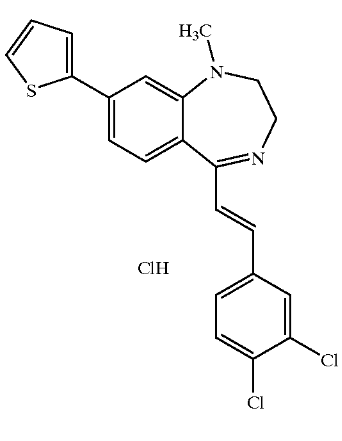 | (E)-5-(3,4-Dichlorostyryl)-2,3-dihydro-1-methyl-8-(2-thienyl)-1H-1,4-benzodiazepine hydrochloride |

-continued

| Structure | Name |
|---|---|
| 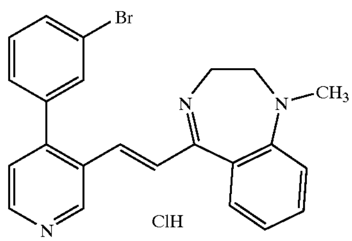 | (E)-5-[2-[4-(3-Bromophenyl)-3-pyridyl]vinyl]-2,3-dihydro-1-methyl-1H-1,4-benzodiazepine dihydrochloride |
| 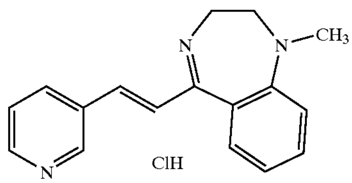 | (E)-2,3-Dihydro-1-methyl-5-[2-(3-pyridyl)vinyl]-1H-1,4-benzodiazepine dihydrochloride |
| 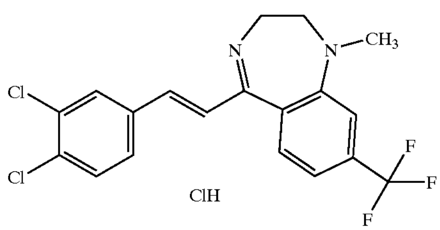 | (E)-5-(3,4-Dichlorostyryl)-8-(trifluoromethyl)-2,3-dihydro-1-methyl-1H-1,4-benzodiazepine hydrochloride |
| 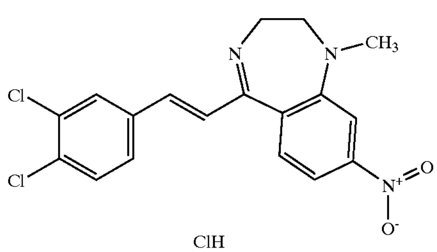 | (E)-5-(3,4-Dichlorostyryl)-2,3-dihydro-1-methyl-8-nitro-1H-1,4-benzodiazepine hydrochloride |
| 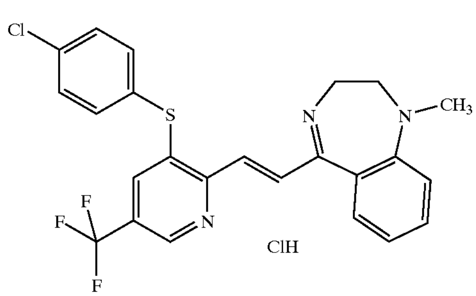 | (E)-5-[2-[3-(4-Chlorophenylthio)-5-(trifluoromethyl)-2-pyridyl]vinyl]-2,3-dihydro-1-methyl-1H-1,4-benzodiazepine dihydrochloride |

| Structure | Name |
|---|---|
| 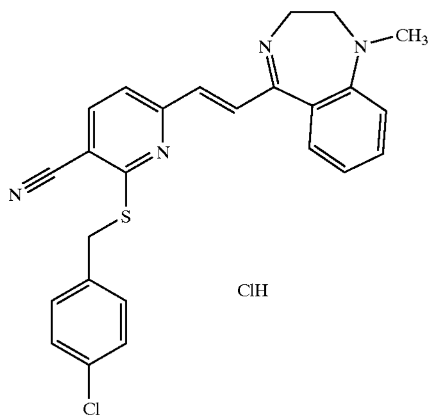 | (E)-2-(4-Chlorobenzylthio)-6-[2-(2,3-dihydro-1-methyl-1H-1,4-benzodiazepin-5-yl)vinyl]-3-pyridinecarbonitrile dihydrochloride |
| 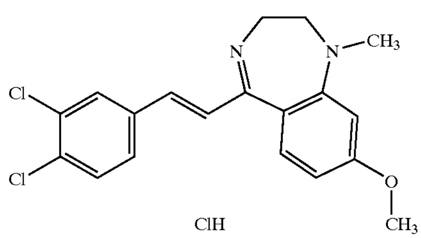 | (E)-5-(3,4-Dichlorostyryl)-2,3-dihydro-8-methoxy-1-methyl-1H-1,4-benzodiazepine hydrochloride |
| 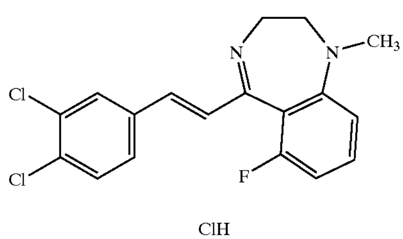 | (E)-5-(3,4-Dichlorostyryl)-6-fluoro-2,3-dihydro-1-methyl-1H-1,4-benzodiazepine hydrochloride |
| 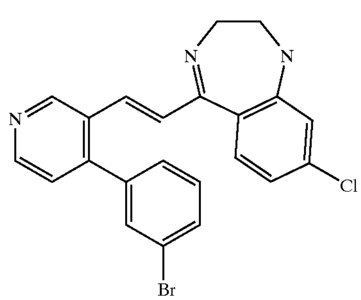 | (E)-5-[2-[4-(3-Bromophenyl)-3-pyridyl]vinyl]-8-chloro-2,3-dihydro-1H-1,4-benzodiazepine |
| 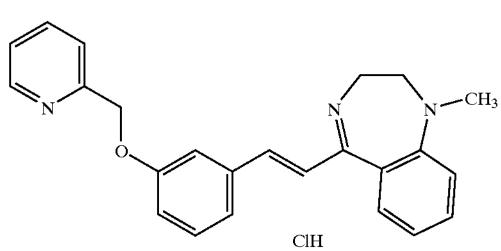 | (E)-2,3-Dihydro-1-methyl-5-[3-[(2-pyridyl)methoxy]styryl]-1H-1,4-benzodiazepine dihydrochloride |

-continued

| Structure | Name |
|---|---|
| 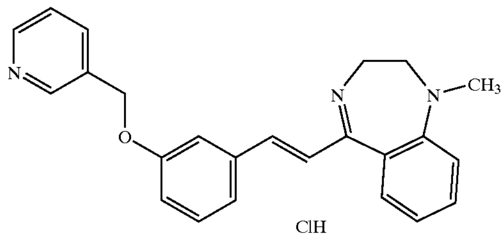 | (E)-2,3-Dihydro-1-methyl-5-[3-[(3-pyridyl)methyl]styryl]-1H-1,4-benzodiazepine dihydrochloride |
| 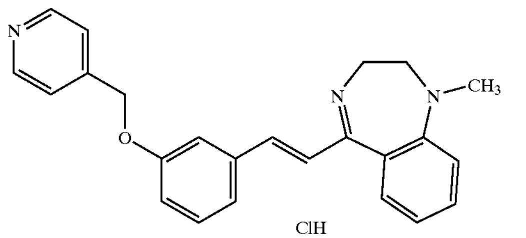 | (E)-2,3-Dihydro-1-methyl-5-[3-[(4-pyridyl)methoxy]styryl]-1H-1,4-benzodiazepine dihydrochloride |
| 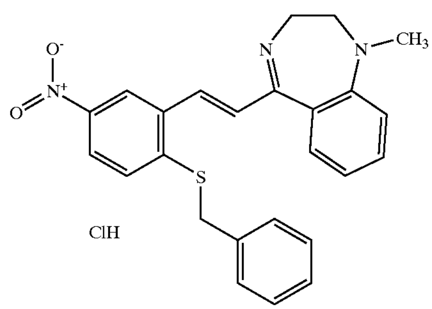 | (E)-5-(2-Benzylthio-5-nitrostyryl)-2,3-dihydro-1-methyl-1H-1,4-benzodiazepine dihydrochloride |
| 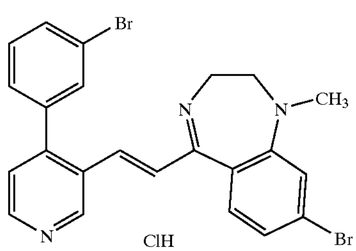 | (E)-8-Bromo-5-[2-[4-(3-bromophenyl)-3-pyridyl]vinyl]-2,3-dihydro-1-methyl-1H-1,4-benzodiazepine dihydrochloride |
| 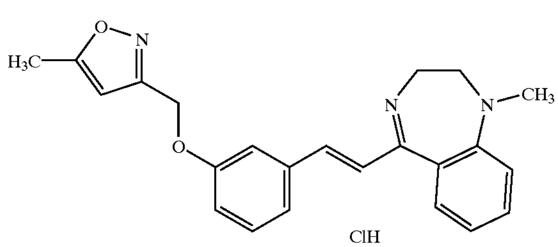 | (E)-2,3-Dihydro-1-methyl-5-[3-[(5-methyl-3-isoxazol-3-yl)methoxy]styryl]-1H-1,4-benzodiazepine dihydrochloride |
| 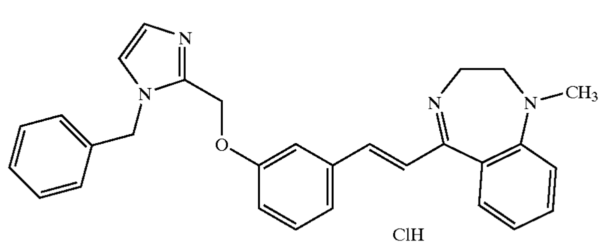 | (E)-5-[3-[(1-Benzyl-1H-imidazol-2-yl)methoxy]styryl]-2,3-dihydro-1-methyl-1H-1,4-benzodiazepine dihydrochloride |

-continued

| Structure | Name |
|---|---|
| 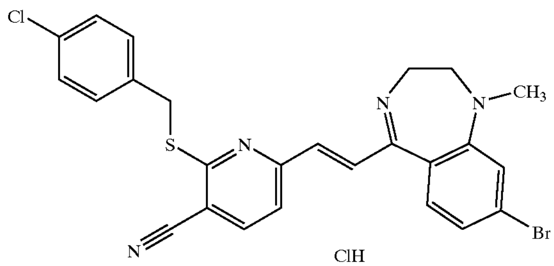 | (E)-6-[2-(8-Bromo-2,3-dihydro-1-methyl-1H-1,4-benzodiazepin-5-yl)vinyl]-2-(4-chlorobenzylthio)-3-pyridinecarbonitrile dihydrochloride |
| 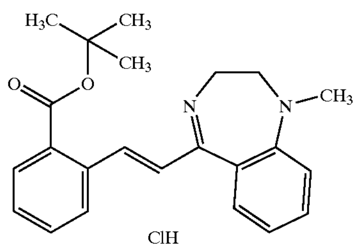 | tert-Butyl (E)-2-[2-(2,3-dihydro-1-methyl-1H-1,4-benzodiazepin-5-yl)vinyl]benzoate dihydrochloride |
| 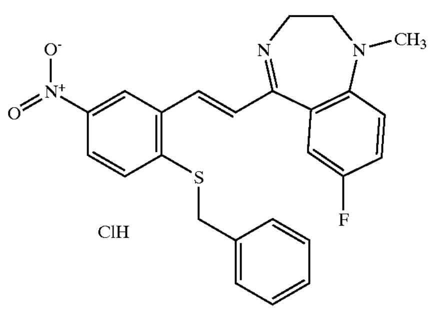 | (E)-5-(2-Benzylthio-5-nitrostyryl)-7-fluoro-2,3-dihydro-1-methyl-1H-1,4-benzodiazepine dihydrochloride |
| 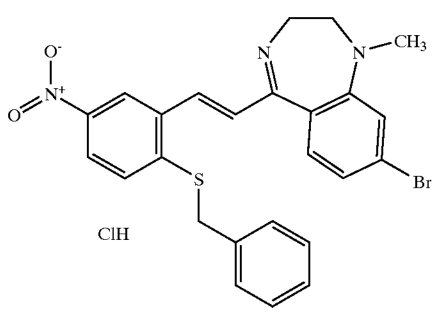 | (E)-5-(2-Benzylthio-5-nitrostyryl)-8-bromo-2,3-dihydro-1-methyl-1H-1,4-benzodiazepine dihydrochloride |
| 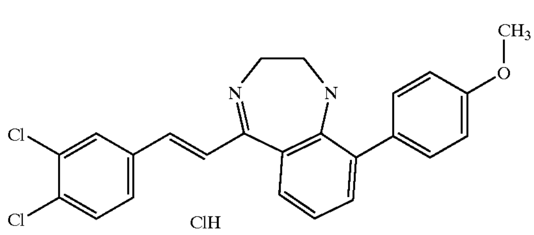 | (E)-5-(3,4-Dichlorostyryl)-2,3-dihydro-9-(4-methoxyphenyl)-1H-1,4-benzodiazdepine hydrochloride |

-continued

| Structure | Name |
|---|---|
| 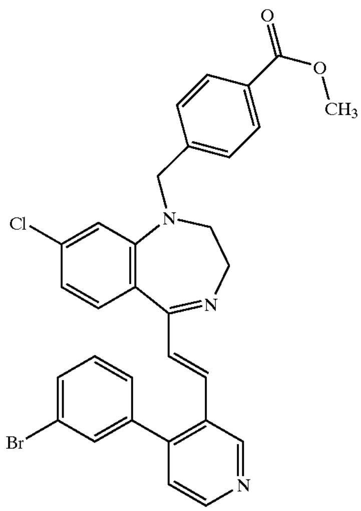 | Methyl (E)-4-[[5-[2-[4-(3-bromophenyl)-3-pyridyl]vinyl]-8-chloro-2,3-dihydro-1,4-benzodiazepine-1-yl]methyl]benzoate |
| 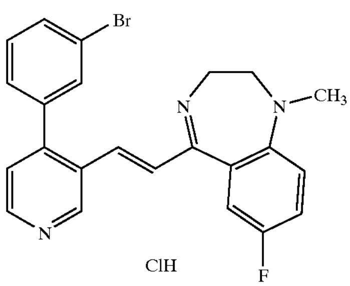 | (E)-5-[4-(3-Bromophenyl)-3-pyridyl]-7-fluoro-2,3-dihydro-1-methyl-1H-1,4-benzodiazepine dihydrochloride |
| 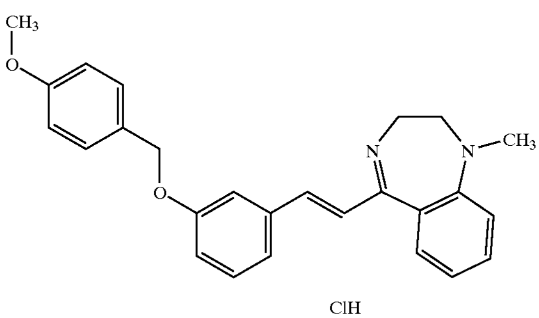 | (E)-5-[2,3-Dihydro-3-(4-methoxybenzyloxy)styryl]-1-methyl-1H-1,4-benzodiazepine dihydrochloride |
| 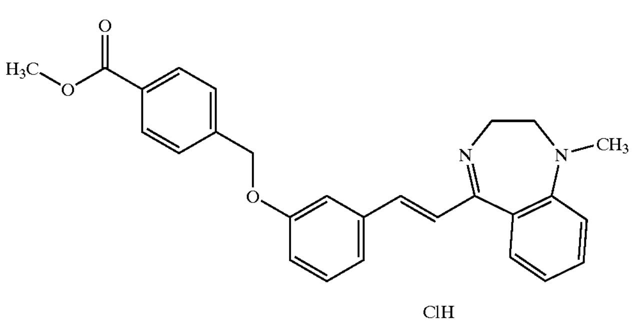 | Methyl (E)-4-[[3-[2-(2,3-dihydro-1-methyl-1H-1,4-benzodiazepin-5-yl)vinyl]phenoxy]methyl]benzoate dihydrochloride |

-continued

| Structure | Name |
|---|---|
| 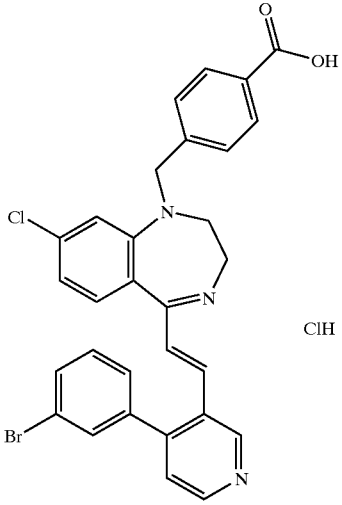 | (E)-4-[[5-[2-[4-(3-Bromophenyl)-3-pyridyl]vinyl]-8-chloro-2,3-dihydro-1,4-benzodiazepin-1-yl]methyl]benzoic acid hydrochloride |
| 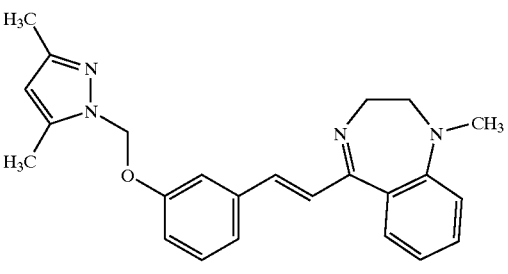 | (E)-2,3-Dihydro-1-methyl-5-[3-[(3,5-dimethyl-1-pyrazol)methoxy]styryl]-1H-1,4-benzodiazepine dihydrochloride |
| 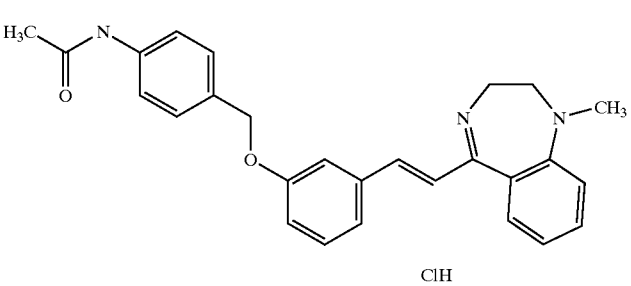 | (E)-4'-[[3-[2-(2,3-Dihydro-1-methyl-1H-1,4-benzodiazepin-5-yl)vinyl]phenyl]methyl]acetanilide hydrochloride |
| 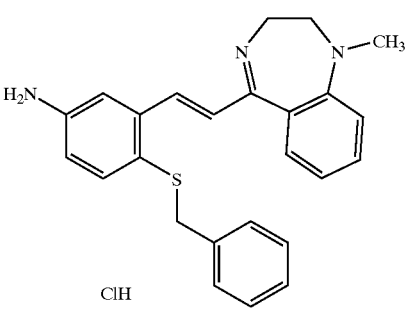 | (E)-4-Benzylthio-3-[2-(2,3-dihydro-1-methyl-1H-1,4-benzodiazepin-5-yl)vinyl]aniline hydrochloride |

-continued

| Structure | Name |
|---|---|
| 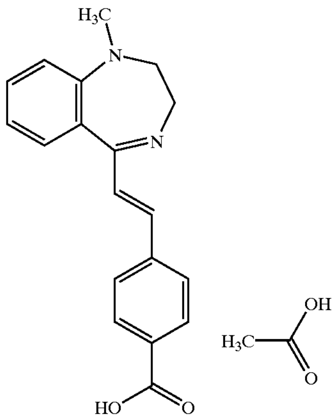 | (E)-4[2-(2,3-Dihydro-1-methyl-1H-1,4-benzodiazepin-5-yl)vinyl]benzoic acid acetate (1:1) |
| 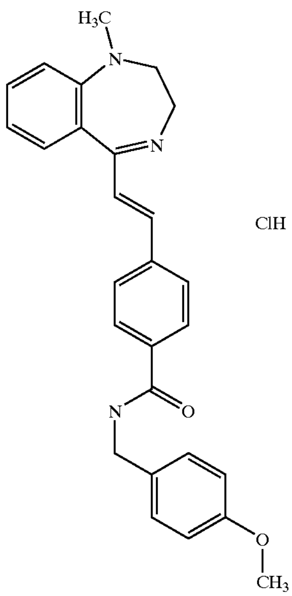 | (E)-4-[2-(2,3-Dihydro-1-methyl-1H-1,4-benzodiazepin-5-yl)vinyl]-N-(4-methoxybenyl)benzamide hydrochloride |
| 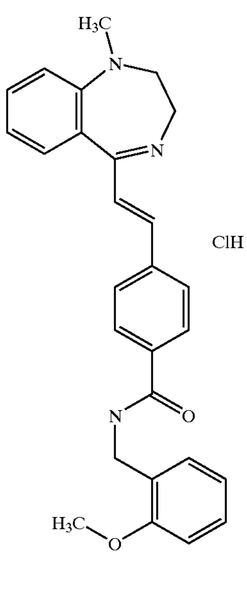 | (E)-4-[2-(2,3-Dihydro-1-methyl-1H-1,4-benzodiazepin-5-yl)vinyl]-N-(2-methoxybenzyl)benzamide hydrochloride |

-continued

| Structure | Name |
|---|---|
| 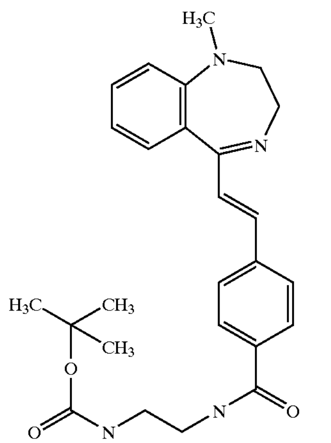 | tert-Butyl (E)-[2-[4-[2-(2,3-dihydro-1-methyl-1H-1,4-benzodiazepin-5-yl)-vinyl]-benzoamido]ethyl)]carbamate |
| 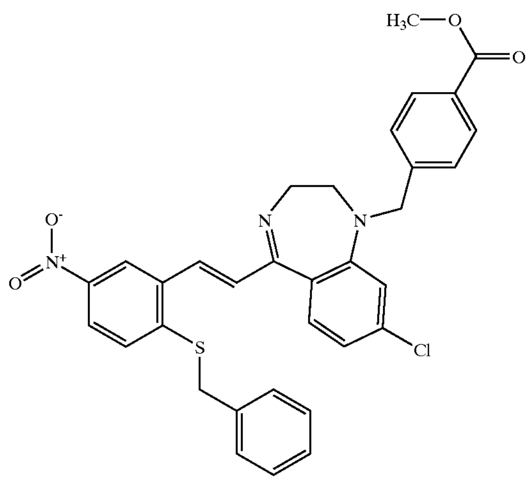 | Methyl (E)-4-[[5-(2-benzylthio-5-nitrostyryl)-8-chloro-2,3-dihydro-1,4-benzodiazepin-1-yl]methyl]benzoate |
| 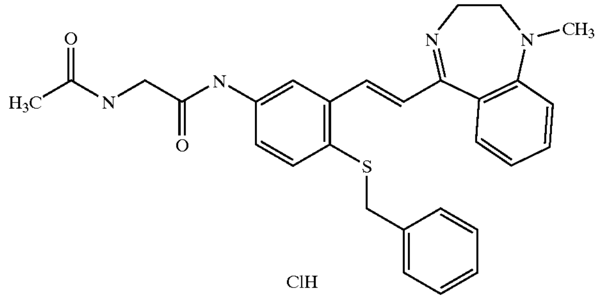 | (E)-2-Acetamido-4'-benzylthio-3'-[2-(2,3-dihydro-1-methyl-1H-1,4-benzodiazepin-5-yl)vinyl]acetanilide dihydrochloride |

-continued
| Structure | Name |
|---|---|
| 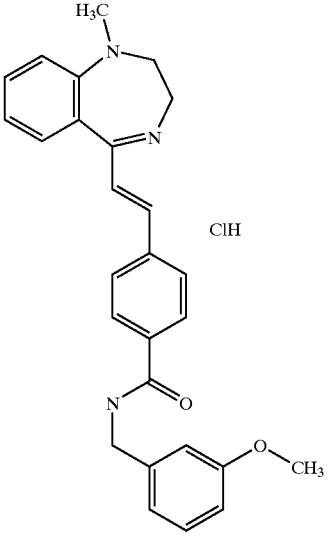 | (E)-4-[2-(2,3-Dihydro-1-methyl-1H-1,4-benzodiazepin-5-yl)vinyl]-N-(3-methoxybenzyl)benzamide hydrochloride |
| 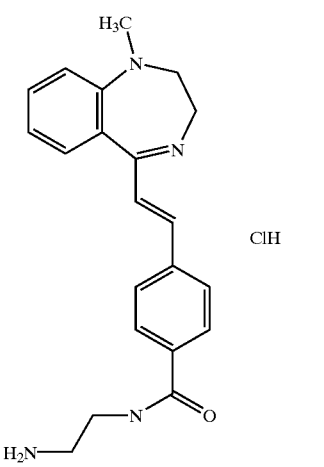 | (E)-N-(2-Aminoethyl)-4-[2-(2,3-dihydro-1-methyl-1H-1,4-benzodiazepin-5-yl)vinyl]benzamide hydrochloride |
| 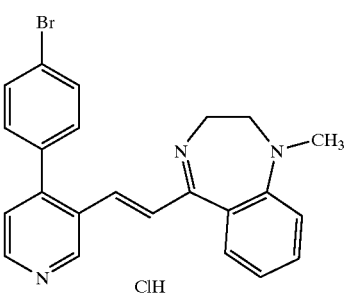 | (E)-5-[2-[4-(4-Bromophenyl)-3-pyridyl]vinyl]-2,3-dihydro-1-methyl-1H-1,4-benzodiazepine dihydrochloride |
| 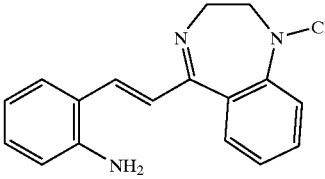 | (E)-2-[2-(2,3-Dihydro-1-methyl-1H-1,4-benzodiazepine-5-yl)vinyl]aniline hydrochloride |

-continued

| Structure | Name |
|---|---|
| 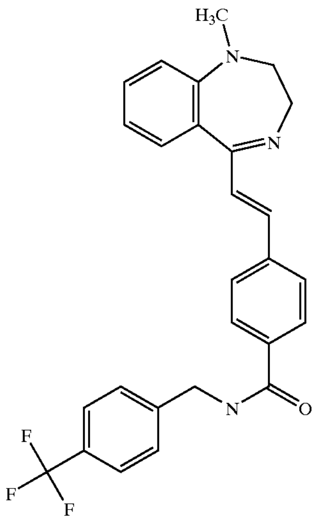 | (E)-N-[4-(Trifluoromethyl)benzyl]-4-[2-(2,3-dihydro-1-methyl-1H-1,4-benzodiazepin-5-yl)vinyl]benzamide |
| 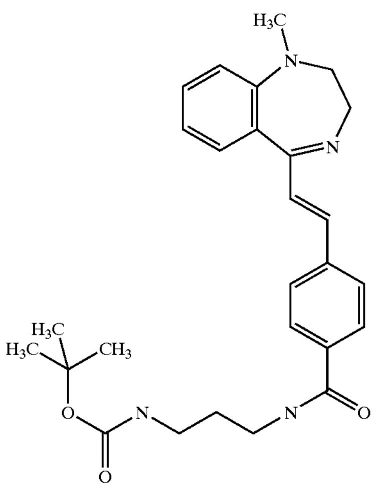 | tert-Butyl (E)-[3-[4-[2-(2,3-dihydro-1-methyl-1H-1,4-benzodiazepin-5-yl)vinyl]benzoamido]propyl]carbamate |
| 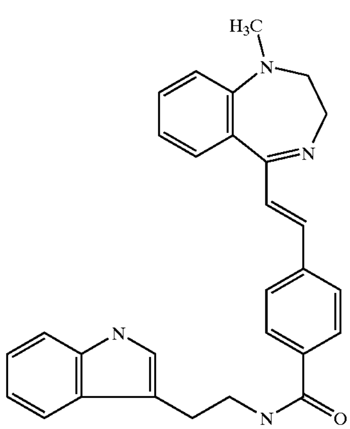 | (E)-4-[2-(2,3-Dihydro-1-methyl-1H-1,4-benzodiazepin-5-yl)vinyl]-N-[2-(1H-indol-3-yl)ethyl]benzamide |

-continued

| Structure | Name |
|---|---|
| 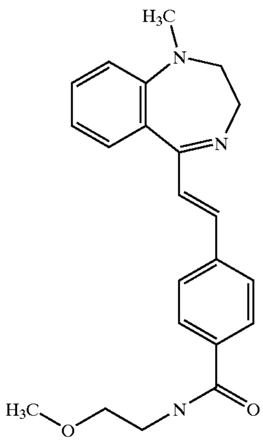 | (E)-4-[2-(2,3-Dihydro-1-methyl-1H-1,4-benzodiazepin-5-yl)vinyl]-N-(2-methoxyethyl)benzamide |
| 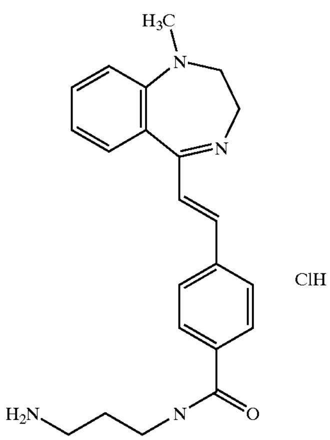 | (E)-N-(3-Aminopropyl)-4-[2-(2,3-dihydro-1-methyl-1H-1,4-benzodazepin-5-yl)vinyl]benzamide hydrochloride |
| 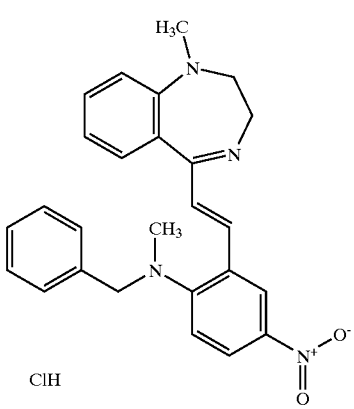 | (E)-2-[2-(2,3-Dihydro-1-methyl-1H-1,4-benzodiazepin-5-yl)vinyl]-N-methyl-4-nitroaniline dihydrochloride |

-continued
| Structure | Name |
|---|---|
| 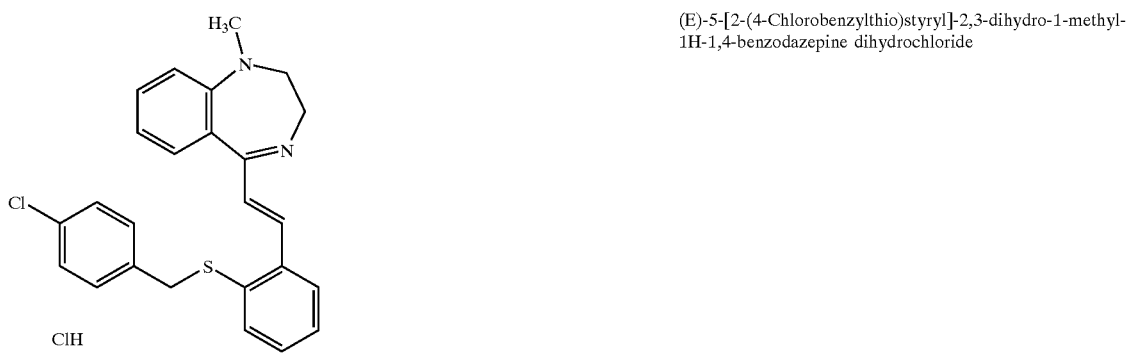 | (E)-5-[2-(4-Chlorobenzylthio)styryl]-2,3-dihydro-1-methyl-1H-1,4-benzodazepine dihydrochloride |
| 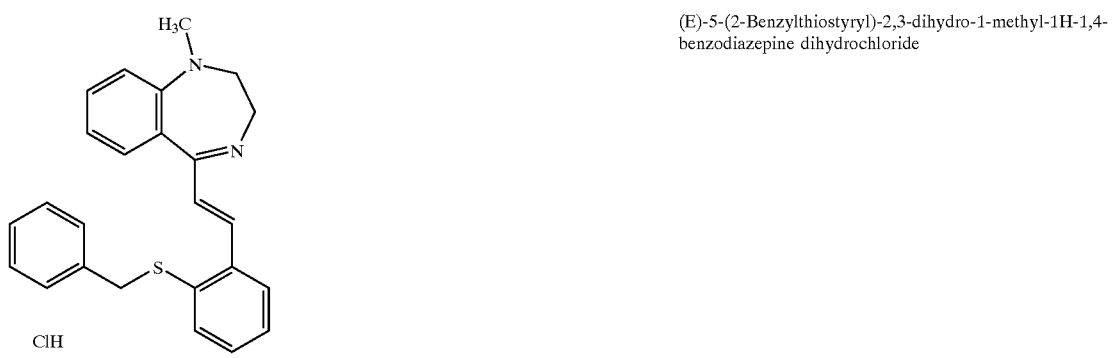 | (E)-5-(2-Benzylthiostyryl)-2,3-dihydro-1-methyl-1H-1,4-benzodiazepine dihydrochloride |
| 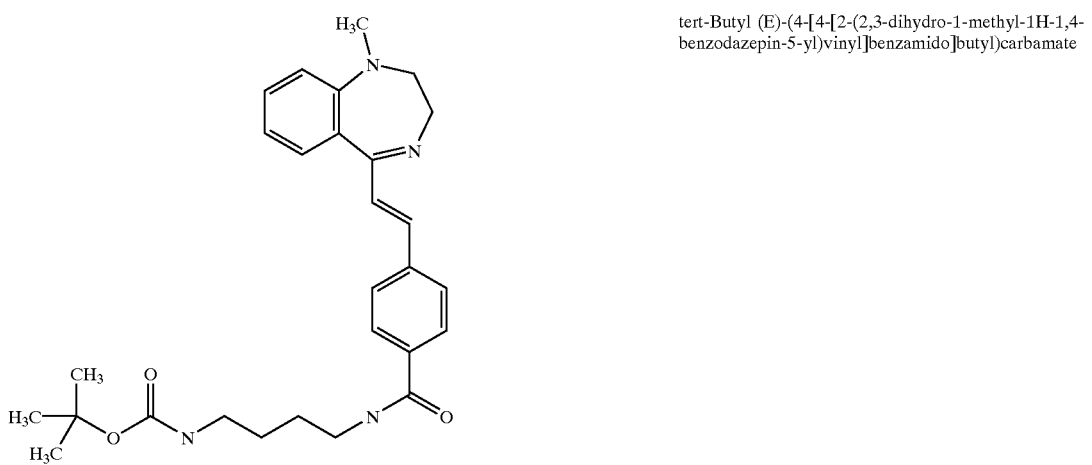 | tert-Butyl (E)-(4-[4-[2-(2,3-dihydro-1-methyl-1H-1,4-benzodazepin-5-yl)vinyl]benzamido]butyl)carbamate |

-continued

| Structure | Name |
|---|---|
| 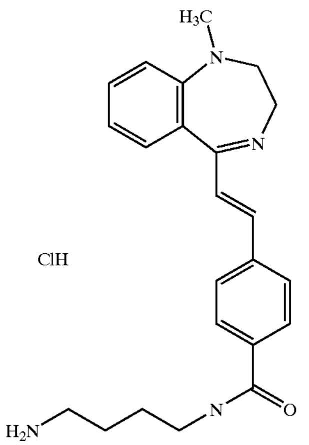 | (E)-N-(4-Aminobutyl)-4-[2-(2,3-dihydro-1-methyl-1H-1,4-benzodiazepin-5-yl)vinyl]benzamide hydrochloride |
| 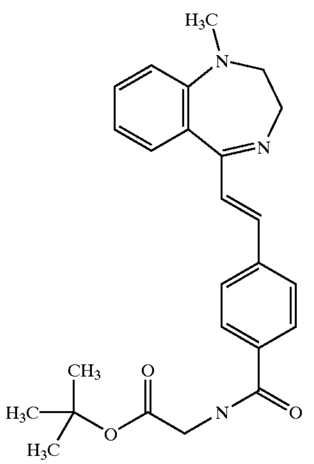 | tert-Butyl (E)-[4-[2-(2,3-dihydro-1-methyl-1H-1,4-benzodiazepin-5-yl)vinyl]benzamido]acetate |
| 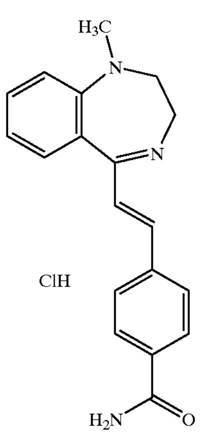 | (E)-4-[2-(2,3-Dihydro-1-methyl-1H-1,4-benzodiazepin-5-yl)vinyl]benzamide hydrochloride |

-continued
| Structure | Name |
|---|---|
| 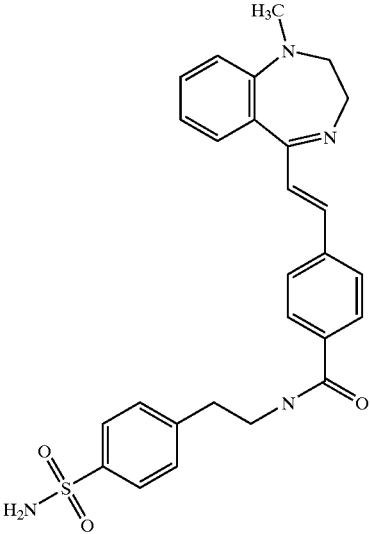 | (E)-4-[2-(2,3-Dihydro-1-methyl-1H-1,4-benzodiazepin-5-yl)vinyl]-N-[2-(4-sulfamoylphenyl)ethyl]benzamide |
| 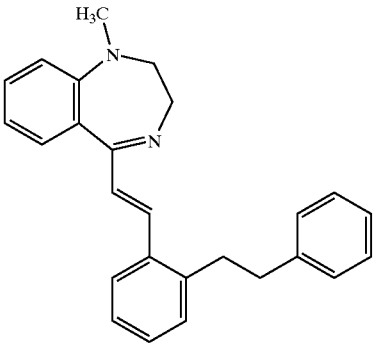 | (E)-2,3-Dihydro-1-methyl-5-[2-(2-phenylethyl)styryl]-1H-1,4-benzodiazepine |
| 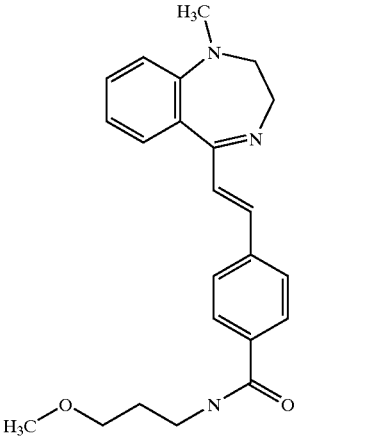 | (E)-4-[2-(2,3-Dihydro-1-methyl-1H-1,4-benzodiazepin-5-yl)vinyl]-N-(3-methoxypropyl)benzamide |

-continued

| Structure | Name |
|---|---|
| 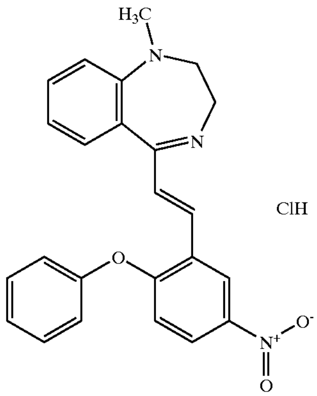 | (E)-2,3-Dihydro-1-methyl-5-(5-nitro-2-phenoxystyryl)-1H-1,4-benzodiazepine dihydrochloride |
| 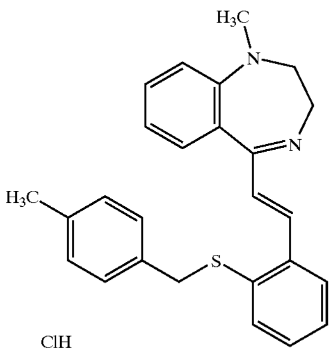 | (E)-2,3-Dihydro-1-methyl-5-[2-(4-methylbenzylthio)styryl]-1H-1,4-benzodiazepine dihydrochloride |
| 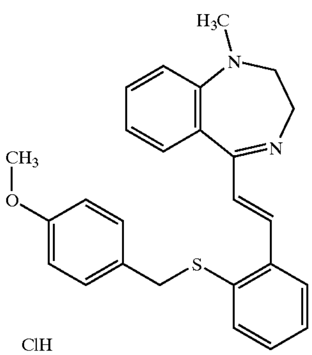 | (E)-2,3-Dihydro-5-[2-(4-methoxybenzylthio)styryl]-1-methyl-1H-1,4-benzodiazepine dihydrochloride |
| 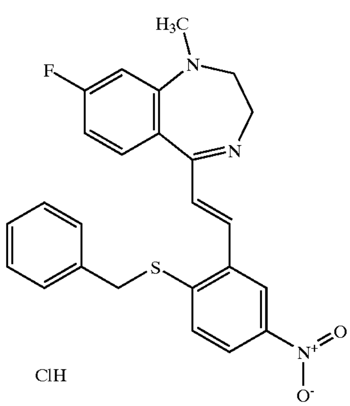 | (E)-5-(2-Benzylthio-5-nitrostyryl)-8-fluoro-2,3-dihydro-1-methyl-1H-1,4-benzodiazepine dihydrochloride |

-continued
| Structure | Name |
|---|---|
| 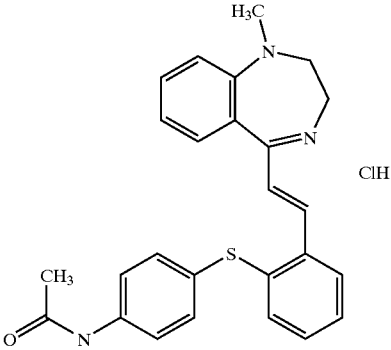 | (E)-4'-[2-[2-(2,3-Dihydro-1-methyl-1H-1,3-benzodiazepin-5-yl)vinyl]phenylthio]acetanilide hydrochloride |
| 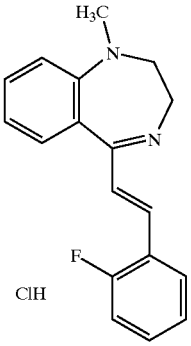 | (E)-5-(2-Fluorostyryl)-2,3-dihydro-1-methyl-1H-1,4-benzodiazepine dihydrochloride |
| 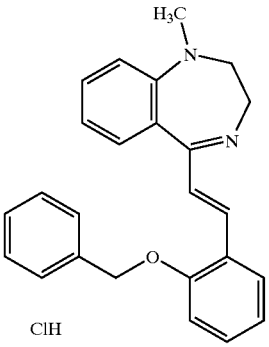 | (E)-5-(2-Benzyloxystyryl)-2,3-dihydro-1-methyl-1H-1,4-benzodiazepine dihydrochloride |
| 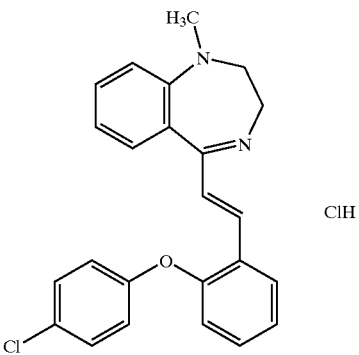 | (E)-5-[2-(4-Chlorophenoxy)styryl]-2,3-dihydro-1-methyl-1H-1,4-benzodiazepine dihydrochloride |

| Structure | Name |
|---|---|
| 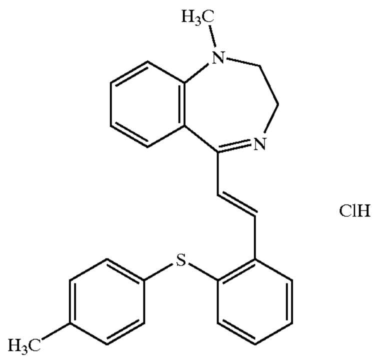 | (E)-2,3-Dihydro-1-methyl-5-(2-p-tolylthiostyryl)-1H-1,4-benzodiazepine dihydrochloride |
| 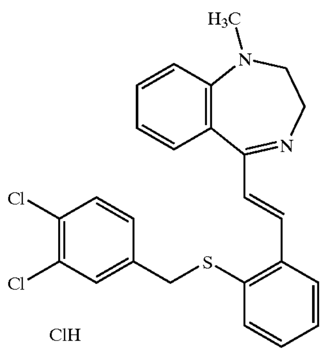 | (E)-5-[2-(3,4-Dichlorobenzylthio)styryl]-2,3-dihydro-1-methyl-1H-1,4-benzodiazepine dihydrochloride |
| 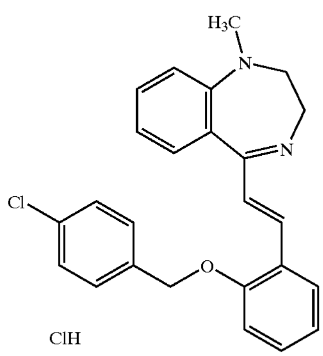 | (E)-5-[2-(4-Chlorobenzyloxy)styryl]-2,3-dihydro-1-methyl-1H-1,4-benzodiazepine dihydrochloride |
| 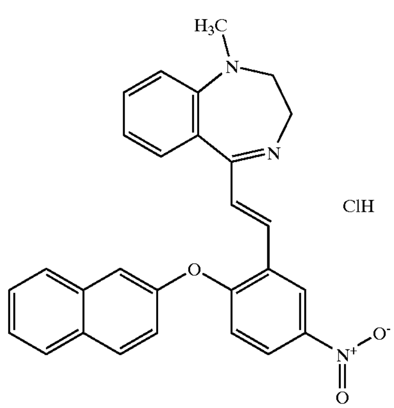 | (E)-2,3-Dihydro-1-methyl-5-[2-(2-naphthyloxy)-5-nitrostyryl]-1H-1,4-benzodiazepine dihydrochloride |

-continued

| Structure | Name |
|---|---|
| 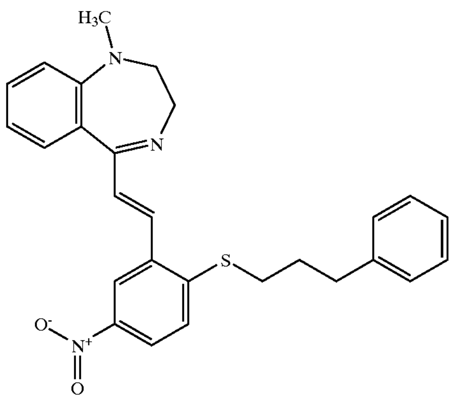 | (E)-2,3-Dihydro-1-methyl-5-[5-nitro-2-(3-phenylpropylthio)styryl]-1H-1,4-benzodiazepine |
| 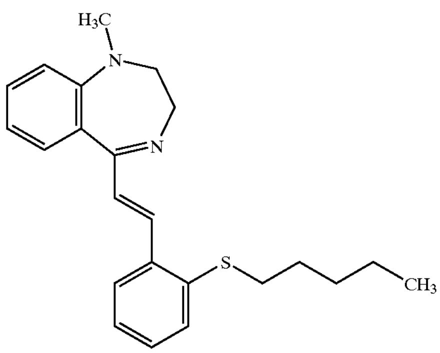 | (E)-2,3-Dihydro-1-methyl-5-(2-pentylthiostyryl)-1H-1,4-benzodiazepine |
| 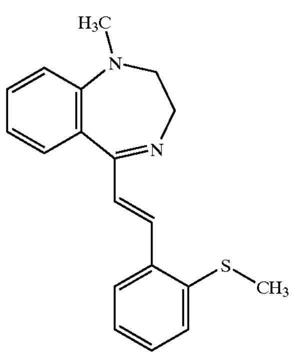 | (E)-2,3-Dihydro-1-methyl-5-(2-methylthiostyryl)-1H-1,4-benzodiazepine |
| 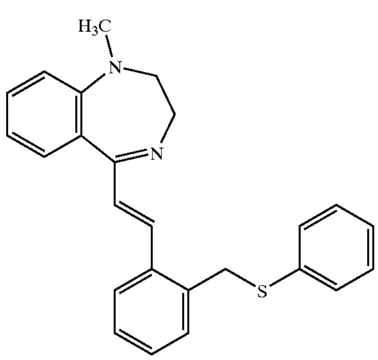 | (E)-2,3-Dihydro-1-methyl-5-[2-(phenylthiomethyl)styryl]-1H-1,4-benzodiazepine |

-continued

| Structure | Name |
|---|---|
| 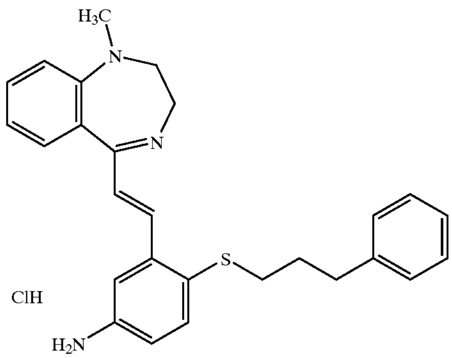 | (E)-3-[2-(2,3-Dihydro-1-methyl-1H-1,4-benzodiazepin-5-yl)vinyl]-4-(3-phenylpropylthio)aniline hydrochloride |
| 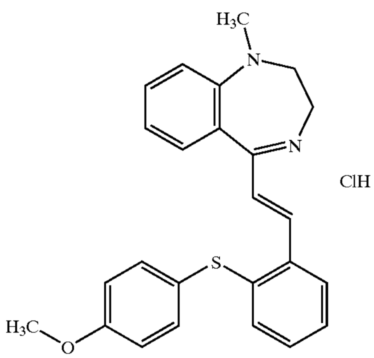 | (E)-2,3-Dihydro-5-[2-(4-methoxyphenylthio)styryl]-1-methyl-1H-1,4-benzodiazepine dihydrochloride |
| 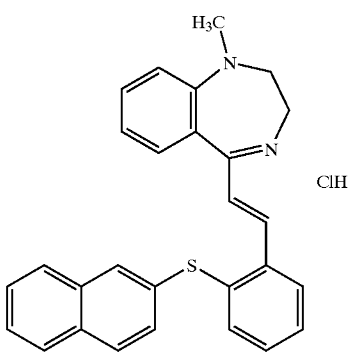 | (E)-2,3-Dihydro-1-methyl-5-[2-(2-naphthylthio)styryl]-1H-1,4-benzodiazepine dihydrochloride |
| 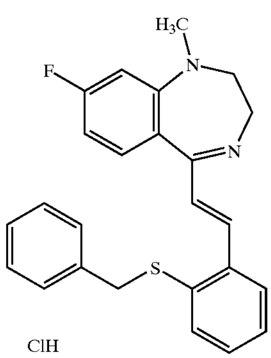 | (E)-5-(2-Benzylthiostyryl)-8-fluoro-2,3-dihydro-1-methyl-1H-1,4-benzodiazepine dihydrochloride |

-continued

| Structure | Name |
|---|---|
| 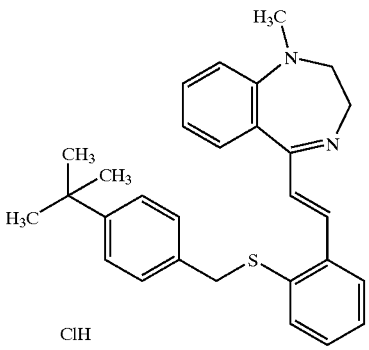 | (E)-5-[2-(4-tert-Butyl-benzylthio)styryl]-2,3-dihydro-1-methyl-1H-1,4-benzodiazepine dihydrochloride |
| 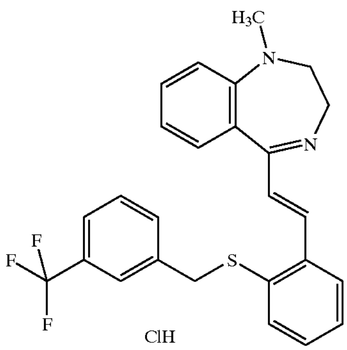 | (E)-5-[2-[3-(Trifluoromethyl)benzylthio]styryl]-23,-dihydro-1-methyl-1H-1,4-benzodiazepine dihydrochloride |
| 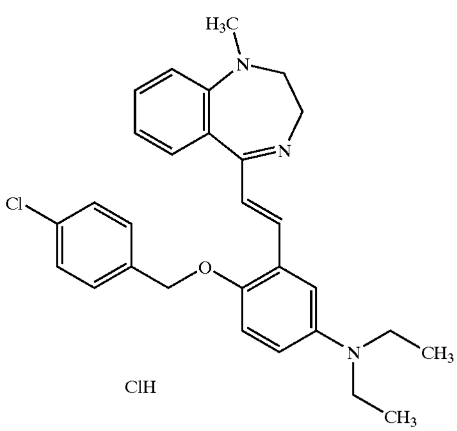 | (E)-4-(4-Chlorobenzyloxy)-3-[2-(2,3-dihydro-1-methyl-1H-1,4-benzodiazepin-5-yl)vinyl]-N,N-diethylaniline dihydrochloride |
| 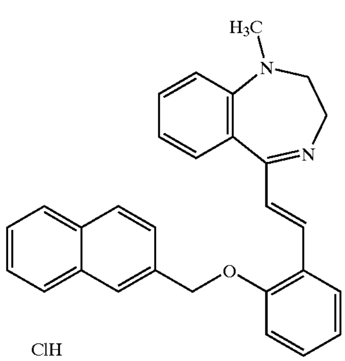 | (E)-2,3-Dihydro-1-methyl-5-[2-[(2-naphthyl)methoxy]-styryl]-1H-1,4-benzodiazepine dihydrochloride |

-continued

| Structure | Name |
|---|---|
| 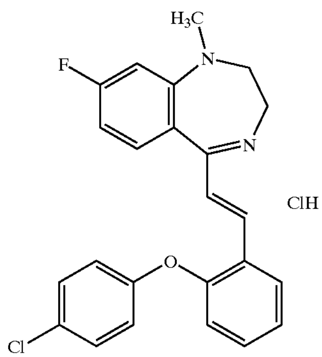 | (E)-5-[2-(4-Chlorophenoxy)styryl]-8-fluoro-2,3-dihydro-1-methyl-1H-1,4-benzodiazepine dihydrochloride |
| 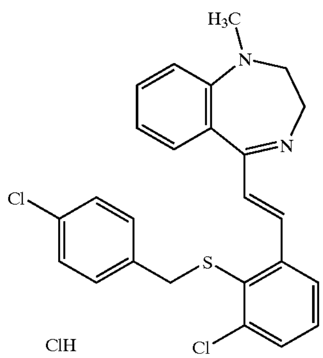 | (E)-5-[3-Chloro-2-(4-chlorobenzylthio)styryl]-2,3-dihydro-1-methyl-1H-1,4-benzodiazepine dihydrochloride |
| 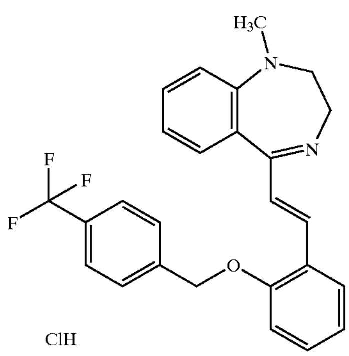 | (E)-5-[2-[4-(Trifluoromethyl)benzyloxy]styryl]-2,3-dihydro-1-methyl-1H-1,4-benzodiazepine dihydrochloride |
| 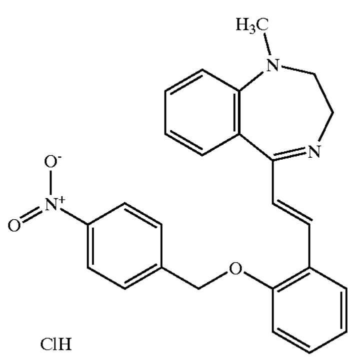 | (E)-2,3-Dihydro-1-methyl-5-[2-(4-nitrobenzyloxy)styryl]-1H-1,4-benzodiazepine dihydrochloride |

-continued

| Structure | Name |
|---|---|
| 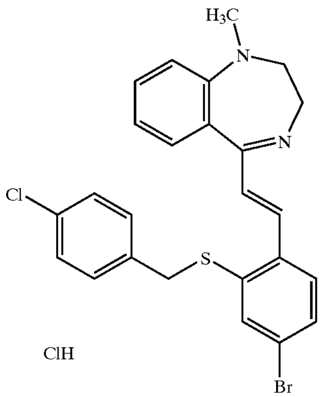 | (E)-5-[4-Bromo-2-(4-chlorobenzylthio)styryl]-2,3-dihydro-1-methyl-1H-1,4-benzodiazepine dihydrochloride |
| 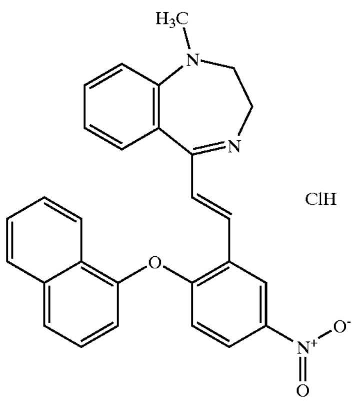 | (E)-2,3-Dihydro-1-methyl-5-[2-(1-naphthyloxy)-5-nitrostyryl]-1H-1,4-benzodiazepine dihydrochloride |
| 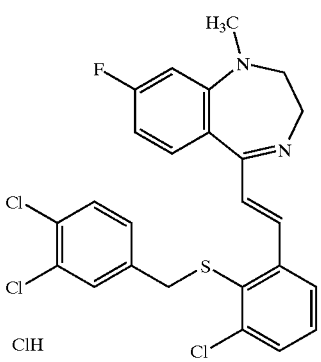 | (E)-5-[3-Chloro-2-(3,4-dichlorobenzylthio)phenyl]-8-fluoro-2,3-dihydro-1-methyl-1H-1,4-benzodiazepine dihydrochloride |
| 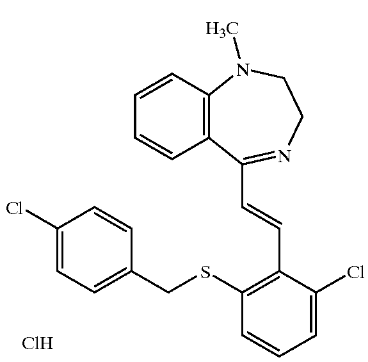 | (E)-5-[2-Chloro-6-(4-chlorobenzylthio)styryl]-2,3-dihydro-1-methyl-1H-1,4-benzodiazepine hydrochloride |

| Structure | Name |
|---|---|
| 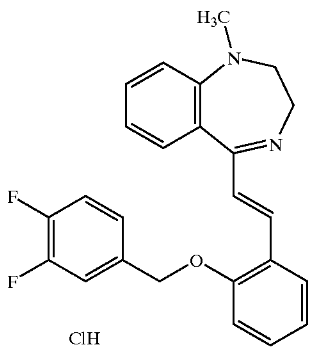 | (E)-5-[2-(3,4-Difluorobenzyloxy)styryl]-2,3-dihydro-1-methyl-1H-1,4-benzodiazepine dihydrochloride |
| 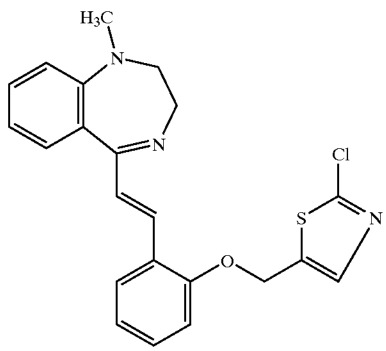 | (E)-5-[2-[(2-Chloro-5-thiazolyl)methoxy]styryl]-2,3-dihydro-1-methyl-1H-1,4-benzodiazepine |
| 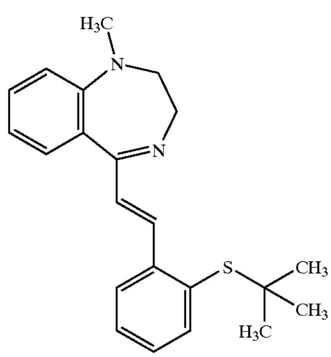 | (E)-5-[2-(tert-Butylthio)styryl]-2,3-dihydro-1-methyl-1H-1,4-benzodiazepine |
| 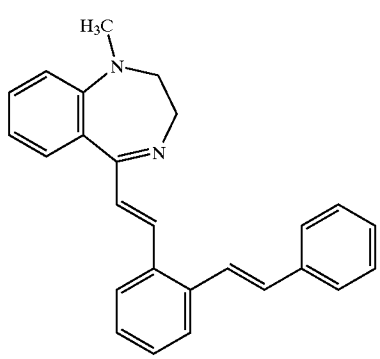 | (all-E)-2,3-Dihydro-1-methyl-5-(2-styrylstyryl)-1H-1,4-benzodiazpeine |

-continued

| Structure | Name |
|---|---|
| 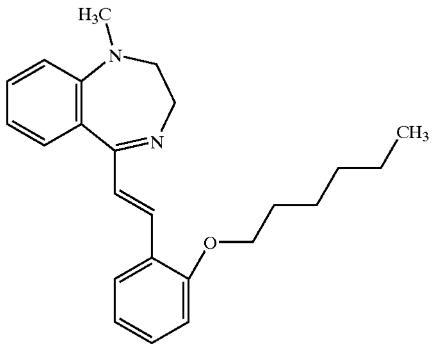 | (E)-5-(2-Hexyloxystyryl)-2,3-dihydro-1-methyl-1H-1,4-benzodiazepine |
| 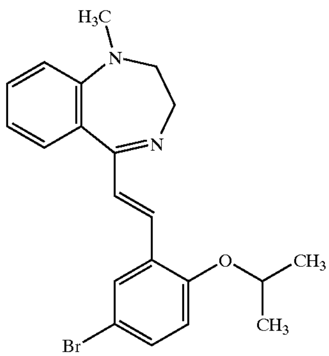 | (E)-5-(5-Bromo-2-isopropoxystyryl)-2,3-dihydro-1-methyl-1H-1,4-benzodiazepine |
| 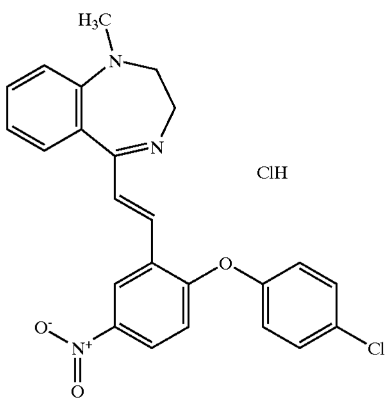 | (E)-5-[2-(4-Chlorophenoxy)-5-nitrostyryl]-3,4-dihydro-1-methyl-1H-1,4-benzodiazepine hydrochloride |
| 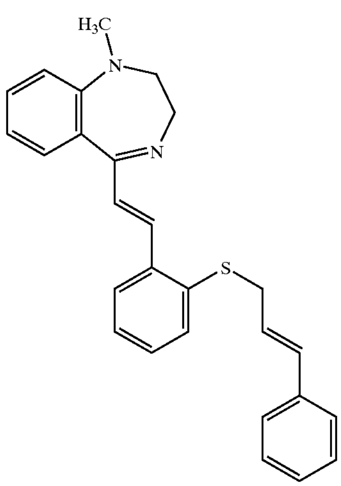 | (all-E)-2,3-Dihydro-1-methyl-5-[2-(styrylthio)styryl]-1H-1,4-benzodiazepine |

-continued
| Structure | Name |
|---|---|
| 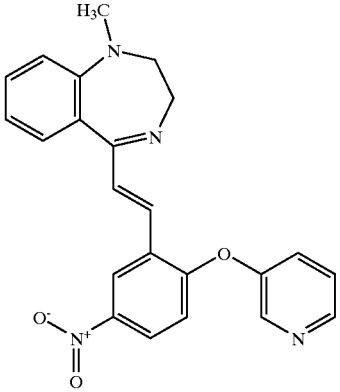 | (E)-2,3-Dihydro-1-methyl-5-[5-nitro-2-(3-pyridyloxy)styryl]-1H-1,4-benzodiazepine |
| 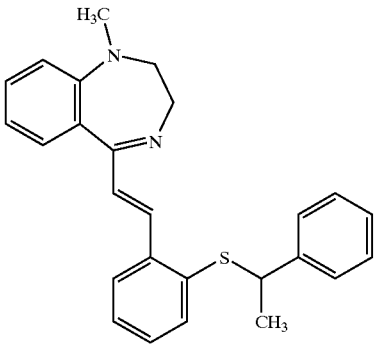 | (E)-2,3-Dihydro-1-methyl-5-[2-(1(RS)-phenylethylthio)styryl]-1H-1,4-benzodiazepine |
| 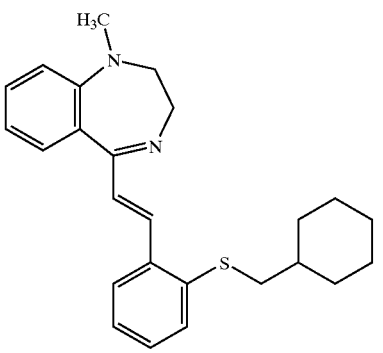 | (E)-5-[2-(Cyclohexylmethylthio)styryl]-2,3-dihydro-1-methyl-1H-1,4-benzodiazepine |
| 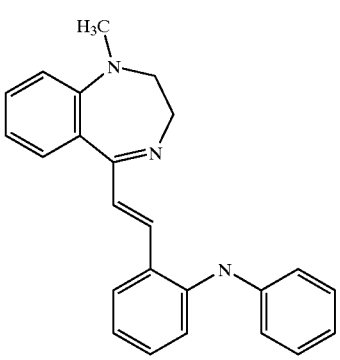 | (E)-N-[2-[2-(2,3-Dihydro-1-methyl-1H-1,4-benzodiazepin-5-yl)vinyl]phenyl]aniline |

-continued

| Structure | Name |
|---|---|
| 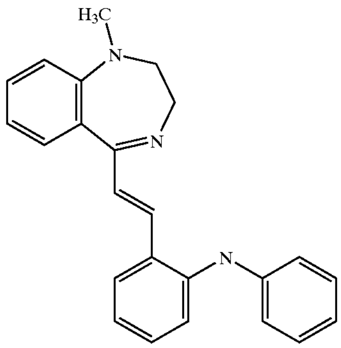 | (E)-N-[2-[2-(2,3-Dihydro-1-methyl-1H-1,4-benzodiazepin-5-yl)vinyl]phenyl]aniline |
| 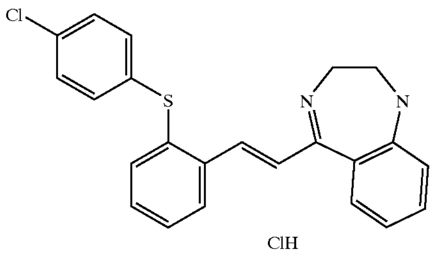 | (E)-5-[2-(4-Chlorophenylthio)styryl]-2,3-dihydro-1H-1,4-benzodiazepine hydrochloride |
| 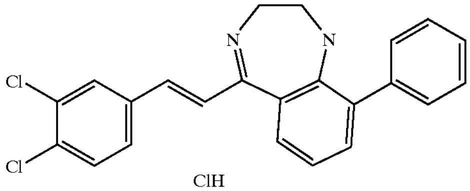 | (E)-5-(3,4-Dichlorostyryl)-2,3-dihydro-9-phenyl-1H-1,4-benzodiazepine hydrochloride |
| 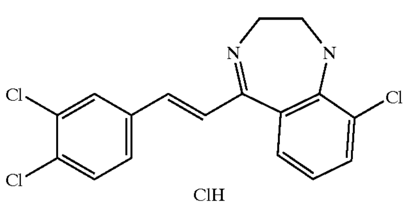 | (E)-9-Chloro-5-(3,4-dichlorostyryl)-2,3-dihydro-1H-1,4-benzodiazepine dihydrochloride |
| 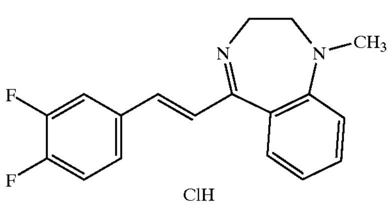 | (E)-5-(3,4-Dichlorostyryl)-2,3-dihydro-1-methyl-1H-1,4-benzodiazepine dihydrochloride |

| Structure | Name |
|---|---|
| 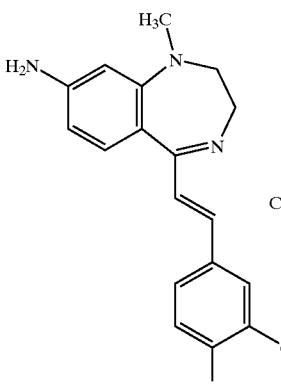 | (E)-5-(3,4-Dichlorostyryl)-2,3-dihydro-1-methyl-1H-1,4-benzodiazepin-8-amine hydrochloride |
| 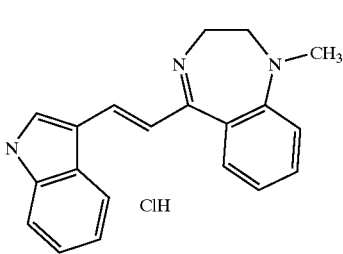 | (E)-2,3-Dihydro-5-[2-(1H-indol-3-yl)vinyl]-1-methyl-1H-1,4-benzodiazepine hydrochloride |
or pharmaceutically acceptable salts thereof.
* * * * *

UNITED STATES PATENT AND TRADEMARK OFFICE
CERTIFICATE OF CORRECTION

PATENT NO. : 6,703,387 B2  
DATED : March 9, 2004  
INVENTOR(S) : David N. Hurst et al.

It is certified that error appears in the above-identified patent and that said Letters Patent is hereby corrected as shown below:

Column 184,

Structure 2,  should be 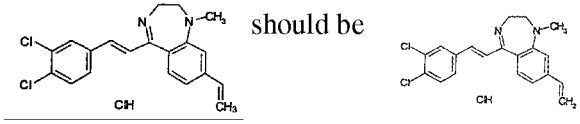

Structure 3,  should be 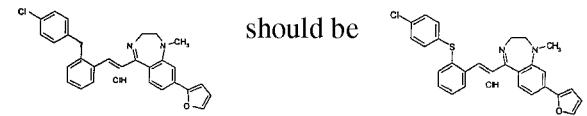

Column 218,
First Structure Name "…(2,3-Dihydro-1-methyl-1H-1,3…" should be -- …(2,3-Dihydro-1-methyl-1H-1,4… --

Column 238,
Fifth Structure Name "…(3,4-Dichlorostyryl)…" should be -- …(3,4-Difluorostyryl)… --

Signed and Sealed this

Twenty-fourth Day of August, 2004

JON W. DUDAS  
*Director of the United States Patent and Trademark Office*